(12) United States Patent
Uhrich et al.

(10) Patent No.: US 9,782,432 B2
(45) Date of Patent: Oct. 10, 2017

(54) POLYMERS AND METHODS THEREOF FOR WOUND HEALING

(71) Applicant: RUTGERS, THE STATE UNIVERSITY OF NEW JERSEY, New Brunswick, NJ (US)

(72) Inventors: Kathryn E. Uhrich, New Brunswick, NJ (US); Sabrina S. Snyder, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 14/973,519

(22) Filed: Dec. 17, 2015

(65) Prior Publication Data

US 2016/0175343 A1     Jun. 23, 2016

Related U.S. Application Data

(62) Division of application No. 14/061,272, filed on Oct. 23, 2013, now abandoned.

(60) Provisional application No. 61/718,556, filed on Oct. 25, 2012.

(51) Int. Cl.
*A61K 31/765* (2006.01)

(52) U.S. Cl.
CPC .................. *A61K 31/765* (2013.01)

(58) Field of Classification Search
None
See application file for complete search history.

(56) References Cited

U.S. PATENT DOCUMENTS

| 2,607,799 A | 8/1952 | Weesner |
| 4,062,855 A | 12/1977 | Allan et al. |

(Continued)

FOREIGN PATENT DOCUMENTS

| AU | 750424 | 3/2003 |
| CA | 2393676 | 7/2002 |

(Continued)

OTHER PUBLICATIONS

Carbone et al., Macromol. Rapid Commun., 2009, vol. 30, pp. 1021-1026.*

(Continued)

*Primary Examiner* — Brian Gulledge
(74) *Attorney, Agent, or Firm* — Viksnins Harris Padys Malen LLP

(57) ABSTRACT

Certain embodiments of the invention provide a copolymer having a backbone, wherein the backbone comprises a) one or more units that comprise a group that will yield a biologically active agent upon hydrolysis of the backbone; and b) one or more units of formula (II):

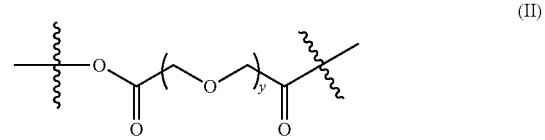

wherein y is 1 or more. Other embodiments of the invention provide a therapeutic method for treating a wound in an animal comprising administering to an animal in need of such therapy, an effective amount of a copolymer as described herein.

17 Claims, 13 Drawing Sheets

(56) References Cited

U.S. PATENT DOCUMENTS

| | | |
|---|---|---|
| 4,126,445 A | 11/1978 | Allan et al. |
| 4,164,560 A | 8/1979 | Folkman et al. |
| 4,298,595 A | 11/1981 | Parkinson et al. |
| 4,375,968 A | 3/1983 | Manhart et al. |
| 4,414,203 A | 11/1983 | Cabardo, Jr. et al. |
| 4,591,496 A | 5/1986 | Cohen et al. |
| 4,612,302 A | 9/1986 | Szabo et al. |
| 4,684,620 A | 8/1987 | Hruby et al. |
| 4,757,128 A | 7/1988 | Domb et al. |
| 4,792,598 A | 12/1988 | Ziegast |
| 4,840,626 A | 6/1989 | Linsky et al. |
| 4,857,311 A | 8/1989 | Domb et al. |
| 4,868,274 A | 9/1989 | Gupta et al. |
| 4,886,870 A | 12/1989 | D'Amore et al. |
| 4,888,176 A | 12/1989 | Langer et al. |
| 4,891,225 A | 1/1990 | Langer et al. |
| 4,906,474 A | 3/1990 | Langer et al. |
| 4,916,204 A | 4/1990 | Domb et al. |
| 4,938,949 A | 7/1990 | Borch et al. |
| 4,997,904 A | 3/1991 | Domb |
| 4,999,417 A | 3/1991 | Domb |
| 5,007,916 A | 4/1991 | Linsky et al. |
| 5,032,216 A | 7/1991 | Felten |
| 5,082,925 A | 1/1992 | Shalaby et al. |
| 5,160,745 A | 11/1992 | DeLuca et al. |
| 5,175,235 A | 12/1992 | Domb et al. |
| 5,259,968 A | 11/1993 | Emert et al. |
| 5,264,540 A | 11/1993 | Cooper et al. |
| 5,290,494 A | 3/1994 | Coombes et al. |
| 5,317,079 A | 5/1994 | Domb et al. |
| 5,364,725 A | 11/1994 | Wilson et al. |
| 5,498,729 A | 3/1996 | Domb |
| 5,512,131 A | 4/1996 | Kumar et al. |
| 5,514,764 A | 5/1996 | Frechet et al. |
| 5,518,730 A | 5/1996 | Fuisz |
| 5,545,409 A | 8/1996 | Laurencin et al. |
| 5,629,009 A | 5/1997 | Laurencin et al. |
| 5,660,851 A | 8/1997 | Domb |
| 5,721,131 A | 2/1998 | Rudolph et al. |
| 5,776,748 A | 7/1998 | Singhvi et al. |
| 5,798,115 A | 8/1998 | Santerre et al. |
| 5,837,278 A | 11/1998 | Geistlich et al. |
| 5,889,028 A | 3/1999 | Sandborn et al. |
| 5,891,477 A | 4/1999 | Lanza et al. |
| 5,902,110 A | 5/1999 | Alfano et al. |
| 5,902,599 A | 5/1999 | Anseth et al. |
| 5,916,585 A | 6/1999 | Cook et al. |
| 5,937,758 A | 8/1999 | Maracas et al. |
| 5,942,252 A | 8/1999 | Tice et al. |
| 5,958,911 A | 9/1999 | Evans et al. |
| 5,969,020 A | 10/1999 | Shalaby et al. |
| 6,071,530 A | 6/2000 | Polson et al. |
| 6,123,956 A | 9/2000 | Baker et al. |
| 6,150,581 A | 11/2000 | Jiang et al. |
| 6,153,212 A | 11/2000 | Mao et al. |
| 6,171,610 B1 | 1/2001 | Vacanti et al. |
| 6,280,772 B1 | 8/2001 | Pinkus |
| 6,365,149 B2 | 4/2002 | Vyakarnam et al. |
| 6,468,519 B1 | 10/2002 | Uhrich |
| 6,486,214 B1 | 11/2002 | Uhrich |
| 6,602,915 B2 | 8/2003 | Uhrich |
| 6,613,807 B2 | 9/2003 | Uhrich |
| 6,685,928 B2 | 2/2004 | Uhrich et al. |
| 6,689,350 B2 | 2/2004 | Uhrich |
| 7,122,615 B1 | 10/2006 | Uhrich |
| 7,144,588 B2 | 12/2006 | Oray et al. |
| 7,396,527 B2 | 7/2008 | Uhrich |
| 7,411,031 B2 | 8/2008 | Uhrich et al. |
| 7,534,852 B2 | 5/2009 | Uhrich |
| 7,662,864 B2 | 2/2010 | Kanamathareddy et al. |
| 7,666,398 B2 | 2/2010 | Uhrich |
| 7,901,705 B2 | 3/2011 | Roby et al. |
| 7,985,415 B2 | 7/2011 | Giroux |
| 8,017,714 B2 | 9/2011 | Uhrich |
| 8,088,405 B2 | 1/2012 | Uhrich et al. |
| 8,221,790 B2 | 7/2012 | Uhrich |
| 8,232,322 B2 | 7/2012 | East et al. |
| 8,241,668 B2 | 8/2012 | Uhrich et al. |
| 8,263,060 B2 | 9/2012 | Uhrich et al. |
| 8,361,453 B2 | 1/2013 | Uhrich et al. |
| 8,741,317 B2 | 6/2014 | Uhrich et al. |
| 8,747,832 B2 | 6/2014 | Uhrich et al. |
| 9,108,070 B2 | 8/2015 | Kanamathareddy et al. |
| 9,144,579 B2 | 9/2015 | Uhrich et al. |
| 9,387,250 B2 | 7/2016 | Uhrich et al. |
| 2001/0046476 A1 | 11/2001 | Plochocka |
| 2003/0035787 A1 | 2/2003 | Uhrich et al. |
| 2003/0059469 A1 | 3/2003 | Uhrich et al. |
| 2004/0038948 A1 | 2/2004 | Uhrich et al. |
| 2004/0044125 A1 | 3/2004 | Uhrich et al. |
| 2004/0096476 A1 | 5/2004 | Uhrich et al. |
| 2004/0198641 A1 | 10/2004 | Uhrich et al. |
| 2004/0228832 A1 | 11/2004 | Uhrich et al. |
| 2005/0031577 A1 | 2/2005 | Uhrich et al. |
| 2005/0053577 A1 | 3/2005 | Uhrich et al. |
| 2005/0089504 A1 | 4/2005 | Uhrich et al. |
| 2005/0089506 A1 | 4/2005 | Uhrich et al. |
| 2005/0100526 A1 | 5/2005 | Uhrich et al. |
| 2005/0131199 A1 | 6/2005 | Uhrich et al. |
| 2005/0249697 A1 | 11/2005 | Uhrich et al. |
| 2006/0013851 A1 | 1/2006 | Giroux et al. |
| 2006/0039964 A1 | 2/2006 | Uhrich et al. |
| 2006/0057179 A1 | 3/2006 | Giroux et al. |
| 2007/0098800 A1 | 5/2007 | Giroux et al. |
| 2007/0196417 A1 | 8/2007 | Uhrich et al. |
| 2008/0317705 A1* | 12/2008 | Kelly .................. A61K 9/0019 424/85.1 |
| 2009/0060979 A1* | 3/2009 | Bezwada ............. C08G 63/672 424/426 |
| 2010/0152410 A1 | 6/2010 | East et al. |
| 2010/0291180 A1 | 11/2010 | Uhrich et al. |
| 2010/0291181 A1 | 11/2010 | Uhrich et al. |
| 2010/0310498 A1 | 12/2010 | Kanamathareddy et al. |
| 2011/0022161 A1 | 1/2011 | Uhrich et al. |
| 2013/0022569 A1 | 1/2013 | Uhrich et al. |
| 2013/0071458 A1 | 3/2013 | Kanamathareddy et al. |
| 2014/0030341 A1 | 1/2014 | Uhrich et al. |
| 2014/0050692 A1 | 2/2014 | Uhrich et al. |
| 2014/0120057 A1 | 5/2014 | Uhrich et al. |
| 2014/0271864 A1 | 9/2014 | Uhrich et al. |
| 2016/0058776 A1 | 3/2016 | Kanamathareddy et al. |
| 2016/0130211 A1 | 5/2016 | Uhrich et al. |

FOREIGN PATENT DOCUMENTS

| | | |
|---|---|---|
| DE | 288311 | 3/1991 |
| DE | 0288387 | 3/1991 |
| EP | 0246341 | 11/1987 |
| EP | 0483429 | 5/1992 |
| EP | 0498283 | 8/1992 |
| EP | 0580386 | 1/1994 |
| FR | 2839451 | 11/2003 |
| JP | 51134729 | 11/1976 |
| JP | 53082743 | 7/1978 |
| JP | 56007716 | 1/1981 |
| JP | 6255797 | 12/1985 |
| JP | 61186309 | 8/1986 |
| JP | 06328857 | 11/1994 |
| JP | 07149044 | 6/1995 |
| NL | 9000237 | 8/1991 |
| WO | 9009779 | 9/1990 |
| WO | 9109831 | 7/1991 |
| WO | 9118940 | 12/1991 |
| WO | 9739738 | 10/1997 |
| WO | 9744016 | 11/1997 |
| WO | 9749385 | 12/1997 |
| WO | 9836013 | 8/1998 |
| WO | 9912990 | 3/1999 |
| WO | 9929885 | 6/1999 |
| WO | 9936107 | 7/1999 |
| WO | 0066730 | 11/2000 |
| WO | 0128492 | 4/2001 |
| WO | 0141753 | 6/2001 |
| WO | 0209767 | 2/2002 |

| | | |
|---|---|---|
| WO | 0209768 | 2/2002 |
| WO | 0209769 | 2/2002 |
| WO | 03046034 | 6/2003 |
| WO | 03065928 | 8/2003 |
| WO | 03066053 | 8/2003 |
| WO | 03072020 | 9/2003 |
| WO | 2004006863 | 1/2004 |
| WO | 2004039355 | 5/2004 |
| WO | 2004045549 | 6/2004 |
| WO | 2005039489 | 5/2005 |
| WO | 2005042600 | 5/2005 |
| WO | 2006127667 | 11/2006 |
| WO | 2007143698 | 12/2007 |
| WO | 2008034019 | 3/2008 |
| WO | 2008103744 | 8/2008 |
| WO | 2008128193 | 10/2008 |
| WO | 2009026544 | 2/2009 |
| WO | 2012139015 | 10/2012 |
| WO | 2014194055 | 12/2014 |
| WO | 2015191742 | 12/2015 |

OTHER PUBLICATIONS

Muzii et al., Human Reproduction, 1998, 13(6), pp. 1486-1489.*
Erdmann, "Polymeric Prodrugs: Novel Polymers for Delivery of Salicylic Acid", Annals of Biomedical Engineering, 26 (Suppl. 1), Abstract No. PB.26, Annual Fall Meeting, S-124, (1998).
Erdmann, "Polymeric Salicylic Acid: In Vitro and In Vivo Degradation", Polymer Preprints, 39(2), 224-225, (1998).
Erdmann, "Synthesis and degradation characteristics of salicylic acid-derived poly(anhydride-esters)", Biomaterials, 21(19), 1941-1946, (Oct. 2000).
Ersoz, et al., "Melatonin prevents peritoneal adhesions in rats", Journal of Gastroenterology and Hepatology 24, 1763-1767 (2009).
Freitas, et al., "Microencapsulation by solvent extraction/evaporation: reviewing the state of the art of microsphere preparation process technology", Journal of Controlled Release 102, 313-332 (2005).
Giammona, "Polymeric Prodrugs alpha beta poly-hyroxyethyl-d1-aspartamide as macromolecular carrier for some non-steroidal anti-inflammatory agents", Abstracts from Database BIOSIS Online, Biosciences Information Service, Philadelphia, PA, Original Publication from the International Journal of Pharmaceutics (Amsterdam), 1 page (1989).
Giammona, "Polymeric Prodrugs Alpha Beta Poly-N-hydroxyethyl-DL-aspartamide as a Macromolecular Carrier for Some Non-Steroidal Anti-inflammatory Agents", International Journal of Pharmaceutics, 57, 55-62, (1989).
Golan, et al., "Prevention of post-surgical adhesion formation using aspirin in a rodent model: a preliminary report", Human Reproduction 10 (6), 1797-1800 (1995).
Gouin, et al., "New Polyanhydrides Made from a Bile Acid Dimer and Sebacic Acid: Synthesis, Characterization and Degradation", Macromolecules, 33, 5379-5383, (2000).
Griffin, et al., "Salicylic acid-derived poly(anhydride-ester) electrospun fibers designed for regenerating the peripheral nervous system", Journal of Biomedical Materials Research Part A, 97(3), 230-242 (2011).
Hammouda, et al., "Aspirin and venous occlusion: effects on blood fibrinolytic activity and tissue-type plasminogen activator levels", Thrombosis Research 42, 73-82 (1986).
Harten, et al., "Salicylic acid-derived poly(anhydride-esters) inhibit bone resorption and formation in vivo", J. Biomed Mater Res A 72(4), 354-362 (2005).
Herbert, "Micropatterning gradients and controlling surface densities of photoactivatable biomolecules on self-assembled monolayers of oligo(ethylene glycol) alkanethiolates", Chemistry & Biology, 4(10), 731-7, (Oct. 1997).
Ibim, "Controlled Release Based on Poly(anhydride-co-imides)", Proc. Intern. Symp. Control. Rel. Bioact. Mater., 22, 2 pgs, (1995).
Ibim, "Poly(anhydride-co-imides): In Vivo Biocompatibility in a rat model", Biomaterials, 19(10), 941-951, (1998).
Ibim, "Preliminary in vivo report on the osteocompatibility of poly(anhydride-co-imides) evaluated in a tibial model.", Journal of Biomedical Material Research, 43(4), 374-379, (Winter 1998).
Imai, et al., "Topical non-barrier agents for postoperative adhesion prevention in animal models", European Journal of obstetrics & Gynecology and Reproductive Biology 149 (2), 131-135 (2010).
Ito, "Micropatterned immobilization of epidermal growth factor to regulate cell function", Bioconjugate Chemistry, 9(2), 277-82, (Mar.-Apr. 1998).
James, "Patterned Protein Layers on Solid Substrates by Thin Stamp Microcontact Printing", Langmuir, 14(4), 741-744, (1998).
Jeffcoat, "The Effect of Systemic Flurbiprofen on Bone Supporting Dental Implants", Journal of American Dental Associate, 126, 305-311 (1995).
Jiang, "Synthesis, Characterization and In Vitro Degradation of a New Family of Alternate Poly(ester-anhydrides) Based on Aliphatic and Aromatic Diacids", Biomaterials, 22(3), 211-218, (2001).
Johnson, et al., "Concurrent release of admixed antimicrobials and salicylic acid from salicylate-based poly (anhydride-esters)", Journal of Biomedical Materials Research, Part A, 91, 671-678 (2009).
Jucker, et al., "Fetal rat septals cells adhere to and extend processes on basement membrane, laminin, and a synthetic peptide from the laminin A chain sequence", Journal of Neuroscience Research, 28(4), 507-17, (Apr. 1991).
Kim, et al.. "Mesenchymal stem cell-educated macrophages: a novel type of alternatively activated macrophages", Experimental Hematology 37 (12), 1445-1453 (2009).
Kleinfeld, "Controlled outgrowth of dissociated neurons on patterned substrates", Journal of Neuroscience, 8(11), 4098-120, (Nov. 1998).
Krogh-Jespersen, "Synthesis of a Novel Aromatic Polyanhydride Containing Aminosalicylic Acid", Polymer Preprints, 41(1), 1048-1049, (2000).
Langer, "New Methods of Drug Delivery", Science, 249(4976), 1527-1533, (Sep. 1990).
Laurencin, "Poly(anhydrides-co-imides): In Vivo Biocompatibility Study", 23rd Annual Meeting of the Society for Biomaterials, New Orleans, LA, 483, (1997).
Laurencin, "The Biocompatibility of Poly(anhydride-co-imides): High Strength Polymers for Controlled Drug Delivery", Proc. 24th Int'l Symp. Control. Rel. Bioact. Mater., 973-974, (1997).
Laurencin, "The Bone Biocompatibility of Poly(anhydride-co-imides)—A new generation degradable Polymer for Orthopedic Applications", 41st Annual Meeting of the Orthopedic Research Society, Orlando, FL, 143-24, (1995).
Laurencin, et al., "The controlled delivery of radiosensitizers: taxol treatment for Ewing Sarcoma", Proceedings of the 25th Int'l Symp. Control. Rel. Bioact. Mater., pp. 236-237, (1998).
Longer, "Sustained-Release Drug Delivery Systems", Remington's Pharmaceutical Sciences, 18th Edition, Chapter 91, 1676-1693, (1990).
Macedo, et al., "The in vivo Response to a Bioactive Biodegradable Polymer", Journal of Dental Research, 78, Abstract No. 2827, 459, (1999).
Macedo, "The In Vivo Response to Bioactive Polyanhydride Monofilament", Journal of Dental Research, 79 (Abstract No. 3872), 627, (2000).
March, Advanced organic chemistry: reactions, mechanisms, and structure, 4th Edition, New York: Willey, 419-437 (1992).
Moran, "Adhesion-related small bowel obstruction", Colorectal disease: the official journal of the Association of Coloproctology of Great Britain and Ireland, 9 Suppl, 2, 39-44 (2007).
Muzii, et al., "Postoperative adhesion prevention with low-dose aspirin: effect through the selective inhibition of thromboxane production", Human Reproduction, 13 (6), 1486-1489 (1998).
Ouimet, et al., "Tunable drug release profiles from salicylate-based poly(anhydride-ester) matrices using small molecule admixtures", Journal of Bioactive and Compatible Polymers 27 (6), 540-549 (2012).
Pinther, "Synthesis of Polyanhydrides Containing Ester Groups", Die Makromolekulare Chemie, Rapid Communications, 11(8), 403-408, (Aug. 1990).

Prudencio, et al., "A Novel Approach for Incorporation of Mono-Functional Bioactive Phenols into Polyanhydrides", Macromolecular Rapid Communications, 30, 1101-1108, 2009.
Prudencio, "Biodegradable Polyanhydrides for Controlled Drug Release", Dissertation submitted to the Graduate School—New Brunswick, Rutgers, The State University of New Jersey, 228 pages (Oct. 2006).
Prudencio, et al., "Effect of Linker Structure on Salicylic Acid-Derived Poly(anhydride-esters)", Macromolecules 38, 6895-6901 (2005).
Rajab, et al., "A direct comparison of seprafilm, adept, intercoat, and spraygel for adhesion prophylaxis", Journal of Surgical Research 161 (2), 246-249 (2010).
Reynolds, et al., "Non-steroidal anti-inflammatory drug (NSAID)-derived poly(anhydride-esters) in bone and periodontal regeneration", Current Drug Delivery, 4(3), 233-239 (Jan. 1, 2007).
Rosario-Melendez, et al., "Stability of a salicylate-based poly(anhydride-ester) to electron beam and gamma radiation", Polymer Degradation and Stability 96, 1625-1630 (2011).
Saed, et al., "Modulation of the expression of tissue plasminogen activator and its inhibitor by hypoxia in human peritoneal and adhesion fibroblasts", Fertility and Sterility 79, 164-168 (2003).
Saeidi, et al., "Effect of melatonin in the prevention of postoperative pericardial adhesion formation", Interactive Cardiovascular and Thoracic Surgery 9, 26-28 (2009).
Sammour, "Peritoneal damage: the inflammatory response and clinical implications of the neuro-immuno-humoral axis", World Journal of Surgery 34 (4), 704-720 (2010).
Sandoval, et al., "Preventing peridural fibrosis with nonsteroidal anti-inflammatory drugs", Eur Spine J 17, 451-455 (2008).
Schacht, "Polymers for Colon Specific Drug Delivery", Journal of Controlled Release, 39, 327-338, (1996).
Aebischer, et al., "Basic fibroblast growth factor released from synthetic guidance channels facilitates peripheral nerve regeneration across long nerve gaps", Journal of Neuroscience Research, 23(3), 282-289, (Jul. 1989).
Alpay, et al., "Postoperative Adhesions: From Formation to Prevention", Seminars in Reproductive Medicine 26(4), 313-321 (2008).
Anastasiou, "Novel Polyanhydrides with Enhanced Thermal and Solubility Properties", Macromolecules, 33(17), 6217-6221, (2000).
Anastasiou, "Novel, Degradable Polyanhydrides", 25th Annual Meeting Transactions of the Society for Biomaterials, Abstract, 79, (1999).
Anastasiou, "Synthesis of Novel, Degradable Polyanhydrides Containing Para-Aminosalicylic Acid as Drug Delivery Devices for Tuberculosis Treatment", Polymer Preprints, 41(2), 1366-1367, (Aug. 2000).
Ara, et al., "Protective effect of melatonin against oxidative stress on adhesion formation in the rat cecum and uterine horn model", Life Sciences 77, 1341-1350 (2005).
Arredondo, et al., "Effects of Linkers Substitution on Salicylic Acid-derived Poly(anhydride-esters)", website of Rutgers, the State University of New Jersey, 16 pages (2001).
Attawia, "Biocompatibility Testing of Poly(anhydride-co-imides) Containing Pyromellitylimidoalanine", The 21st Annual Meeting of the Society for Biomaterials, Abstract, 222, (Apr. 5-9, 1994).
Attawia, "Cytotoxicity testing ofpoly(anhydride-co-imides) for orthopedic applications", Journal of Biomedical Materials Research, 29(10), 1233-1240, (1995).
Attawia, "In vitro bone biocompatibility of poly(anhydride-co-imides) containing pyromellitylimidoalanine", Journal of Orthopedic Research, 14(3), 445-454, (1996).
Attawia, "Proliferation, Morphology, and Protein Expression by Osteoblasts Cultured on Poly(anhydride-co-amides)", Journal of Biomedical Materials Research, 48(3), 322-327, (1999).
Attawia, "Regional drug delivery with radiation for the treatment of Ewing's sarcoma—in vitro development of a taxol release system", Journal of Controlled Release, 71, 193-202 (2001).
Attawia, "The Long Term Osteoblast Response to Poly(anhydride-co-imides): A New Degradable Polymer for Use in Bone", Proceedings of the Fifth World Biomaterials Congress, Toronto, Canada, 113, (1996).
Beaton, "Synthesis of a novel poly(anhydride-ester)", The Rutgers Scholar—An Electronic Bulletin of Undergraduate Research, 3, 1-7, (2001), http://www.scils.rutgers.edu/~weyang/ejournal/volume03/beatuhri/beatuhri.htm.
Bedell, "Processing and Hydrolytic Degradation of Aromatic, Ortho-Substituted Polyanhydrides", Journal of Applied Polymer Science, 80, 32-38, (2001).
Brambley, et al., "Microlithography: an overview", Advanced Materials for Optics and Electronics, 4(2), 55-74, (Mar.-Apr. 1994).
Branch, "Microstamp patterns of biomolecules for high resolution neuronal networks", Medical & Biological Engineering & Computing, 36(1), 135-41, (Jan. 1998).
Brostow, et al., "Prediction of glass transition temperatures: Binary blends and copolymers", Materials Letters 62, 3152-3155 (2008).
Brown, "A Polymeric Drug for Treatment of Inflammatory Bowel Disease", Journal of Medicinal Chemistry, 26(9), 1300-1307, (1983).
Brown, et al., "Transdermal delivery of drugs", Annual Review of Medicine, 39, 221-9, (1988).
Buczko, et al., "Aspirin and the fibrinolytic response", Thrombosis Research 110, 331-334 (2003).
Buerke, et al., "Aspirin therapy: optimized platelet inhibition with different loading and maintenance doses", American Heart Journal 130 (3 Pt 1), 465-472 (1995).
Campo, "Polyanhydrides: the effects of ring substitution changes on polymer properties", Polymer Bulletin, 42, 61-68, (1999).
Carbone, et al., "Design and Synthesis of Fast-Degrading Poly(anhydride-esters)", Macromol. Rapid Commun., vol. 30, 1021-1026. (2009).
Celestini, et al., "Vitamin E potentiates the antiplatelet activity of aspirin in collagen-stimulated platelets", Haematologic 87, 420-426 (2002).
Chafi, "Dosage Form with Salicylic Acid Attached to the Polyanhydride Polymer Dispersed in an Eudragit Matrix", International Journal of Pharmaceutics, 52, 203-211, (1989).
Chatterjee, et al., "Mechanism for the Increase in Solubility of Deoxyhemoglobin S due to Cross-Linking the Beta Chains Between Lysine-82 Beta1 and Lysine-82 Beta 2", Biochemistry, 21, 5901-5909, (1982).
Chen, "Effect of protein and cell behavior on pattern-grafted thermoresponsive polymer", Journal of Biomedical Materials Research, 42(1), 38-44, (Oct. 1998).
Conix, "Aromatic Polyanhydrides, a New Class of High Melting Fiber-Forming Polymers", Journal of Polymers Science, XXIX, 343-353, (1958).
Conix, "New High-Melting Fibre-Forming Polymers", Die Makromolekulare Chemie, XXIV, 76-78, (1957).
Conix, "Poly [1,3-bis (p carboxyphenoxy)—Propane anhydride]", Macromolecular Synthesis, 2, 95-99, (1996).
Corrales, et al., "Preventing intraperitoneal adhesions with vitamin E and sodium hyaluronate/carboxymethylcellulose: a comparative study in rats", Acta Cirurgica Brasileira 23, 36-41 (2008).
Cotlier, "Distribution of salicylate in lens and intraocular fluids and its effect on cataract formation", American Journal of Medicine, 74 (6A), 83-90 (1983).
Cotlier, "Senile Cataracts: Evidence for Acceleration by Diabetes and Deceleration by Salicytate", Canadian Journal of Ophthalmology, 16(3), 113-118 (1981).
Davaran, "Release of 5-amino Salicylic Acid from Acrylic Type Polymeric Prodrugs Designed for Colon-specific Drug Delivery", Journal of Controlled Release, 58(3), 279-287, (1999).
Davies, "The Analysis of the Surface Chemical Structure of Biomedical Aliphatic Polyanhydrides Using SPX and ToF-SIMS", Journal of Applied Polymer Science, 42, No. 6, New York, US, 1597-1605, (Mar. 20, 1991).
De La Portilla, et al., "Prevention of peritoneal adhesions by intraperitoneal administration of vitamin E: an experimental study in rats", Diseases of the Colon and Rectum 47 (12), 2157-2161 (2004).

Delamarche, et al., "Patterned delivery of immunoglobulins to surfaces using microfluidic networks", Science, 276 (5313), 779-781, (May 2, 1997).

Demir, et al., "Electrospinning of polyurethane fibers", Polymer 43 (11), 3303-3309 (2002).

Deronde, et al., "Storage stability study of salicylate-based poly(anhydride-esters)", Polymer Degradation and Stability, 95, 1778-1782 (2010).

Dewez, et al., "Adhesion of mammalian cells to polymer surfaces: from physical chemistry of surfaces to selective adhesion on defined patterns", Biomaterials, 19(16), 1441-1445, (Aug. 1998).

Dizerga, et al., "Prevention of intra-abdominal adhesions in gynaecological surgery", Reproductive Biomedicine Online 17, 303-306 (2008).

Domb, "Polyanhydrides. I. Preparation of High Molecular Weight Polyanhydrides", Journal of Polymer Science: Part A: Polymer Chemistry, 25, 3373-3386, (1987).

Domb, "Synthesis and Characterization of Biodegradable Aromatic Anhydride Copolymers", Macromolecules, 25, 12-17, (1992).

Dontha, "Generation of biotin/avidin/enzyme nanostructures with maskless photolithography", Analytical Chemistry, 69(14), 2619-25, (Jul. 15, 1997).

Dukovic, "Novel degradable poly(anhydride-esters) for controlled drug release", The Rutgers Scholar—An Electronic Bulletin of Undergraduate Research, 1, 1-10, (1999), http://www.scils.rutgers.edu/~weyang/ejournal/volume01/uhriduko/uhriduko.htm.

Erdman, et al., "Synthesis and Characterization of a Polymeric Prodrug", Proceedings of the American Chemical Society Division of Polymeric Materials: Science and Engineering, 78, Abstract Spring Meeting, Dallas, TX, pp. 194, (Apr. 1998).

Erdmann, et al., "Chapter 5, Polymeric Prodrugs: Novel Polymers with Bioactive Components in Tailored Polymeric Materials for Controlled Delivery Systems", ACS Symposium Series 709, Developed from a symposium sponsored by the Division of Polymer Chemistry at the 214th National Meeting of the American Chemical Society, Washington D.C., 83-91 (1998).

Erdmann, "Degradable poly(anhydride ester) implants: effects of localized salicylic acid release on bone", Biomaterials, 21(24), 2507-2512, (2000).

Erdmann, "Polymer Prodrugs with Pharmaceutically Active Degradation Products", Polymer Preprints, 38(2), 570-571, (1997).

Schmalenberg, "Microlithographic patterning of polymer substrates for directed neuronal", Polymeric Materials Science Engineering, 81, Fall Meeting, Aug. 22-26, 1999, New Orleans, LA., 97, (1999).

Schmalenberg, "Patterned Polymer Substrates for directing Neuronal Growth", ACS Regional Mid-Atlantic Research Meeting, (1999).

Schmalenberg, "Patterning of polymer substrates for directed neuronal growth studies", Laboratory for Surface Moditication,(Mar. 18, 1999).

Schmalenberg, "Thin Stamp Microcontact Patterned Printing of Protein Layers on Polymer Substrates", Transactions: Twenty-Fifth Annual Meeting of the Society for Biomaterials, Apr. 28-May 2, (1999).

Schmeltzer, et al., "Comparison of salicylate-based poly(anhydride-esters) formed via melt-condensation versus solution polymerization", Journal of Biomaterials Science: Polymer Edition 19 (10), 1295-1306 (2008).

Schmeltzer, et al., "Optimized Synthesis of Salicylate-based Poly(anhydride-esters)", Polymer Bulletin 49 (6), 441-448 (2003).

Schmeltzer, et al., "Synthesis and cytotoxicity of salicylate-based poly(anhydride esters)", Biomacromolecules, 6 (1), 359-367 (2005).

Seidel, "Erosion of Poly(anhydride-co-imides): A Preliminary Mechanistic Study", J. Appl. Polym. Sci., 62(8), 1277-1283, (1996).

Shen, "Morphological Characterization of Erodible Polymer Carriers for Drug Release", Proc. 26th Int'l Symp. Control. Rel. Bioact. Mater., 717-718, (1999).

Snyder, "Design and Fabrication of Salicylic Acid-Based Polyanhydride Devices for Wound Healing and Tissue Regeneration", Dissertation, 175 pages (2013).

Snyder, et al., "Salicylic Acid-based Poly(anhydride-esters) for the Prevention of Fibrous Adhesions", Abstract, BMES National Meeting, Atlanta, Georgia, (Aug. 2012).

Snyder, et al., "Salicylic Acid-based Poly(anhydride-esters) for the Prevention of Fibrous Adhesions", Poster, BMES National Meeting, Atlanta, Georgia, (Oct. 2012).

Spargo, et al., "Spatially controlled adhesion, spreading, and differentiation of endothelial cells on self-assembled molecular monolayers", Proceedings of the National Academy of Science USA,91(23), 11070-11074, (Nov. 8, 1994).

Sparks, et al., "Life after Union: Polymers-R-Us", Presentation at Union College, 40 pages (2007).

St. John, "Diffraction-based cell detection using a microcontact printed antibody grating", Analytical Chemistry, 70(6), 1108-11, (Mar. 15, 1998).

Swinyard, "Pharmaceutical Necessities", In: Remington's pharmaceutical sciences by Joseph P. Remington; Alfonso R. Gennaro, Easton, PA.: Mack Pub. Co.: ISBN: 0912734043, 1286-1329 (1990).

Tashiro, et al., "A synthetic peptide containing the IKVAV sequence from the A chain of laminin mediates cell attachment, migration, and neurite outgrowth", Journal of Biological Chemistry, 264(27), 16174-82, (Sep. 25, 1989).

Tingstedt, et al., "Prevention of abdominal adhesions—present state and what's beyond the horizon?", Eur Surg Res 39 (5), 259-268 (2007).

Tziampazis, et al., "PEG-variant biomaterials as selectively adhesive protein templates: model surfaces for controlled cell adhesion and migration", Biomaterials 21 (5), 511-520 (2000).

Uhrich, "Chemical Changes during in vivo degradation of poly(anhydride-imide) matrices", Biomaterials, 19(22), 2045-2050, (1998).

Uhrich, "Degradation of poly(anhydride-co-imides): Novel Polymers for Orthopedic Applications", Mat. Res. Soc. Symp. Proc., 394, 41-46, (1995).

Uhrich, "Designing Polymers for Biomedical Applications", Presentation at Division of Engineering & Applied Science, Harvard University, Cambridge, MA, 50 pages (2002).

Uhrich, "In Vitro Degradation Characteristics of Poly(anhydride-imides) Containing Pyromellitylimidoalanine", J. Appl. Polymer Sci., Part A, Polym. Chem., 34(7), 1261-1269, (1996).

Uhrich, "In Vitro Degradation Characteristics of Poly(anhydride-imides) Containing trimellitylimidoglycine", J. Appl. Polymer. Sci., 63(11), 1401-1411, (1997).

Uhrich, "Poly(anhydride-ester) Degradation: Mechanical Changes and Correlation to Antibiotic Release", American chemical Society, Abstracts of Papers, Part 2, Abstract No. 121, 221st ACS National Meeting, San Diego, CA, Abstract 121, (2001).

Uhrich, "Synthesis and Characterization of Degradable poly(anhydride-co-imides)", Macromolecules, 28(7), 2184-2193, (1995).

Uhrich, "Synthesis and Characterization of poly(anhydride co-imides): Solution Polycondensation of Biodegradable Polymers Derived from Amino Acids", Proc. of the American Chemical Society, Division of Polymeric Materials: Science and Engineering, 70, Spring Meeting, San Diego, CA, 239-240, (1994).

Uhrich, "Synthesis of Aminosalicylate-based polyanhydride Prodrugs: Esters, Amides, and Azos", American Chemical Society, Abstracts of Papers, Part 2, Abstract No. 407, 222nd ACS National Meeting, Chicago, IL, Abstract 407, (2001).

Uhrich, "Topical Liquid or Gel Applied Inside a Surgical Wound", NineSigma Grant Proposal, 6 pages, (2011).

Van Der Wal, et al., "Biology of the peritoneum in normal homeostasis and after surgical trauma", Colorectal disease: the official journal of the Associate of Coloproctology of Great Britain and Ireland, 9 Suppl 2, 9-13 (2007).

Ward, et al., "Abdominal adhesions: current and novel therapies", Journal of Surgical Research 165 (1), 91-111 (2011).

Whitaker Brothers, et al., "Investigation into the erosion mechanism of salicylate-based poly(anhydride-esters)", Journal of Biomedical Materials Research, Part A, 76, 470-479 (2006).

Wilson, et al., "Demonstrating the clinical and cost effectiveness of adhesion reduction strategies", Colorectal Disease, 4, 355-360 (2002).

Wilson, "Practicalities and costs of adhesions", Colorectal disease: the official journal of the Association of Coloproctology of Great Britain and Ireland, 9 Suppl 2, 60-65 (2007).

Wiseman, et al., "Disorders of adhesions or adhesion-related disorder: monolithic entities or part of something bigger—CAPPS?", Seminal Reproductive Medicine 26, 356-368 (2008).

Woo, "Biological Characterization of a Novel Biodegradable Antimicrobial Polymer Synthesized with Fluoroquinolones", J. Biomed. Mater. Res. 59, 35-45, (2002).

Woo, et al., "Synthesis and characterization of a novel biodegradable antimicrobial polymer", Biomaterials, 21, 1235-1246 (2000).

Yang, et al., "Fabrication and characterization of hydrophilic electrospun membranes made from the block copolymer of poly-(ethylene glycol-co-lactide)", Journal of Biomedical Materials Research, Part A, 82, 680-688 (2007).

Yang, et al., "Tissue anti-adhesion potential of biodegradable PELA electrospun membranes", Acta Biomaterialia 5 (7), 2467-2474 (2009).

Yazdi, et al., "Effects of non-steroidal anti-inflammatory drugs on demineralized bone-induced bone formation", Journal of Periodontal Research, 27(1), 28-33, (Jan. 1992).

Yeagy, et al., "Characterization and in vitro degradation of salicylate-derived poly(anhydride-ester microspheres)", Journal of Microencapsulation 23 (6), 643-653 (2006).

Yoda, "Synthesis of polyanhydrides. XII. Crystalline and high melting polyamidepolyanhydride of methylenebis(p-carboxybhenyl)amide", Journal of Polymer Science, 1, 1323-1338, (1963).

Zaugg, et al., "Modification of Hemoglobin with Analogs of Aspirin", The Journal of Biological Chemistry, 255(7), 2816-2821, (1980).

Zong et al "Prevention of postsurgery-induced abdominal adhesions by electrospun bioabsorbable nanofibrous poly(lactide-co-glycolide)-based membranes", Annals of Surgery 240, 910-915 (2004).

\* cited by examiner

POLYMERS AND METHODS THEREOF FOR WOUND HEALING

CROSS-REFERENCE TO RELATED APPLICATION(S)

This application is a divisional of U.S. application Ser. No. 14/061,272, filed Oct. 23, 2013, which claims the benefit of U.S. Provisional Application Ser. No. 61/718,556, filed Oct. 25, 2012. The entire content of the applications referenced above are hereby incorporated by reference herein.

GOVERNMENT FUNDING

This invention was made with government support under R01DE019926 awarded by the National Institutes of Health. The government has certain rights in the invention.

BACKGROUND OF THE INVENTION

Fibrous adhesions are a serious complication that can arise from trauma to the body as they can lead to chronic pain, infertility, and intestinal obstruction. Adhesions are bands of fibrous tissue that join two surfaces in the body, which are not normally connected. They generally form after injury to an area that results in increased inflammation. Surgery, trauma, infections, radiation, and ischemia can all lead to adhesion formation, with surgery being the most common cause. Fibrous adhesions have an enormous impact on the healthcare system. It has been estimated that 95% of abdominal and pelvic surgeries, including gynecologic, result in adhesions. Adhesion-related problems account for 6% of all hospital readmissions and 1% of all hospitalizations in the United States. Adhesions increase surgery time, hospital stay, complications, blood loss, morbidity, and mortality.

In addition to improved surgical techniques, both pharmaceuticals and physical barriers have been explored as means to prevent adhesion formation (Tingstedt et al., Eur Surg Res 39, 259-268 (2007); Ward, et al., Journal of Surgical Research, 165(1), 91-111 (2009)). Systemic administration of such drugs at therapeutic levels can cause undesired side effects and delay healing after surgery. There have been some attempts to inject the drugs into the peritoneal cavity; however, most of these have shown little to no efficacy in laboratory testing primarily due to the tendency for drugs placed in the peritoneal cavity to be quickly absorbed by the mesothelium and subsequently distributed throughout the body. Various solids, gels, and fluids have been used as physical barriers. None of these devices have been shown efficacious enough at reducing adhesion formation to warrant their ubiquitous use.

Accordingly, there is a need for more efficacious treatments for wound healing (e.g., the mitigation of pain, inflammation and/or other complications, such as fibrous adhesions).

SUMMARY OF THE INVENTION

Certain embodiments of the invention provide a copolymer having a backbone, wherein the backbone comprises a) one or more units that comprise a group that will yield a biologically active agent upon hydrolysis of the backbone; and b) one or more units of formula (II):

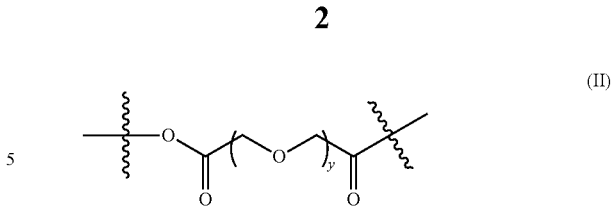

wherein y is 1 or more.

Certain embodiments of the invention provide a pharmaceutical composition comprising a copolymer as described herein and a pharmaceutically acceptable carrier.

Certain embodiments of the invention provide a method of making a copolymer as described herein comprising co-polymerizing (a) one or more monomer(s) that comprises one or more units that comprise a group that will yield a biologically active agent upon hydrolysis of the backbone; and (b) one or more monomer(s) that comprises one or more units of formula (II); under conditions to provide the polymer.

Certain embodiments of the invention provide a method of making a copolymer as described herein.

Certain embodiments of the invention provide a copolymer prepared by methods described herein.

Certain embodiments of the invention provide a therapeutic method for treating a wound in an animal comprising administering to an animal in need of such therapy, an effective amount of a copolymer or composition as described herein.

Certain embodiments of the invention provide a therapeutic method for the prevention of fibrous adhesions at a wound site in an animal comprising administering to an animal in need of such therapy, an effective amount of a copolymer or composition as described herein.

Certain embodiments of the invention provide a therapeutic method for providing localized analgesia at a wound site in an animal comprising administering to an animal in need of such therapy, an effective amount of a copolymer or composition as described herein.

Certain embodiments of the invention provide a method for promoting wound healing in an animal, comprising contacting a copolymer or composition as described herein with a wound of the animal.

Certain embodiments of the invention provide a method for the prevention of fibrous adhesions at a wound site in an animal, comprising contacting a copolymer or composition as described herein with the wound of the animal.

Certain embodiments of the invention provide a method for providing localized analgesia at a wound site in an animal, comprising contacting a copolymer or composition as described herein with the wound of the animal.

Certain embodiments of the invention provide a copolymer or composition as described herein for use in medical therapy.

Certain embodiments of the invention provide for the use of a copolymer or composition as described herein for the manufacture of a medicament for the treatment of a wound in an animal, such as a human.

Certain embodiments of the invention provide a copolymer as described herein for use in treating a wound.

BRIEF DESCRIPTION OF THE FIGURES

FIG. 7A) microspheres; FIG. 7B) flexible films; and FIG. 7C) polymer powder dispersed within mineral oil.

(FIG. 9A) Degradation of the SAPAE to SA and other biocompatible molecules. (FIG. 9B) In vitro salicylic acid release profile from the SAPAE indicates a linear release profile over the critical period of adhesion formation. (FIG. 9C) Fibroblast viability and proliferation is not significantly affected by 0.1 mg/mL SAPAE. (FIG. 9D) 0.1 mg/mL SAPAE significantly (p<0.001) decreases TNF-α expression by LPS activated macrophages, thus demonstrating its ability to inhibit inflammation.

DETAILED DESCRIPTION

Copolymers

Figure 1:
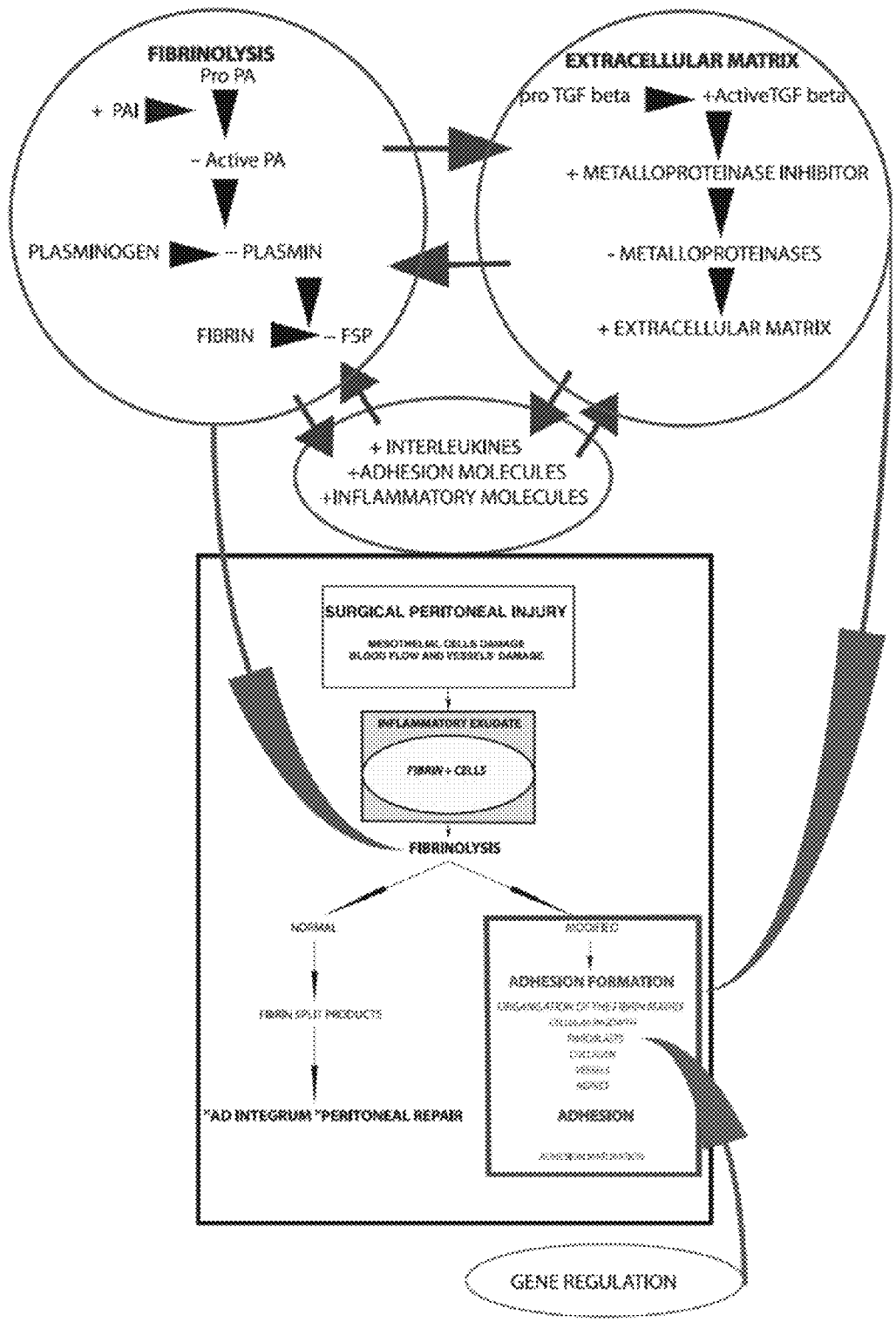
FIG. 1. Diagram of the steps that lead from surgical trauma to either normal peritoneum repair or adhesion formation.

Certain embodiments of the invention provide a copolymer having a backbone, wherein the backbone comprises a) one or more units that comprise a group that will yield a biologically active agent upon hydrolysis of the backbone; and b) one or more units of formula (II):

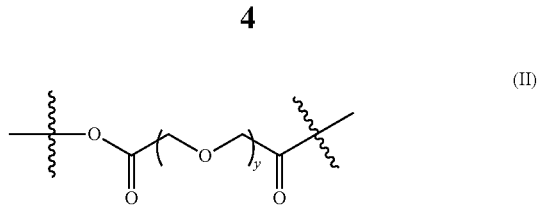

wherein y is 1 or more. In certain embodiments, y is about 1 to about 15. In certain embodiments, y is about 5 to about 15. In certain embodiments, y is about 10 to about 15. In certain embodiments, y is about 1, 2, 3, 4, 5, 6, 7, 8, 9, 10, 11, 12, 13, 14 or 15. In certain embodiments, y is about 11.

In certain embodiments, the one or more units of formula (II) have an average molecular weight of about 100 daltons to about 750 daltons. In certain embodiments, the one or more units of formula (II) have an average molecular weight of about 250 daltons to about 750 daltons. In certain embodiments, the one or more units of formula (II) have an average molecular weight of about 600 daltons.

In certain embodiments of the invention, the one or more units that comprise a group that will yield a biologically active agent upon hydrolysis of the backbone is a polyanhydride.

In certain embodiments of the invention, the polyanhydride is a poly(anhydride-ester).

In certain embodiments of the invention, the polyanhydride is a poly(anhydride-amide).

In certain embodiments, the polyanhydride comprises one or more units of formula (I) in the backbone:

$$—C(=O)R^1-A-L-A-R^1C(=O)—O— \quad (I)$$

wherein
   each $R^1$ is a group that will provide a biologically active agent upon hydrolysis of the polymer;
   each A is independently an ester or amide linkage; and
   each L is independently a linker molecule.

In certain embodiments, A is independently an ester linkage.

In certain embodiments, A is independently an amide linkage.

In certain embodiments, the polyanhydride comprises repeating units of formula (I) in the backbone.

In certain embodiments, the polyanhydride comprises a first group of one or more units of formula (I) in the backbone and a second group of one or more units of formula (I) in the backbone, wherein the L in the first group is different than the L in the second group.

In certain embodiments, the polyanhydride comprises a first group of repeating units of formula (I) in the backbone and a second group of repeating units of formula (I) in the backbone, wherein the L in the first group is different than the L in the second group.

In certain embodiments, the one or more groups that will yield a biologically active compound upon hydrolysis of the backbone has an average molecular weight of about 1,000 daltons to about 100,000 daltons. In certain embodiments, the one or more groups that will yield a biologically active compound upon hydrolysis of the backbone has an average molecular weight of about 5,000 daltons to about 100,000 daltons. In certain embodiments, the one or more groups that will yield a biologically active compound upon hydrolysis of the backbone has an average molecular weight of about 5,000 daltons to about 50,000 daltons. In certain embodiments, the one or more groups that will yield a biologically active compound upon hydrolysis of the backbone has an average molecular weight of about 10,000 daltons to about 30,000 daltons.

In certain embodiments, the biologically active agent is an antimicrobial, anti-inflammatory, antioxidant, analgesic, anticoagulant or fibrinolytic.

In certain embodiments, the biologically active agent is an anti-inflammatory agent.

In certain embodiments, the anti-inflammatory is 3-amino-4-hydroxybutyric acid, aceclofenac, alminoprofen, amfenac, bromfenac, bumadizon, carprofen, diclofenac, diflunisal, enfenamic acid, etodolac, fendosal, flufenamic acid, gentisic acid, meclofenamic acid, mefenamic acid, mesalamine, niflumic acid, olsalazine, oxaceprol, S-adenosylmethionine, salicylic acid, salsalate, sulfasalazine or tolfenamic acid.

In certain embodiments, the anti-inflammatory agent is salicylic acid.

In certain embodiments, the biologically active agent is an antimicrobial.

In certain embodiments, the antimicrobial is 2-p-sulfanilyanilinoethanol, 4-sulfanilamidosalicylic acid, acediasulfone, amoxicillin, amphotericin B, ampicillin, apalcillin, apicycline, apramycin, aspoxicillin, aztreonam, bacitracin, bambermycin(s), biapenem, carbenicillin, carumonam, cefadroxil, cefamandole, cefatrizine, cefbuperazone, cefclidin, cefdinir, cefditoren, cefepime, cefetamet, cefixime, cefmenoxime, cefminox, cefodizime, cefonicid, cefoperazone, ceforanide, cefotaxime, cefotetan, cefotiam, cefozopran, cefpimizole, cefpiramide, cefpirome, cefprozil, cefroxadine, ceftazidime, cefteram, ceftibuten, ceftriaxone, cefuzonam, cephalexin, cephaloglycin, cephalosporin C, cephradine, ciprofloxacin, clinafloxacin, cyclacillin, diathymosulfone, enoxacin, epicillin, flomoxef, grepafloxacin, hetacillin, imipenem, lomefloxacin, lucensomycin, lymecycline, meropenem, moxalactam, mupirocin, nadifloxacin, natamycin, norfloxacin, panipenem, pazufloxacin, penicillin N, pipacycline, pipemidic acid, polymyxin, quinacillin, ritipenem, rolitetracycline, salazosulfadimidine, sancycline, sparfloxacin, succisulfone, sulfachrysoidine, sulfaloxic acid, teicoplanin, temafloxacin, temocillin, tetracycline, thiostrepton, ticarcillin, tigemonam, tosufloxacin, trovafloxacin or vancomycin.

In certain embodiments, the biologically active agent is an antioxidant.

In certain embodiments, the antioxidant is vanillic acid, syringic acid, ferulic acid, sinapic acid, or p-coumaric acid.

In certain embodiments, the biologically active agent is an analgesic (e.g., salicylic acid).

In certain embodiments, the biologically active agent is an anticoagulant.

In certain embodiments, the anticoagulant is argatroban.

In certain embodiments, the biologically active agent is a fibrinolytic.

In certain embodiments, the fibrinolytic is:

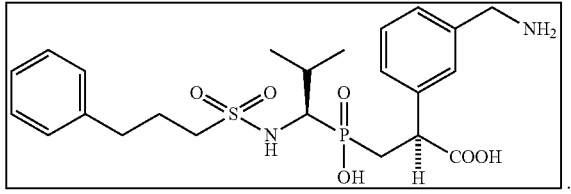 [SMILES: CC(C)[C@H](NS(=O)(=O)CCCc1ccccc1)P(=O)(O)C[C@H](C(=O)O)c1cccc(CN)c1]

In certain embodiments, the ratio of the a) one or more units that comprise a group that will yield a biologically active agent upon hydrolysis of the backbone to the b) one or more units of formula (II), ranges from between about 10:1 to about 1:10. In certain embodiments, the ratio of the a) one or more units that comprise a group that will yield a biologically active agent upon hydrolysis of the backbone to the b) one or more units of formula (II), ranges from between about 5:1 to about 1:5. In certain embodiments, the ratio of the a) one or more units that comprise a group that will yield a biologically active agent upon hydrolysis of the backbone to the b) one or more units of formula (II), ranges from between about 2:1 to about 1:2. In certain embodiments, the ratio of the a) one or more units that comprise a group that will yield a biologically active agent upon hydrolysis of the backbone to the b) one or more units of formula (II), is e.g., 5:1, 4:1, 3:1, 2:1, 1:1, 1:2, 1:3, 1:2, 1:3, 1:4 or 1:5. In certain embodiments, the ratio is 1:1 or 2:1. In certain embodiments, the ratio is less than 2:1.

Certain embodiments of the invention provide a block copolymer comprising a) a first block comprising a polyanhydride having a backbone, wherein the backbone comprises one or more units that comprise a group that will yield a biologically active agent upon hydrolysis of the backbone, and b) a second block comprising one or more units of formula (II):

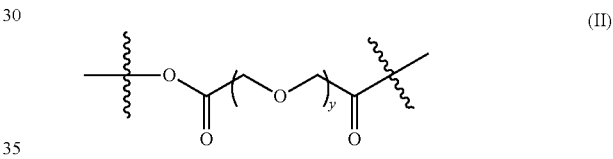

wherein y is 1 or more.

In certain embodiments, the first block comprises at least about 5 or more groups.

In certain embodiments, the second block comprises at least about 5 or more groups.

Certain embodiments of the invention provide a copolymer as described herein comprising one or more units of formula (III):

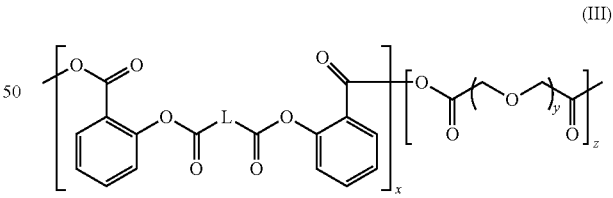

wherein each L is independently a linker molecule;
x is 5 or more;
y is 1 or more; and
z is 5 or more.

In certain embodiments, y is about 1 to about 15. In certain embodiments, y is about 5 to about 15. In certain embodiments, y is about 10 to about 15. In certain embodiments, y is about 1, 2, 3, 4, 5, 6, 7, 8, 9, 10, 11, 12, 13, 14 or 15. In certain embodiments, y is about 11.

Certain embodiments of the invention provide a copolymer as described herein comprising one or more units of formula (IV):

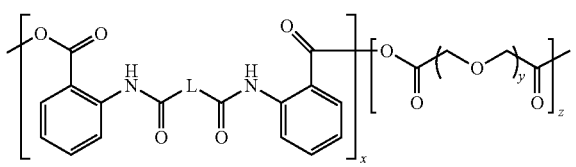

(IV)

wherein each L is independently a linker molecule;
x is 5 or more;
y is 1 or more; and
z is 5 or more.

In certain embodiments, y is about 1 to about 15. In certain embodiments, y is about 5 to about 15. In certain embodiments, y is about 10 to about 15. In certain embodiments, y is about 1, 2, 3, 4, 5, 6, 7, 8, 9, 10, 11, 12, 13, 14 or 15. In certain embodiments, y is about 11.

In certain embodiments, each linker molecule is selected from a branched aliphatic, linear aliphatic, and oxygen-containing linker molecule.

In certain embodiments, L is adipic (—$CH_2CH_2CH_2CH_2$—) or diethylmalonic (—$CH_2C(Et)_2CH_2$—).

In certain embodiments L is adipic (—$CH_2CH_2CH_2CH_2$—).

In certain embodiments, L is diethylmalonic (—$CH_2C(Et)_2CH_2$—).

In certain embodiments, L is a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—), (—NR—) or phenylene, and wherein the chain is optionally substituted on carbon with one or more (e.g. 1, 2, 3, or 4) substituents selected from the group consisting of ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo, carboxy, aryl, aryloxy, heteroaryl, and heteroaryloxy, wherein each R is independently selected from H or ($C_1$-$C_6$)alkyl.

In certain embodiments, L is a divalent, branched or unbranched, saturated or unsaturated, hydrocarbon chain, having from 1 to 25 carbon atoms, wherein the chain is optionally substituted on carbon with one or more (e.g. 1, 2, 3, or 4) substituents selected from the group consisting of ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo, carboxy, aryl, aryloxy, heteroaryl, and heteroaryloxy.

In certain embodiments, L is a peptide.

In certain embodiments, L is an amino acid.

In certain embodiments, L is a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—), (—NR—) or phenylene, wherein each R is independently selected from H or ($C_1$-$C_6$)alkyl.

In certain embodiments, L is a divalent, branched or unbranched, saturated or unsaturated, hydrocarbon chain, having from 3 to 15 carbon atoms, wherein one or more (e.g. 1, 2, 3, or 4) of the carbon atoms is optionally replaced by (—O—), (—NR—) or phenylene, and wherein the chain is optionally substituted on carbon with one or more (e.g. 1, 2, 3, or 4) substituents selected from the group consisting of ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo, carboxy, aryl, aryloxy, heteroaryl, and heteroaryloxy, wherein each R is independently selected from H or ($C_1$-$C_6$)alkyl.

In certain embodiments, L is a divalent, branched or unbranched, saturated or unsaturated, hydrocarbon chain, having from 3 to 15 carbon atoms, wherein one or more (e.g. 1, 2, 3, or 4) of the carbon atoms is optionally replaced by (—O—), (—NR—) or phenylene, wherein each R is independently selected from H or ($C_1$-$C_6$)alkyl.

In certain embodiments, L is a divalent, branched or unbranched, saturated or unsaturated, hydrocarbon chain, having from 3 to 15 carbon atoms.

In certain embodiments, L is a divalent, branched or unbranched, hydrocarbon chain, having from 3 to 15 carbon atoms.

In certain embodiments, L is a divalent hydrocarbon chain having 4 carbon atoms.

In certain embodiments, L is a divalent, branched or unbranched, hydrocarbon chain, having from 6 to 10 carbon atoms.

In certain embodiments, L is a divalent hydrocarbon chain having 7, 8, or 9 carbon atoms.

In certain embodiments, L is a divalent hydrocarbon chain having 8 carbon atoms.

In certain embodiments, L is 1,4 phenylene or 1,3 phenylene.

In certain embodiments, the copolymer as described herein and prepared in accordance with the present invention has an average molecular weight of about 1,000 daltons to about 100,000 daltons. In certain embodiments, the copolymer has an average molecular weight of about 5,000 daltons to about 100,000 daltons. In certain embodiments, the copolymer has an average molecular weight of about 5,000 daltons to about 50,000 daltons. In certain embodiments, the copolymer has an average molecular weight of about 10,000 daltons to about 30,000 daltons.

In certain embodiments, a copolymer as described herein further comprises a second biologically active agent dispersed in the matrix of the copolymer.

In certain embodiments, the second biologically active agent is the same as the biologically active agent yielded by hydrolysis of the copolymer backbone.

In certain embodiments, the second biologically active agent is different than the biologically active agent yielded by hydrolysis of the copolymer backbone.

In certain embodiments, the second biologically active agent is an antimicrobial, anti-inflammatory, antioxidant, analgesic, anticoagulant or fibrinolytic.

In certain embodiments, the second biologically active agent is an anti-inflammatory agent.

In certain embodiments, the anti-inflammatory agent is salicylic acid.

In certain embodiments, the second biologically active agent is an antioxidant.

In certain embodiments, the antioxidant is vitamin E or melatonin.

In certain embodiments, a copolymer as described herein further comprises a compound of formula (V) dispersed in the matrix of the copolymer:

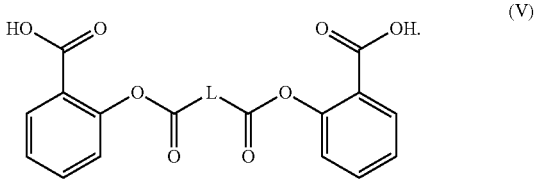

(V)

In certain embodiments, a copolymer as described herein further comprises a compound of formula (VI) dispersed in the matrix of the copolymer:

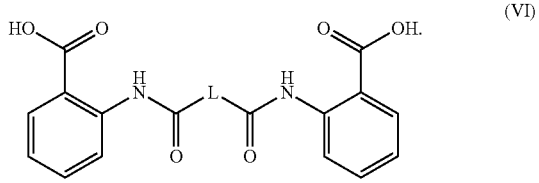

Certain embodiments of the invention provide a pharmaceutical composition comprising a copolymer as described herein and a pharmaceutically acceptable carrier.

Certain embodiments of the invention provide a medical device comprising a copolymer as described herein.

Certain embodiments of the invention provide a medical device comprising a copolymer as described herein and an adhesion barrier.

In certain embodiments, the adhesion barrier is a film, fabric or gel. In certain embodiments, the adhesion barrier is a film.

In certain embodiments, the film is Seprafilm.

In certain embodiments, the adhesion barrier is a gel.

In certain embodiments, the gel is Intercoat.

Certain embodiments of the invention provide a method of making a copolymer as described herein, comprising co-polymerizing (a) one or more monomer(s) that comprises one or more units that comprise a group that will yield a biologically active agent upon hydrolysis of the backbone; and (b) one or more monomer(s) that comprises one or more units of formula (II); under conditions to provide the polymer.

Certain embodiments of the invention provide a method of making a copolymer as described herein.

Certain embodiments of the invention provide a copolymer prepared by methods described herein.

Certain embodiments of the invention provide a therapeutic method for treating a wound in an animal comprising administering to an animal in need of such therapy, an effective amount of a copolymer or composition as described herein.

Certain embodiments of the invention provide a therapeutic method for the prevention of fibrous adhesions at a wound site in an animal comprising administering to an animal in need of such therapy, an effective amount of a copolymer or composition as described herein.

Certain embodiments of the invention provide a therapeutic method for providing localized analgesia at a wound site in an animal comprising administering to an animal in need of such therapy, an effective amount of a copolymer or composition as described herein.

Certain embodiments of the invention provide a therapeutic method for providing localized analgesia at a wound site in an animal comprising administering to an animal in need of such therapy, an effective amount of a copolymer or composition as described herein, wherein the biologically active agent is an analgesic.

In certain embodiments of the invention, the copolymer or composition is administered by injection.

Certain embodiments of the invention provide a method for promoting wound healing in an animal, comprising contacting a copolymer or composition as described herein with a wound of the animal.

Certain embodiments of the invention provide a method for the prevention of fibrous adhesions at a wound site in an animal, comprising contacting a copolymer or composition as described herein with the wound of the animal.

Certain embodiments of the invention provide a method for providing localized analgesia at a wound site in an animal, comprising contacting a copolymer or composition as described herein with the wound of the animal.

Certain embodiments of the invention provide a method for providing localized analgesia at a wound site in an animal, comprising contacting a copolymer or composition as described herein with the wound of the animal, wherein the biologically active agent is an analgesic.

Certain embodiments of the invention provide a copolymer or composition as described herein for use in medical therapy.

Certain embodiments of the invention provide for the use of a copolymer or composition as described herein for the manufacture of a medicament for the treatment of a wound in an animal, such as a human.

Certain embodiments of the invention provide for the use of a copolymer or composition as described herein for the manufacture of a medicament for the prevention of fibrous adhesions at a wound site in an animal, such as a human.

Certain embodiments of the invention provide for the use of a copolymer or composition as described herein for the manufacture of a medicament for providing localized analgesia at a wound site in an animal, such as a human.

Certain embodiments of the invention provide a copolymer or composition as described herein for use in treating a wound.

Certain embodiments of the invention provide a copolymer or composition as described herein for use in preventing fibrous adhesions at a wound site.

Certain embodiments of the invention provide a copolymer or composition as described herein for use in providing localized analgesia at a wound site.

In certain embodiments, the animal is a mammal.

In certain embodiments, the mammal is a human.

In another embodiment of the invention, an article of manufacture, or "kit", containing materials useful for the treatment of wounds, providing analgesia and/or the prevention of fibrous adhesions described above is provided. In one embodiment, the kit comprises a copolymer as described herein. In one embodiment, the kit comprises a container comprising a copolymer as described herein. In certain embodiments, the container may further comprise a desiccant. The kit may also further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, etc. The container may be formed from a variety of materials such as glass or plastic.

The invention also provides processes and intermediates disclosed herein that are useful for preparing the copolymers as described herein (see, e.g., the Examples). The intermediates described herein may have therapeutic activity, and therefore, may also be used for the treatment of a wound, the prevention of fibrous adhesions or providing localized analgesia.

Compositions Comprising a Polyanhydride and an Adhesion Barrier

Certain embodiments of the present invention provide a composition comprising 1) a polyanhydride having a backbone, wherein the backbone comprises one or more units that comprise a group that will yield a biologically active agent upon hydrolysis of the backbone; and 2) an adhesion barrier.

In certain embodiments, the biologically active agent is an antimicrobial, anti-inflammatory, antioxidant, analgesic, anticoagulant or fibrinolytic.

In certain embodiments, the biologically active agent is an anti-inflammatory agent.

In certain embodiments, the anti-inflammatory is 3-amino-4-hydroxybutyric acid, aceclofenac, alminoprofen, amfenac, bromfenac, bumadizon, carprofen, diclofenac, diflunisal, enfenamic acid, etodolac, fendosal, flufenamic acid, gentisic acid, meclofenamic acid, mefenamic acid, mesalamine, niflumic acid, olsalazine, oxaceprol, S-adenosylmethionine, salicylic acid, salsalate, sulfasalazine or tolfenamic acid.

In certain embodiments, the anti-inflammatory agent is salicylic acid.

In certain embodiments, the biologically active agent is an antimicrobial.

In certain embodiments, the antimicrobial is 2-p-sulfanilyanilinoethanol, 4-sulfanilamidosalicylic acid, acediasulfone, amoxicillin, amphotericin B, ampicillin, apalcillin, apicycline, apramycin, aspoxicillin, aztreonam, bacitracin, bambermycin(s), biapenem, carbenicillin, carumonam, cefadroxil, cefamandole, cefatrizine, cefbuperazone, cefclidin, cefdinir, cefditoren, cefepime, cefetamet, cefixime, cefmenoxime, cefminox, cefodizime, cefonicid, cefoperazone, ceforanide, cefotaxime, cefotetan, cefotiam, cefozopran, cefpimizole, cefpiramide, cefpirome, cefprozil, cefroxadine, ceftazidime, cefteram, ceftibuten, ceftriaxone, cefuzonam, cephalexin, cephaloglycin, cephalosporin C, cephradine, ciprofloxacin, clinafloxacin, cyclacillin, diathymosulfone, enoxacin, epicillin, flomoxef, grepafloxacin, hetacillin, imipenem, lomefloxacin, lucensomycin, lymecycline, meropenem, moxalactam, mupirocin, nadifloxacin, natamycin, norfloxacin, panipenem, pazufloxacin, penicillin N, pipacycline, pipemidic acid, polymyxin, quinacillin, ritipenem, rolitetracycline, salazosulfadimidine, sancycline, sparfloxacin, succisulfone, sulfachrysoidine, sulfaloxic acid, teicoplanin, temafloxacin, temocillin, tetracycline, thiostrepton, ticarcillin, tigemonam, tosufloxacin, trovafloxacin or vancomycin.

In certain embodiments, the biologically active agent is an antioxidant.

In certain embodiments, the antioxidant is vanillic acid, syringic acid, ferulic acid, sinapic acid, or p-coumaric acid.

In certain embodiments, the biologically active agent is an analgesic (e.g., salicylic acid).

In certain embodiments, the biologically active agent is an anticoagulant.

In certain embodiments, the anticoagulant is argatroban.

In certain embodiments, the biologically active agent is a fibrinolytic.

In certain embodiments, the fibrinolytic is:

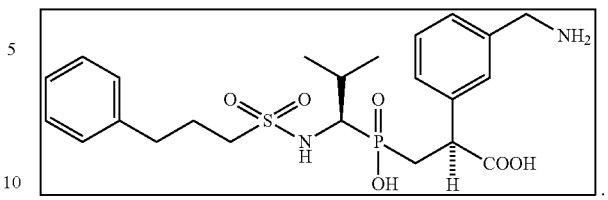

In certain embodiments, the adhesion barrier is a film, fabric, mesh, or gel.

In certain embodiments, the adhesion barrier is a film.

In certain embodiments, the film is Seprafilm.

In certain embodiments, the adhesion barrier is a gel.

In certain embodiments, the gel is Intercoat.

In certain embodiments, the polyanhydride comprises one or more units of formula (I) in the backbone:

$$-C(=O)R^1-A-L-A-R^1C(=O)-O- \qquad (I)$$

wherein
each $R^1$ is a group that will provide a biologically active agent upon hydrolysis of the polymer;
each A is independently an ester or an amide linkage; and
each L is independently a linker molecule.

In certain embodiments, A is independently an ester linkage.

In certain embodiments, A is independently an amide linkage.

In certain embodiments each linker molecule is selected from a branched aliphatic, linear aliphatic, and oxygen-containing linker molecule.

In certain embodiments, L is adipic ($-CH_2CH_2CH_2CH_2-$) or diethylmalonic ($-CH_2C(Et)_2CH_2-$).

In certain embodiments L is adipic ($-CH_2CH_2CH_2CH_2-$).

In certain embodiments, L is diethylmalonic ($-CH_2C(Et)_2CH_2-$).

In certain embodiments, L is a divalent, branched or unbranched, saturated or unsaturated, hydrocarbon chain, having from 1 to 25 carbon atoms, wherein one or more (e.g. 1, 2, 3, or 4) of the carbon atoms is optionally replaced by ($-O-$), ($-NR-$) or phenylene, and wherein the chain is optionally substituted on carbon with one or more (e.g. 1, 2, 3, or 4) substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy, wherein each R is independently selected from H or $(C_1-C_6)$alkyl.

In certain embodiments, L is a divalent, branched or unbranched, saturated or unsaturated, hydrocarbon chain, having from 1 to 25 carbon atoms, wherein the chain is optionally substituted on carbon with one or more (e.g. 1, 2, 3, or 4) substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy.

In certain embodiments, L is a peptide.

In certain embodiments, L is an amino acid.

In certain embodiments, L is a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—), (—NR—) or phenylene, wherein each R is independently selected from H or (C$_1$-C$_6$)alkyl.

In certain embodiments, L is a divalent, branched or unbranched, saturated or unsaturated, hydrocarbon chain, having from 3 to 15 carbon atoms, wherein one or more (e.g. 1, 2, 3, or 4) of the carbon atoms is optionally replaced by (—O—), (—NR—) or phenylene, and wherein the chain is optionally substituted on carbon with one or more (e.g. 1, 2, 3, or 4) substituents selected from the group consisting of (C$_1$-C$_6$)alkoxy, (C$_3$-C$_6$)cycloalkyl, (C$_1$-C$_6$)alkanoyl, (C$_1$-C$_6$)alkanoyloxy, (C$_1$-C$_6$)alkoxycarbonyl, (C$_1$-C$_6$)alkylthio, azido, cyano, nitro, halo, hydroxy, oxo, carboxy, aryl, aryloxy, heteroaryl, and heteroaryloxy, wherein each R is independently selected from H or (C$_1$-C$_6$)alkyl.

In certain embodiments, L is a divalent, branched or unbranched, saturated or unsaturated, hydrocarbon chain, having from 3 to 15 carbon atoms, wherein one or more (e.g. 1, 2, 3, or 4) of the carbon atoms is optionally replaced by (—O—), (—NR—) or phenylene, wherein each R is independently selected from H or (C$_1$-C$_6$)alkyl.

In certain embodiments, L is a divalent, branched or unbranched, saturated or unsaturated, hydrocarbon chain, having from 3 to 15 carbon atoms.

In certain embodiments, L is a divalent, branched or unbranched, hydrocarbon chain, having from 3 to 15 carbon atoms.

In certain embodiments, L is a divalent hydrocarbon chain having 4 carbon atoms.

In certain embodiments, L is a divalent, branched or unbranched, hydrocarbon chain, having from 6 to 10 carbon atoms.

In certain embodiments, L is a divalent hydrocarbon chain having 7, 8, or 9 carbon atoms.

In certain embodiments, L is a divalent hydrocarbon chain having 8 carbon atoms.

In certain embodiments, L is 1,4 phenylene or 1,3 phenylene.

In certain embodiments, the polyanhydride comprises repeating units of formula (I) in the backbone.

In certain embodiments, polyanhydride comprises one or more units of formula (Ia) in the backbone:

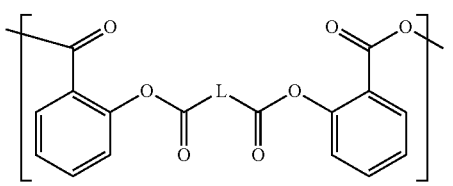

(Ia)

wherein L is a linker molecule.

In certain embodiments, the polyanhydride comprises repeating units of formula (Ia) in the backbone.

In certain embodiments, polyanhydride comprises one or more units of formula (Ib) in the backbone:

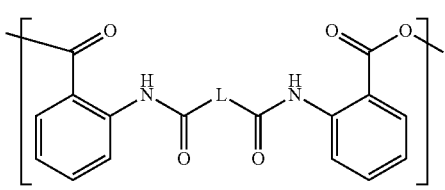

(Ib)

wherein L is a linker molecule.

In certain embodiments, the polyanhydride comprises repeating units of formula (Ib) in the backbone.

In certain embodiments, the polyanhydride as described herein further comprises a second biologically active agent dispersed in the matrix of the polymer.

In certain embodiments, the second biologically active agent is the same as the biologically active agent yielded by hydrolysis of the polyanhydride backbone.

In certain embodiments, the second biologically active agent is different than the biologically active agent yielded by hydrolysis of the polyanhydride backbone.

In certain embodiments, the second biologically active agent is an antimicrobial, anti-inflammatory, antioxidant, analgesic, anticoagulant or fibrinolytic.

In certain embodiments, the second biologically active agent is an anti-inflammatory agent.

In certain embodiments, the anti-inflammatory agent is salicylic acid.

In certain embodiments, the second biologically active agent is an antioxidant.

In certain embodiments, the antioxidant is vitamin E or melatonin.

In certain embodiments, the polyanhydride as described herein further comprises a compound of formula (V) dispersed in the matrix of the polymer:

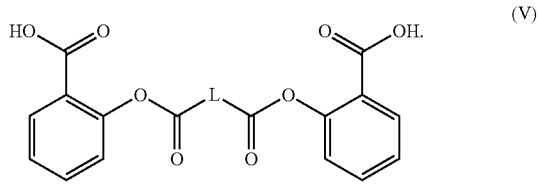

(V)

In certain embodiments, a polymer as described herein further comprises a compound of formula (VI) dispersed in the matrix of the polymer:

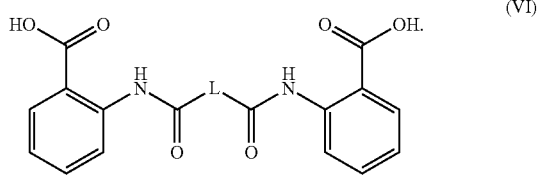

(VI)

In certain embodiments, the polyanhydride is blended with a second polymer to generate a polymer blend.

In certain embodiments, the second polymer is polyethylene glycol (PEG), poly(lactic-co-glycolic acid) (PLGA) or poly(vinyl pyrrolidone) (PVP).

In certain embodiments, the second polymer is PEG.

In certain embodiments, the second polymer is PLGA.

In certain embodiments, the second polymer is PVP.

In certain embodiments, the second polymer is a blend of PEG and PLGA.

In certain embodiments, the polymer blend is electrospun to generate electrospun nanofibers.

In certain embodiments, the electrospun nanofibers are associated with the adhesion barrier. In certain embodiments, the electrospun nanofibers may associated with the adhesion barrier using water or dimethylsulfoxide (DMSO).

In certain embodiments, the polymer is formulated into microspheres.

In certain embodiments, the microspheres are admixed with the adhesion barrier.

Certain embodiments of the invention provide a medical device comprising a composition as described herein.

Definitions

Unless otherwise described: halo is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic. Heteroaryl encompasses a radical of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heterocycle of about eight to ten ring atoms comprising one to four heteroatoms each selected from the group consisting of non-peroxide oxygen, sulfur, and N(X).

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenyl-alanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a $(C_1-C_6)$alkyl, phenyl or benzyl ester or amide; or as an α-methylbenzyl amide). Other suitable amino and carboxy protecting groups are known to those skilled in the art (See for example, T. W. Greene, *Protecting Groups In Organic Synthesis*; Wiley: New York, 1981, and references cited therein). An amino acid can be linked to the remainder of a compound of formula I through the carboxy terminus, the amino terminus, or through any other convenient point of attachment, such as, for example, through the sulfur of cysteine.

Specific values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

As used herein, the phrases "dispersed in the matrix of the copolymer" and "dispersed in the matrix of the polymer" mean that an agent, such as an anti-inflammatory agent, is located within the matrix of a copolymer/polymer such that it can be released in a controlled fashion when placed within the body. Preferably, the copolymer/polymer matrix comprises a bio-degradable polymer.

As used herein, "release" of an agent refers to delivery of an agent in a form that is bioavailable. For instance, the term "release" includes degradation of a copolymer/polymer in which the agent is incorporated in the copolymer/polymer backbone, or appended to the copolymer/polymer backbone, to release free agent. The term also includes degradation of a copolymer/polymer that entraps molecules of the agent in the matrix of the copolymer/polymer, thereby allowing the free agent to make direct contact with the surrounding tissue or bone. The term "release" also encompasses administration of an agent in a form that is immediately bioavailable (i.e., not a sustained release formulation).

As used herein, the terms "treat" and "treatment" can refer to therapeutic treatment or to prophylactic or preventative treatment, wherein the object is to prevent or decrease an undesired physiological change or disorder, for example, such as undesired physiological changes or disorders associated with wounds (e.g., fibrous adhesions, inflammation, pain, etc.).

As used herein the phrase "fibrous adhesions" refers to bands of fibrous tissue that join two surfaces in the body that are not normally connected. They generally form after injury to an area that results in increased inflammation. Surgery, trauma, infections, radiation, and ischemia can all lead to adhesion formation, with surgery being the most common cause. Fibrinous bands, which are precursors to fibrous adhesions, are also encompassed by this phrase.

As described herein, the phrase "adhesion barrier" refers to a material that can be used to reduce deleterious internal scarring (e.g., adhesions) following injury (e.g., surgery) by separating adjacent surfaces of tissues and organs during healing. In certain embodiments, the adhesion barrier is a film, fabric or gel. In certain embodiments, the adhesion barrier is a barrier listed in Table 2. In certain embodiments, the adhesion barrier is Seprafilm. In certain embodiments, the adhesion barrier is Intercoat.

As used herein, the term "wound" refers to an injury to a part or tissue of the body, especially one caused by physical trauma and characterized by tearing, cutting, piercing, or breaking of the tissue.

In certain embodiments, a polymer as described herein may be administered "at a wound site" or by "contacting" a polymer with the wound. As used herein, these phrases/terms may mean locally administering the polymer so that it is in direct contact with the wound; or locally administering the polymer to a location proximal to the wound, so that the polymer can produce the desired or stated therapeutic effect (e.g. prevention of fibrous adhesions, provision of localized analgesia, etc.), at the site.

Formulations

The copolymers/polymers, microspheres and electrospun nanofibers described herein can be formulated as pharmaceutical compositions and administered to a mammalian host, such as a human patient in a variety of forms adapted to the chosen route of administration, i.e., parenterally, by intravenous, intramuscular, topical or subcutaneous routes.

The present copolymers/polymers or microspheres may be administered intravenously or intraperitoneally by infusion or injection.

The pharmaceutical dosage forms suitable for injection or infusion can include sterile aqueous solutions or dispersions or sterile powders comprising the present copolymers/polymers or microspheres that are adapted for the extemporaneous preparation of sterile injectable or infusible solutions or dispersions.

For topical administration, the present copolymers/polymers may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present copolymers/polymers or microspheres can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Useful dosages of the present copolymers/polymers, microspheres and electrospun nanofibers can be determined by comparing their in vitro activity, and in vivo activity in animal models. Methods for the extrapolation of effective dosages in mice, and other animals, to humans are known to the art; for example, see U.S. Pat. No. 4,938,949.

The amount of the present copolymers/polymers, microspheres or electrospun nanofibers required for use in treatment will vary with the route of administration, the nature of the condition being treated and the age and condition of the patient and will be ultimately at the discretion of the attendant physician or clinician. However, in one embodiment a suitable dose may be in the range of from about 0.05 to about 100 mg/kg, e.g., from about 1 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

In one embodiment, the invention provides a composition comprising the present copolymers/polymers formulated in such a unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The invention will now be illustrated by the following non-limiting Examples.

Example 1

Fibrous adhesions are a common result of surgery that can lead to chronic pain, infertility, and intestinal obstruction. Available devices have been designed to act as barriers to adhesion formation, but are not extensively used. Although they have been shown to reduce adhesion formation and severity, the devices do not significantly reduce complications resulting from adhesions. As described herein is the enhancement of commercially available devices by using salicylic acid (SA)-based poly(anhydride-esters) (PAEs) that hydrolytically degrade to release salicylic acid and physically admixed antioxidants at a controlled rate to potentially reduce adhesion formation both physically and chemically.

Mechanical, surface, and thermal analyses, as well as in vitro drug release assays and cytotoxicity studies will be used to optimize potential devices. Optimized devices will be evaluated in vivo for adhesion reduction efficacy and compared to the original, commercially available devices. Efficacy will be determined by the extent of adhesion formation in a rat model.

Section 1.

Fibrous adhesions are a serious complication that can arise from trauma to the body as they can lead to chronic pain, infertility, and intestinal obstruction. Adhesions are bands of fibrous tissue that join two surfaces in the body which are not normally connected. They generally form after injury to an area that results in increased inflammation. Surgery, trauma, infections, radiation, and ischemia can all lead to adhesion formation, with surgery being the most common cause.

There are many different organs in the abdominal area that can be affected by adhesions; therefore, the need to prevent adhesion formation here is important. Table 1 lists the anatomical sites and organs that were most commonly found to have adhesions associated with them, and the percentage of abdominal laparoscopy patients exhibiting adhesions on those organs after surgery.

TABLE 1

| Adhesion Site Frequency to Anatomical Sites of Abdominal Laparoscopy Patients | |
|---|---|
| Adhesion site | % Adhered |
| Trocar Scar | 71 |
| Omentum | 68 |
| Small Bowel | 67 |
| Abdominal Wall | 45 |
| Colon | 41 |
| Liver | 34 |
| Female Reproductive Organs | 23 |
| Stomach | 20 |
| Spleen | 9 |

The physiological pathway that leads to abdominal adhesion formation has been well studied. After surgery, fibrinogen from the blood leaks into the peritoneal cavity and forms a fibrin matrix. This matrix forms into transient fibrinous bands that are either broken down by fibrinolysis or used as a scaffold for fibroblasts to create permanent fibrous adhesions. The occurrence of fibrinolysis is dependent upon the levels of different cytokines and enzymes (FIG. 1). Mesothelial cells of the injured peritoneum release cytokines to recruit immune cells and fibroblasts. Polymorphonuclear neutrophils are the first cells to appear. Macrophages are recruited to the site around day 2 after surgery. Mesothelial cells start to proliferate and begin forming new peritoneum on day 3. The peritoneum regrows from mesothelial cells floating freely in the peritoneal fluid and is therefore repaired from many areas at once rather than needing to have cells migrate into the damaged area from the undamaged edges. It is because of this that the peritoneum is repaired in 7-10 days regardless of whether the injury to the area is moderate or severe.

Fibrous adhesions have an enormous impact on the healthcare system. It has been estimated that 95% of abdominal and pelvic surgeries, including gynecologic, result in adhesions. Adhesion related problems account for 6% of all hospital readmissions and 1% of all hospitalizations in the United States. A comprehensive study in Scotland found that 22% of patients who had abdominal surgery were readmitted within a year, and 34.6% are readmitted within 10 years for an average of 2.1 times. In 1994, $1.3 billion was spent on hospital costs for 446,000 abdominal adhesiolysis procedures, a surgery to dissect fibrous adhesions. While adhesiolysis can help alleviate some pain and complications associated with adhesions, the effect is often temporary as the adhesions tend to grow back after the procedure. The statistics on the number of secondary surgeries needed due to adhesions are even more alarming when one takes into account that the presence of adhesions makes such secondary surgeries even more difficult and dangerous. Adhesions increase surgery time, hospital stay, complications, blood loss, morbidity, and mortality; they are the main reason for an otherwise minimally invasive planned laparoscopy procedure to be switched to an invasive laparotomy procedure. Adhesions are responsible for the majority of trocar-related injuries. They also greatly increase the chance of inadvertent enterotomy, cutting of the intestines, with 19% of reoperations of the abdomen resulting in inadvertent enterotomies. This results in more postoperative complications, more urgent laparotomies, higher admission rate to the ICU, and longer hospital stays; if left undetected an inadvertent enterotomy can lead to death. One of the most problematic consequences of adhesion formation is small bowel obstruction (SBO). Studies estimate that 74% of SBOs are caused by adhesions. Simple obstructions result in 3-5% patient mortality; the mortality rate rises to 30% if the bowel becomes strangulated, necrotic, or perforated. If left untreated, SBOs will lead to fatal peritonitis. In total, 2100-2400 patients die from intestinal adhesions with bowel obstructions annually in the U.S. While there has been some improvement in devices to reduce adhesion formation, no device has been proven to significantly reduce the incidence of SBOs caused by adhesions.

In addition to improved surgical techniques, both pharmaceuticals and physical barriers have been explored as means to prevent adhesion formation (Tingstedt et al., Eur Surg Res 39, 259-268 (2007); Ward, et al., Journal of Surgical Research, 165(1), 91-111 (2009)). Drugs tested for the prevention of adhesion growth are those that affect the clotting cascade, the inflammatory process, cell proliferation, extracellular matrix production, or oxidative stress. Systemic administration of such drugs at therapeutic levels can cause undesired side effects and delay healing after surgery. There have been some attempts to inject the drugs into the peritoneal cavity; however, most of these have shown little to no efficacy in laboratory testing primarily due to the tendency for drugs placed in the peritoneal cavity to be quickly absorbed by the mesothelium and subsequently distributed throughout the body.

Various solids, gels, and fluids have been used as physical barriers. The main purpose of every barrier is to separate surfaces that adhesions could potentially form between. The FDA has approved only 5 barrier devices for human use. None of the devices have been shown efficacious enough at reducing adhesion formation to warrant their ubiquitous use. Based on the number of surgeries in which adhesion barriers would be warranted and the number of barriers sold, barriers are used in at best a little over 5% of abdominal surgeries. The efficacy of these devices must be higher if they are to be used more often.

There is a need for a more efficacious device for the prevention of fibrous adhesions. Accordingly, as described herein is a biodegradable device that can provide a physical barrier as well as deliver sustained release of anti-inflammatory and antioxidant drugs directly to the desired area as a pharmaceutical treatment. This controlled sustained release of drugs may be accomplished through the use of salicylic acid (SA)-based poly(anhydride esters) (PAE).

Section 2.

2.1. The Determination of the Composition, Formulation, and Amount of SA-Based PAE that Gives the Most Optimal Drug Release Profile for Adhesion Prevention and the Determination of how Best to Incorporate the PAEs into Adhesion Barriers Currently on the Market.

The current resorbable adhesion barrier devices on the market have shown only moderate efficacy in patients. Two of these devices, Seprafilm and Intercoat, are used in experiments described below; however, other adhesion barriers could also be used. Seprafilm (Genzyme Corp.), composed of hyaluronic acid and carboxymethylcellulose, can only be used in open surgeries as it is manufactured as a film that is placed on the most traumatized area within the abdomen. Intercoat (Johnson & Johnson), composed of polyethylene glycol (PEG) and carboxymethylcellulose, is an injectable gel that can be used in either open or laparoscopic surgeries.

The use of a SA-based PAE, or polyAspirin (PA), will allow for sustained release of salicylic acid at the site of implantation as the anhydride and ester bonds are hydrolytically labile and the polymer will degrade to release salicylic acid and biocompatible diacids (Prudencio, et al., Macromolecules 38, 6895-6901 (2005); Erdmann, et al., Biomaterials 21, 1941-1946 (2000); Whitaker-Brothers, et al., Journal of Biomedical Materials Research. Part A. 76, 470-479 (2006)). Salicylic acid, the prototypical non-steroidal anti-inflammatory drug (NSAID), is a desirable agent for this application as it not only has anti-inflammatory properties, but also acts as an anticoagulant and an analgesic.

A method to optimally integrate PA with these current devices will need to be determined. The type of device will dictate the formulation of the PA. Ensuring that the form of the PA has the necessary physical properties for each device is important. Initially, PA microspheres are proposed for admixture with Intercoat and PA containing electrospun membranes are proposed for layering with Seprafilm.

The degradation rates of the polymers are critical to the efficacy of these devices. Enough SA (e.g., corresponding to about 40-100 mg/day dosage) needs to be released from the device within the first week of implantation to affect the growth of fibrous adhesions (Muzii, L. et al., Human Reproduction 13, 1486-1489 (1998); Buerke, et al., American Heart Journal 130, 465-472 (1995)). However, if too much SA (e.g., corresponding to about 1700 mg/day) is released it can result no adhesion reduction and interfere with the wound healing process responsible for closing any incisions caused by surgery (Muzii, L. et al., Human Reproduction 13, 1486-1489 (1998); Golan, et al., Human Reproduction 10, 1797-1800 (1995)). One of the FDA guidelines for resorbable adhesion barriers is that they not reduce tissue-holding strength after sutures are removed. To ensure a beneficial amount of SA is being released at all times, the optimal chemical composition and amount of PA will need to be determined such that the rate of SA release maintains a steady concentration that results in the effective range as described above. Admixtures of SA and SA-based diacids in the PA will also be considered as a means of manipulating the SA release profile. The optimal composition and amount of the PA needed will be determined separately for both the film and the gel as the shape of the PA in the device and the composition of the hydrogel will both affect the degradation of the polymer and the release of the SA.

2.2. The Incorporation of an Antioxidant into the SA-Based PAE and Determination of the Release Profile of the Antioxidant and its Effect on Polymer Degradation.

There have been numerous studies to evaluate the efficacy of different drugs on adhesion prevention, however few have been shown to be effective. To create a synergistic effect to better reduce the incidence of adhesion formation, two drugs, an anti-inflammatory and an antioxidant, are incorporated into the barriers as described herein.

Two antioxidants have been widely researched for their ability to prevent adhesions: Vitamin E and melatonin. Both have been shown to significantly reduce abdominal adhesion formation in rats when injected intraperitoneally (IP) (de la Portilla, F. et al. Diseases of the Colon & Rectum 42, 2157-2161 (2004); Imai, et al., European Journal of Obstetrics & Gynecology and Reproductive Biology 149, 131-135 (2010)).

2.3. The Determination of the Effects of Common Sterilization Techniques on the Devices and Comparison of the Efficacy of the Combination Devices Against their Equivalent Non-PolyAspirin Device In Vivo.

All medical devices need to be sterilized before implantation. Common sterilization techniques can alter the polymer in undesirable ways. It is proposed that once the final device compositions are determined, the devices be subjected to two common sterilization methods, namely electron beam and gamma ray radiation sterilization (at various dosing levels), to determine if any critical characteristics such as the degradation rate or mechanical properties of the devices are altered by the sterilization processes. If it is discovered that the degradation of the device is affected, the composition of the polymer will be changed to ensure that the desired release profile is obtained from the device after sterilization.

To achieve market approval for a medical device in the United States, it is necessary to show that the new device is both safe and efficacious. The new device must be at least as efficacious as other similar products on the market. The optimized devices will need to be tested in vivo to determine if the addition of polyAspirin has improved the efficacy of the original devices. Such testing will be initiated in a rat model. The surgery model consists of a ventral incision and intentional trauma to the peritoneum to induce a wound healing response to promote adhesion formation at the trauma site (Rajab, et al. Journal of Surgical Research 161, 246-249 (2010)). The rats will be divided into groups that will be treated with Seprafilm, Intercoat, Seprafilm+PA, Intercoat+PA, Seprafilm+PA+antioxidant, Intercoat+PA+antioxidant, or no barrier. The rats will be sacrificed at 14 days after surgery. An investigator blinded to the treatment group will grade the extent of adhesions.

Section 3.

3.1. Polyanhydrides

Polyanhydrides are a class of hydrolytically degradable polymers that have been widely used in several biomedical applications. Polyanhydrides are primarily surface eroding, a characteristic that makes them desirable for drug delivery applications as this leads to a near zero order release of molecules encapsulated within the polymer matrix (Whitaker-Brothers, et al., Journal of Biomedical Materials Research. Part A. 76, 470-479 (2006)).

3.1.1. Salicylic Acid-Based Poly(Anhydride Esters)

A series of SA-based PAEs (polyAspirins) that are composed of salicylic acid and various biocompatible diacid linker molecules have been developed (Prudencio, et al., Macromolecules 38, 6895-6901 (2005); Schmeltzer, et al., Polymer Bulletin 49, 441-448 (2003); Schmeltzer, et al., Journal of Biomaterials Science: Polymer Edition 19, 1295-1306 (2008); Carbone, et al., Macromolecular Rapid Communications 30, 1021 (2009)). These polymers exhibit hydrolytic surface erosion degradation to release free salicylic acid and biocompatible linker molecules (Scheme 1) (Erdmann, et al., Biomaterials 21, 1941-1946 (2000)). The linker can be used to alter the degradation rate of the polymer. SA-based polymers with more hydrophobic linker molecules exhibit decreased degradation rates (Prudencio, et al., Macromolecules 38, 6895-6901 (2005)).

Scheme 1. Synthesis and degradation of polyAspirin. In certain embodiments, other additional linker molecules (shown above as "R", but also descibed herein as "L") may also be used as described herein. Additionally, while salicylic acid is shown in this scheme other biologically active agents, as described herein, may also be used in other embodiments.

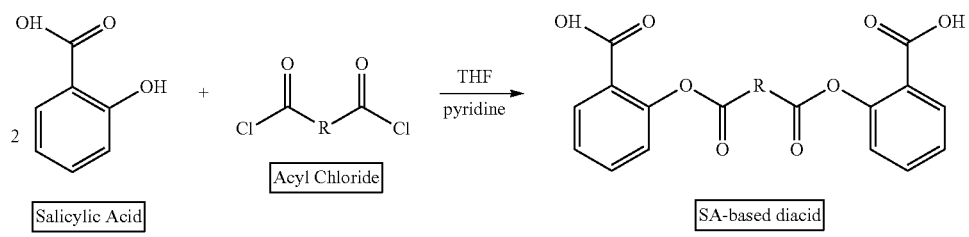

-continued

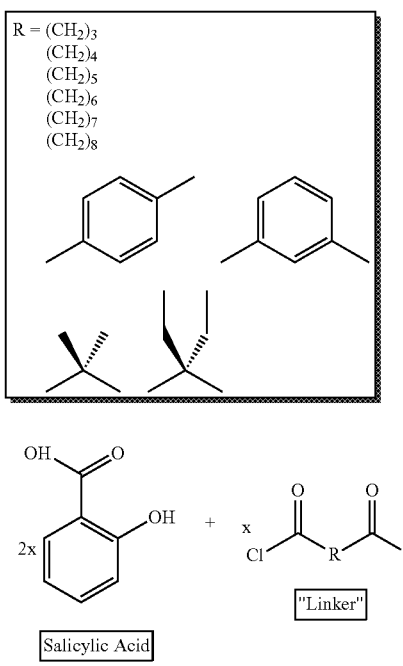
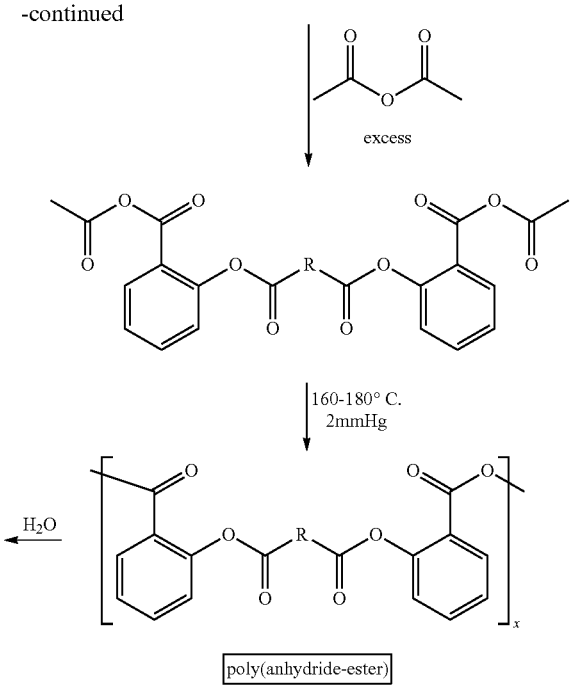

The advantage of incorporating a drug into the polymer backbone, as opposed to merely physically mixing the drug into a polymer that does not degrade into a bioactive molecule is the high drug loading achieved with this method. The inherent drug loading of PA can be up to 75% depending on the linker molecule, with the ability to have higher drug loading via admixed free drugs. Polymer systems with physically incorporated drugs cannot attain such a high drug loading without affecting the polymer degradation and drug release rates. The thermal and mechanical properties of PA allows it to be manipulated into various shapes such as, disks, films, microspheres, and fibers. The release profile of salicylic acid from PA is observed to have a lag period of little to no drug release followed by zero order release. The length of the lag period is determined by the composition of the polymer (Prudencio et al., Macromolecules 38, 6895-6901 (2005); Erdmann, et al., Biomaterials 21, 1941-1946 (2000); Yeagy, et al., Journal of Microencapsulation 23, 643-653 (2006)).

3.1.3. Admixtures of Free Drugs into PolyAspirin

Free drug molecules can be admixed into PA such that the free drug is released along with the SA from the polymer backbone. The release of free antimicrobials admixed into adipic-PA disks has been studied in vitro by placing the disks into phosphate buffered saline (PBS) pH 7.4 in an incubator shaker at 37° C. and 65 rpm. PBS was collected and replaced at various time points and analyzed by high-pressure liquid chromatography (HPLC) to determine the concentration of both salicylic acid and the antimicrobial. It was observed that the rate of antimicrobial release was dependent upon the hydrophobicity of the antimicrobial; hydrophobic antimicrobials were released at a slower rate than more hydrophilic antimicrobials. The hydrophobicity of the antimicrobial did not significantly affect the release of salicylic acid from the disks (Johnson, et al., Journal of Biomedical Materials Research. Part A. 91, 671-678 (2009)).

SA and SA-based diacids were admixed into both fast and slow degrading PA to observe the effect they would have on the lag period in the release curve of the polymers. PA with adipic acid and diethylmalonic acid as the linkers were chosen as the fast and slow degrading polymers, respectively. SA, SA-based diacids with linkers corresponding to their respective polymer, and a 1:1 mixture of SA and diacid were admixed into the polymers at 1, 5, and 10 weight percentages. Approximately 160 mg of polymer admixtures were placed in a 13 mm diameter mold and pressed for 10 minutes at 10,000 psi. This resulted in disks ~1 mm thick. All samples were made in triplicate. The disks were placed in glass vials with 10 ml PBS pH 7.4 incubated at 37° C. PBS was collected and replaced at set time points and analyzed by UV absorbance at 303 nm. SA concentration was quantified by comparing absorbance values to a calibration curve of absorbance values for SA solutions of known concentrations.

Figure 2A:
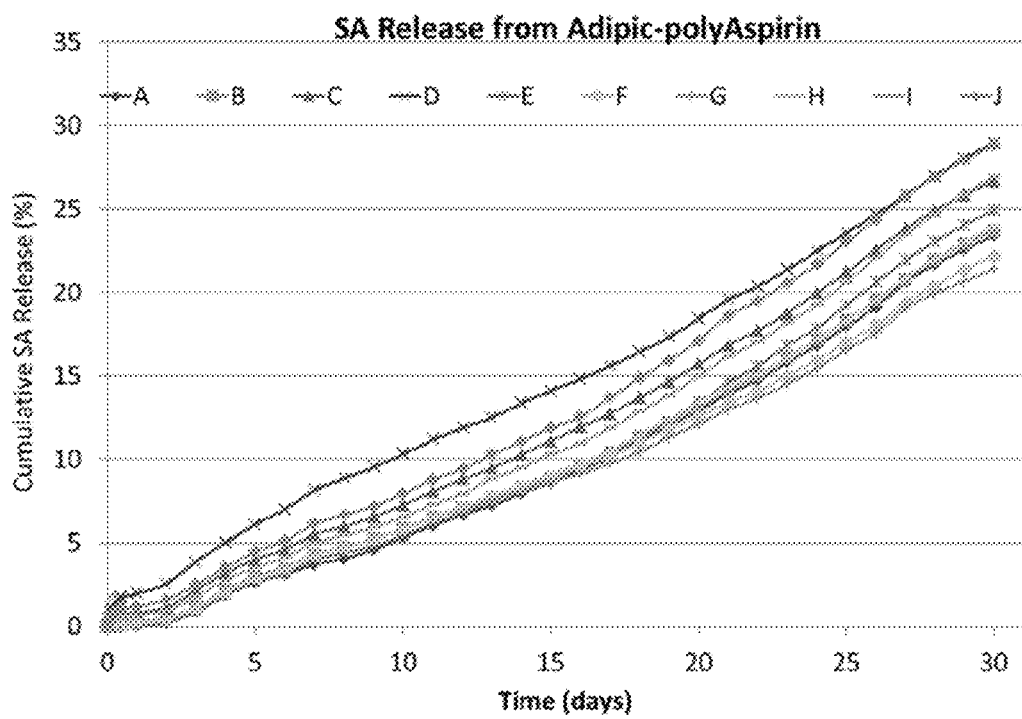
FIGS. 2A-B. Cumulative release of SA from (FIG. 2A) adipic-PA and (FIG. 2B) diethylmalonic-PA samples with admixtures (all percentages are w/w): (A) polymer alone, (B) 1% SA, (C) 5% SA, (D) 10% SA, (E) 1% diacid, (F) 5% diacid, (G) 10% diacid, (H) 1% 1:1 SA/diacid, (I) 5% 1:1 SA/diacid, (J) 10% 1:1 SA/diacid.
Figure 2B:
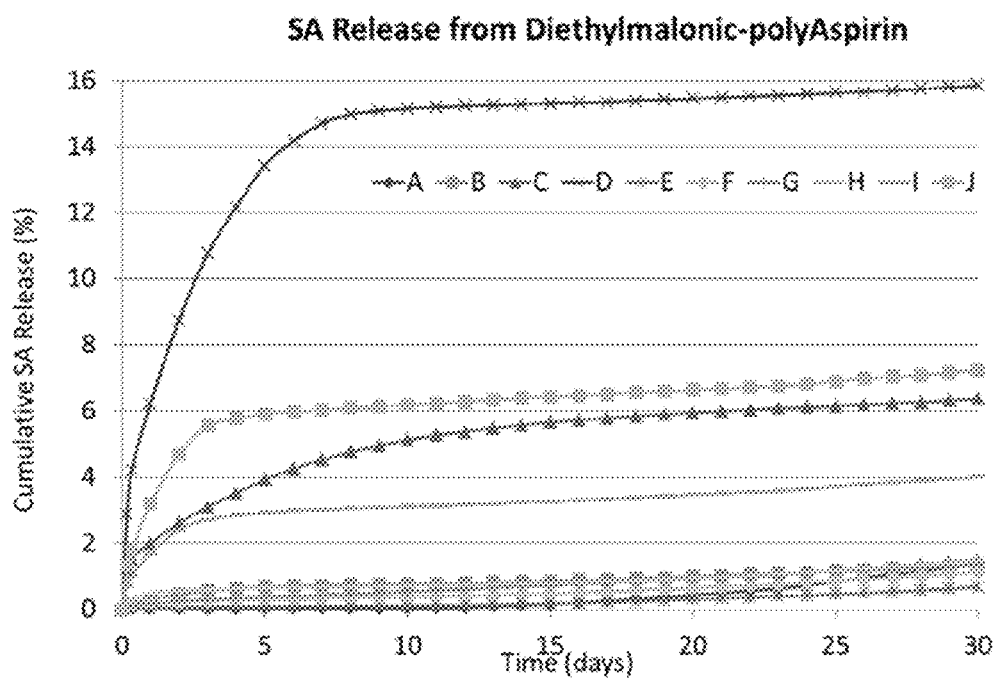

The cumulative SA release profiles of the samples are presented in FIG. 2A-B. The free SA and diacids removed the lag period of SA release observed in both of the polymer systems. The SA admixtures resulted in a burst release, where a relatively large amount of SA was released in the early time points. The size of the burst effect correlated with the weight percent of admixed SA in the system. The diacid admixtures increased early SA release from the systems, but did so with a less prominent burst profile. As expected, the 1:1 mixtures of SA and diacid had an intermediate effect between the two described above. The admixtures did not increase the degradation rate of the polymers.

The ability to negate the early lag time of SA release from PA is important for the proposed adhesion barriers, as fibrin deposition occurs immediately following surgery and fibrinolysis should occur within 3 days of surgery to mimic a proper healing response that does not lead to adhesion formation.

3.1.4. Cytotoxicity Studies

In vitro studies have been performed to assess the cytotoxicity of PAs. Briefly, L929 fibroblast cells were seeded at approximately 2000 cells/well in 3×96 well culture dishes.

A fourth 96 well plate is plated with triplicates of wells plated at different cell seeding densities. Triplicates of wells in each dish contained normal cell culture media, media with 0.10 mg/ml and 0.01 mg/ml of polymer dissolved in dimethyl sulfoxide (DMSO), and controls of media with DMSO without polymer. After 24 hours, the 96 well dish with the different original cell seeding densities is assessed using an MTS assay, which reacts with NADPH and NADH produced in living cells, to indirectly measure the number of living cells in a culture (Saed, et al., Fertility and Sterility 79, 164-168 (2003)). The MTS assay of the first dish is used to create a calibration curve that will later be used to determine the number of living cells present in the other plates. At 48, 72, and 96 hours, the other plates are assessed by MTS assay. Light microscopy is used to observe any changes in cell morphology due to PA. Previous studies have shown PA to be biocompatible at up to 0.1 mg/ml concentrations (Griffin, et al., Journal of Biomedical Materials Research. Part A. 97(3), 230-242 (2011)).

3.2. Electrospun Polymer Fibers

Electrospinning is a method to create nano to micro-sized polymeric fibers (Demir, et al., Polymer 43, 3303-3309 (2002)). The process involves creating an electric field between a charged needle and a grounded collection surface. The polymer is dissolved in a solvent and slowly ejected out of the needle where electrostatic forces overcome surface tension to cause a stream of polymer to move from the needle to the collection surface to form a mat of fibers (Griffin, et al., Journal of Biomedical Materials Research. Part A. 97(3), 230-242 (2011)).

Electrospun membranes have been tested previously for their ability to prevent adhesions. Zong, et al created electrospun poly(lactic-co-glycolic acid) (PLGA) membranes and studied their ability to prevent abdominal adhesions in rats. PLGA membranes alone decreased adhesion formation, but not significantly. Membranes of PLGA and a poly(lactic acid) (PLA)-PEG copolymer did show a significant decrease in adhesions (Zong, X. et al. Annals of Surgery 240, 910-915 (2004)). The use of PEG and PLA as electrospun membranes was further demonstrated by Yang, et al. They created PEG:PLA block copolymers of differing ratios (Yang, et al., Journal of Biomedical Materials Research. Part A. 82, 680-688 (2007)). In vitro studies demonstrated that membranes with higher PEG:PLA ratios exhibited decreased cell adhesion to the membrane (Yang, et al., Acta Biomaterialia 5, 2467-2474 (2009)). In vivo studies conducted with these membranes resulted in a significant decrease of adhesion formation when a PLA membrane was implanted as opposed to untreated controls but that a PEG:PLA membrane reduced adhesion significantly more than the PLA membrane.

Figure 3:
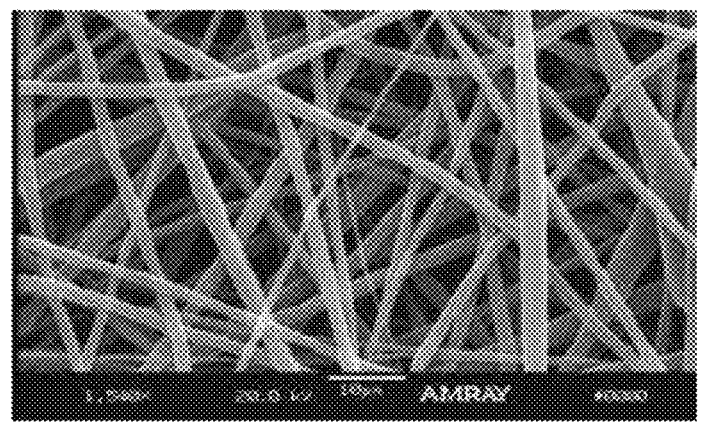
FIG. 3. Scanning electron microscopy (SEM) image of 2:1 PLGA/adipic-PA electrospun membrane.

PAs, blended with higher molecular weight PLGA or poly(vinyl pyrrolidone), have been used to create electrospun membranes (see, e.g., FIG. 3) (Griffin, et al., Journal of Biomedical Materials Research. Part A. 97(3), 230-242 (2011)). The PA-containing membranes are thin and tear easily. This is why it is proposed that the electrospun membranes be adhered to Seprafilm, to ensure that the membrane remains intact during and after implantation.

3.3. Microsphere Fabrication

Figure 4:
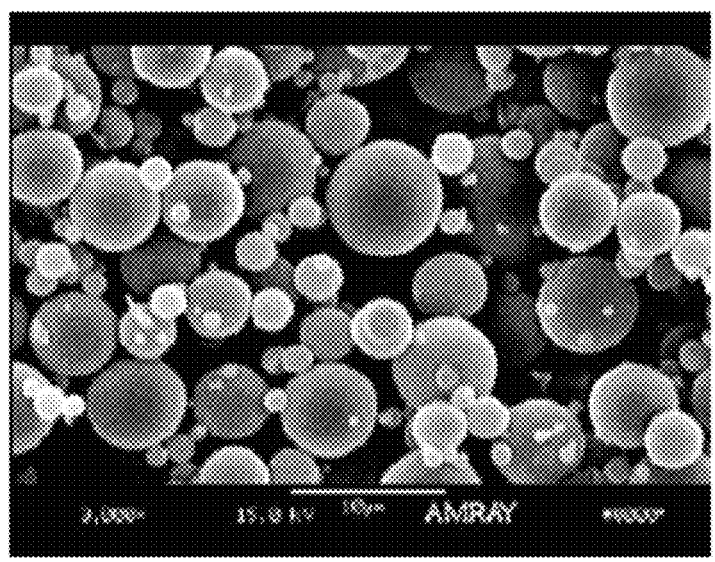
FIG. 4. SEM image of PA microspheres.

Polymeric microspheres are advantageous over many other forms of polymers for drug delivery as they are small enough to be injected. PA has previously been formulated into microspheres with size ranges of 2-20 μm (FIG. 4) (Yeagy, et al., Journal of Microencapsulation 23, 643-653 (2006)). This was accomplished by using an oil-in-water single emulsion solvent evaporation technique (Freitas, et al., Journal of Controlled Release 102, 313-332 (2005)). Briefly, PA is dissolved in dichloromethane (DCM). This solution was then added to a 1% w/v aqueous solution of poly(vinyl alcohol) (PVA) and homogenized for 2 minutes with a handheld homogenizer. The solution was then allowed to stir for 15 minutes to allow the DCM to evaporate. Microspheres were recovered by centrifugation. PVA was then removed by a centrifugation wash. Samples were frozen and lyophilized.

3.4. Adhesion Barriers Currently on the Market

The 5 adhesion barrier products approved by the FDA for use in the US are listed in Table 2. Many other devices have been approved for use in countries other than the US but have not been approved by the FDA (diZerga, et al., Reproductive BioMedicine Online 17, 303-306 (2008)). One such product is Intercoat (carboxymethylcellulose and polyethylene glycol, Ethicon), an injectable gel that has been approved for use in Europe.

TABLE 2

| FDA Approved Adhesion Prevention Products | | | |
|---|---|---|---|
| Product | Composition | Company | Description |
| Preclude | polytetrafluoroethylene | WL Gore | Solid nonresorbable barrier |
| Seprafilm | hyaluronic acid and carboxymethylcellulose | Genzyme Corp. | solid resorbable barrier |
| Interceed | oxidized regenerated cellulose | Gynecare | solid resorbable barrier |
| REPEL-CV | polylactic acid and polyethylene glycol | SyntheMed, Inc. | solid resorbable barrier |
| Adept | 4% icodextrin solution | Baxter Biosurgery | injectable solution |

3.4.1. Seprafilm

With a 58% share of the abdominal adhesion barrier market, Seprafilm is the industry standard. A multi-center study demonstrated that Seprafilm use resulted in 51% of patients being adhesion free after second-look laparoscopies as compared to 6% of patients in the untreated group. The density of adhesions was also lower in patients as compared to the control group. However a systematic review of the literature found that Seprafilm decreased adhesions but had no significant effect on SBO incidence. It did however lead to more abdominal abscesses and leakage of gastric or intestinal fluid at sites of anastomoses. Other systematic reviews found that Seprafilm had no significant effect on readmission rates, pregnancy rates, or pelvic pain in treated patients.

Many surgeons note that Seprafilm is brittle and sticky, making it difficult to apply in patients; these characteristics also exclude Seprafilm for use in laparoscopic surgeries.

3.4.2. Intercoat

Intercoat has been approved for use in Europe since 2002 but was not approved by the FDA for efficacy reasons (Fransen, Annals of Surgical Innovation and Research 2 (2008)). A small clinical study was conducted to determine the efficacy of Intercoat on preventing adnexal adhesion formation, adhesions involving the ovaries and fallopian tubes, in women undergoing gynecologic surgeries, with 26 of the 28 patients undergoing adhesiolysis as a part of their surgery. Formation of new adhesions was determined by second look laparoscopies 6-10 weeks later. Adnexal adhesion score, as defined by the American Fertility Society (ASF), was unchanged in treated patients but was increased from 8.0 to 11.6 in untreated patients. For adnexa with severe adhesions (ASF score ≤6) before the surgery, treated group adhesion scores were reduced by an average of 1.0 while the control group scores increased by an average of 4.6. Overall, 34.5% of treated and 66.7% of untreated adnexa had increased scores. A similar study on a larger group of patients resulted in an ASF score reduction from 11.9 to 9.1 in the treated group as opposed to an increase from 8.8 to 15.8 in the untreated group. In this study only 7% of treated adnexa demonstrated increased ASF score as opposed to 44% of untreated adnexa. A 396 patient study of Intercoat use in spinal surgeries demonstrated a reduction in the need for reoperations when compared to when compared to what is experienced for this surgery, however, as there were no controls for this study, the significance of the findings cannot be determined.

A direct comparison of Seprafilm and Intercoat, as well as Adept, was conducted by Rajab et al. in a rat model. Efficacy was determined by adhesion area as a percent of the cauterized lesion created during surgery. All three products significantly reduced mean adhesion covered area as compared to control. Both Seprafilm and Intercoat resulted in 20% adhesion-free animals in their groups, as opposed to 0% in the Adept and control groups. The mean area of adhesion incidence for Seprafilm (46%) was better than that of Intercoat (55%), but not significantly so (Rajab, et al., Journal of Surgical Research 161, 246-249 (2010)).

3.4.3. Cost-Benefit Analysis

Adhesion barriers are only used in a small percentage of the estimated 9.9 million surgeries that they could be helpful for. One study found that only 10% of patients undergoing abdomino-pelvic surgeries were advised about the risk of adhesion and only 6% were advised about prevention methods. The minimal usage of adhesion barriers is primarily due to the fact that there are no large randomized controlled trials that demonstrate the efficacy of current adhesion barriers to significantly decrease the rate of hospital readmissions due to adhesion related disorders. Without proof that the adhesion barriers can save healthcare costs in the future, their usage will remain minimal; it must be shown that barriers can significantly reduce not just adhesion formation, but also the complications of adhesions that lead to hospital readmissions. A study from the United Kingdom estimated that a product costing £50 (~$80) per patient that resulted in a 16% reduction of readmissions would payback the cost of its investment in 3 years. A product costing £200 (~$315) would need to have a reduction rate of 64.1% in order to pay for itself in 3 years. With an average cost of about $200 per unit, and with some patients requiring more than one unit, the devices currently available do not meet the criteria of being cost effective for use in all patients undergoing abdominal surgery.

3.5. Use of Drugs for the Prevention of Fibrous Adhesions

Many different drugs have been investigated for their potential to prevent adhesion formation. Some of the most common classes of drugs studied are anti-inflammatories, antioxidants, anticoagulants, fibrinolytics, and proteolytics. The anti-inflammatory and antioxidant drugs serve to decrease the wound healing response, thereby preventing the recruitment and proliferation of cells that would form the fibrous adhesions. The anticoagulants prevent fibrinous bands from forming whereas fibinolytics and proteolytics break down the fibrinous bands. The absence of these fibrinous bands would remove the scaffolding that fibroblasts attach to when forming fibrous adhesions. The most significant obstacle to the use of drugs for adhesion prevention is the ability to target drugs to the specific area. This is a critical problem as most of the drugs above, if given systemically at high enough doses to be effective, would inhibit healing of wounds received from surgery in addition to any other adverse side effects that systemic delivery of those drugs would normally cause.

3.5.1. Non-Steroidal Anti-Inflammatory Drugs (NSAIDs)

NSAIDs are a class of drugs that are known to have anti-inflammatory, analgesic (pain reducing), and antipyretic (fever reducing) properties. The also inhibit fibroblast proliferation and formation of granulation tissue. The most common NSAID used is acetylsalicylic acid (aspirin). NSAIDs inhibit cyclooxygenase (COX) enzymes, thereby preventing the synthesis of prostoglandins, prostacyclins, and thromboxane. There are 2 COX enzymes. COX-1 is constitutively expressed in most tissues at constant levels. COX-2 is expressed in reaction to stimuli. It is the inhibition of COX-2 that leads to the therapeutic effects of NSAIDs. When fibroblasts harvested from IP adhesions and normal peritoneum tissue were studied, it was observed that COX-2 was expressed in the adhesion fibroblasts but not in the normal peritoneal fibroblasts (Saed, et al., Fertility and Sterility 79, 1404-1408 (2003)). Adhesion fibroblasts were also found to have lower levels of tissue plasminogen activator (tPA) and higher levels of plasminogen activator inhibitor-1 (PAI-1). tPA and PAI-1 are important molecules in the fibrinolysis pathway; tPA is an anti-coagulant and an activator of fibrinolysis, PAI-1 inhibits tPA. Aspirin increases tPA levels and decreases PAI-1 (Buczko, et al., Thrombosis Research 110, 331-334 (2003); Hammouda, et al., Thrombosis Research 42, 73-82 (1986)). Many studies have come to competing conclusions as to the effect that aspirin has on fibrinolysis. However, the effect aspirin has on fibrinolysis seems to be dependent upon both dose and other signaling molecules in the plasma. Low doses of aspirin have been shown to increase fibrinolysis, while higher doses have an inhibitory effect on the pathway.

Fibrinolysis is an important pathway in the prevention of adhesions as it breaks down the fibrinous bands before they can become permanent. The evidence that low doses of sustained aspirin are preferable has been borne out in animal models. In a rat model, animals were given either 0.35, 0.7 or 1.4 mg of aspirin every 6 hours for 48 or 96 hours after surgery. The rats that were given the lowest dose for the longest time (0.35 mg, 96 hours) had the fewest adhesions. The rats given higher doses for any amount of time had the highest incidence of adhesions, however, the difference between these groups was not significant and no group was significantly different from the untreated control (Golan, et al., Human Reproduction 10, 1797-1800 (1995)). In a rabbit model, rabbits were given either 1.7 mg/kg/day or 28.0 mg/kg/day for 5 days after surgery. The low dose group had a significantly lower adhesion rate at 44% than the high dose group at 77%, the control had 100%. It was observed that the lower doses of aspirin preferentially inhibited thrombaoxane rather than prostacyclin and that this is what accounts for the increased efficacy of adhesion (Muzii, L. et al. Human Reproduction 13, 1486-1489 (1998)).

Another NSAID, aceclofenac, was studied for its ability to prevent adhesions. 5 mg/kg/day was injected intramuscularly into rabbits for 7 days. A significant difference was observed in the fibrous area between the control group and the treatment group. It was also observed that the treatment group had an 8% decrease in fibroblasts at the injury site (Sandoval, et al., Eur Spine J 17, 451-455 (2008)).

3.5.2. Antioxidants

Oxidative stress leads to increased adhesion formation. Vitamin E and melatonin are two antioxidants that have been extensively investigated for their ability to mitigate this effect and inhibit adhesion formation. In addition to reducing oxidative stress, vitamin E also inhibits COX-2 and platelet aggregation. In fact, vitamin E has been observed to potentiate the anticoagulant effect of aspirin in vitro. This may be a useful characteristic in the proposed devices as it may help the SA prevent the formation of fibrinous bands. Vitamin E also inhibits TGF-β, which has an anti-fibroblastic effect, and decreases collagen production which may help prevent adhesions. In animal studies, vitamin E has been shown to reduce adhesion formation by 80% when administered through IP injection, but not when administered orally or intramuscularly (de la Portilla et al., Diseases of the Colon & Rectum 42, 2157-2161 (2004)). In a rat model IP injections of vitamin E were as effective as Seprafilm (Corrales, et al., Acta Cirúrgica Brasileira 23, 36-41 (2008)).

Melatonin is a more effective free radical scavenger than vitamin E. It also has anti-inflammatory and anti-fibroblastic properties as well. IP injection of melatonin has been demonstrated to significantly reduce adhesion formation in rat and dog models (Saeidi, et al., Interactive Cardiovascular and Thoracic Surgery 9, 26-28 (2009); Ara, et al. Life Sciences 77, 1341-1350 (2005)). Further proof that melatonin has an effect on adhesion formation has been demonstrated in animal models with pinealectomies, surgeries to remove the pineal gland which normally produces melatonin to regulate circadian rhythms. Adhesion formation in rats with pineal glands removed had significantly more adhesions than controls; when rats without pineal glands were given IP melatonin adhesion formation was similar to the control. Rats with intact pineal glands and injections of melatonin had significantly less adhesions than the control (Ersoz, et al. Journal of Gastroenterology and Hepatology 24, 1763-1767 (2009)).

3.6. Sterilization Techniques

Two common sterilization techniques, electron beam irradiation and gamma ray irradiation, were used to determine the effect these techniques had on the adipic-PA and on poly(oCPX). The polymers were sent to Johnson & Johnson's Sterile Process Technology plant where they were subjected to 25 and 50 kGy of the two types of radiation. These doses represent the typical and typical maximum processing doses, respectively, generally used for sterilization. Processed samples were tested for changes in molecular weight (MW), glass transition temperature ($T_g$), infrared spectrum (IR), cytotoxicity, and degradation rates. No significant differences were found in any of these characteristics between irradiated samples and traveler samples (identical samples that are subjected to all of the same conditions-shipping, storage, etc., as the irradiated samples).

Section 4.

The development of resorbable adhesion barrier devices that are more efficacious than those currently available on the market by combining controlled release of drugs with a physical barrier are described herein.

4.1. The Determination of the Composition, Formulation, and Amount of SA-Based PAE that Gives the Most Optimal Drug Release Profile for Adhesion Prevention and the Determination of how Best to Incorporate the PAEs into Adhesion Barriers Currently on the Market.

4.1.1. Preparation of PA Microspheres

Microspheres of adipic-PA will be prepared using an oil-in-water single emulsion solvent evaporation technique as described above. Adipic-PA has been shown to degrade relatively quickly (approximately a week), which is a desired property for this application. The microspheres will be characterized by SEM to confirm a spherical shape and determine the microsphere size distribution. The microspheres will also be characterized by differential scanning calorimetry (DSC) to determine if their $T_g$ is above physiological temperature (37° C.). If the $T_g$ is below 37° C. the microspheres may not retain their shape when they are at that temperature, thus potentially affecting degradation rates.

4.1.2. Admixture of Microspheres into Intercoat and In Vitro Drug Release

The microspheres will be admixed into samples of Intercoat at 0.1, 0.2, 0.3, 0.4 mg microspheres/ml Intercoat. These samples will then be used for in vitro SA release studies by placing a known mass of the sample into glass vials with 10 mL PBS at pH 7.4 rotating in an incubator set to 37° C. and 80 rpm. The PBS will be collected at specific time points, replaced with new PBS, and placed back into the incubator. The collected PBS will be analyzed on a UV/vis spectrophotometer set to measure the absorbance at 303 nm. The absorbance value for each sample will be compared to a calibration curve to determine the amount of salicylic acid released into that sample. The release rates from the above concentrations of microspheres will be used to determine the optimal concentration to obtain a constant release of 42.5 μg SA/ml Intercoat/day. This rate corresponds to the targeted 100 mg/day dose in an average 60 kg human given one unit of Intercoat (40 ml) (Ersoz, N. et al., Journal of Gastroenterology and Hepatology 24, 1763-1767 (2009)).

The optimal polymer and microsphere concentration will degrade to give a release rate of 42.5 μg SA/ml Intercoat/day for about least 10 days. If incorporation into a hydrogel changes the degradation rate of the adipic-PA such that the normal degradation is drastically changed from what has been seen previously, another polymer with a more hydrophobic (if the degradation rate is too fast) or hydrophilic (if the degradation rate is too slow) linker will be synthesized and formulated into microspheres, and the in vitro studies repeated to obtain a more desirable release curve.

4.1.3. Electrospinning PA-Containing Membranes

SA-based PAEs will be admixed with high molecular weight (~100 kDa) PEG (Sigma-Aldrich) and be electrospun into mats. PEG has been demonstrated to be better than PLA at preventing adhesions. If PA cannot be electrospun with PEG, PLGA will be used as has been done before (Griffin, et al., Journal of Biomedical Materials Research. Part A. 97(3), 230-242 (2011)).

The $T_g$ of the membranes will be analyzed by DSC. SEM will be used to determine the fiber diameter distribution. The mechanical properties of the membrane will be assessed by obtaining the stress strain curve of the membrane. Measurements will be taken for both dry and fully hydrated membranes. An optimal membrane would be less brittle than Seprafilm at each state. The swelling ratio of the membrane will also be assessed using Eq. 1 after being hydrated in PBS for 24 hours.

$$Q = \frac{w_s - w_d}{w_d} \qquad \text{Equation 1}$$

Q=swelling ratio
$w_s$=weight of swollen membrane
$w_d$=weight of dry membrane 4.1.4. Adhering PolyAspirin-Containing Electrospun Membranes to Seprafilm These membranes will then be adhered to samples of Seprafilm. The most effective way to adhere these membranes to Seprafilm will be determined based on the mechanical properties of the combined device when evaluated under both the dry and the hydrated conditions. Furthermore, adherence levels will be assessed at both hydration states. The first methods attempted will be to use small amounts of water, to make the Seprafilm sticky, or DCM, to slightly dissolve the top layer of the membrane enough to make it adhere to the Seprafilm.

Electrospun membranes of PA and another polymer were chosen over spray-coated or solvent-cast films of PA alone due to the less desirable mechanical properties of the latter-mentioned final products. PA-containing electrospun membranes are much less brittle and are more elastic than solid PA films. These are necessary properties if the polymer is to remain attached to Seprafilm, as it will expand when placed in an aqueous environment. The increased surface area of a fibrous membrane, as compared to a solid film, is also desirable as a method to increase SA release rates. The weight percent of PA in the electrospun membrane will need to be controlled such that the swelling of the membrane will be comparable to Seprafilm in order to prevent disassociation of the two layers when placed in an aqueous environment.

4.1.5. In Vitro SA Release Studies from PA/Seprafilm Device

In vitro SA release studies will be performed on the PA/Seprafilm device similarly to those previously described for the Intercoat and microsphere admixture. The composition of the membrane will be adjusted as needed to obtain optimal mechanical and degradation properties. The thickness of membrane layers adhered to Seprafilm will be adjusted to obtain the desired 100 mg SA/day/Seprafilm unit dose.

4.1.6. Adjusting the Release of Salicylic Acid

PAs generally release SA in a linear fashion after a short lag period. For the proposed devices, SA release will be desired soon after implantation for the effect it can have on coagulation and inflammation. For this, different weight percentages (to be determined by the SA release curve of the polymer alone) of SA and/or SA-based diacids will be admixed into the PA to give the desired release curve.

4.1.7. Cytotoxicity Studies

Both devices will be assessed for their in vitro cytotoxicity toward L929 fibroblasts using methods similar to those described previously in section 3.1.4. On day 1, the cells will be plated 2000 cells/well in multiple 96 well plates with normal cell culture media. A plate with a range of cell seeding densities will also be plated for calibration of the MTS assay. Samples of the devices will also be placed in separate cell culture media stocks on day 1. At 24 hours, the media in the cell culture wells will be replaced with media from the vials containing the device samples or normal media in the case of the controls, and the MTS assay will be used on the calibration plate. At 48 hours, one cell culture plate will be assessed at that time using an MTS assay and trypan blue exclusion assay for cell viability. The media in the cell culture wells will again be replaced with fresh media from control and sample vials. At 72 and 96 hours, the other sets of cells will be assessed using the MTS and trypan blue assays. The cell media will be replaced at 72 hours. Light microscopy images of cells will be taken at each 24 hour time point to observe any changes in cell morphology.

4.1.8. Anticipated Results

It is anticipated that the incorporation of microspheres into Intercoat may slightly decrease the degradation rate of the microspheres as compared to microspheres free in PBS as the hydrogel may protect the polymer surface from the shear forces of moving liquid that can facilitate more rapid hydrolysis.

The electrospun membranes are expected to form without problem as PA has successfully been electrospun with PLGA, and PEG has been successfully electrospun as well (Griffin, et al., Journal of Biomedical Materials Research. Part A. 97(3), 230-242 (2011); Zong, X. et al., Annals of Surgery 240, 910-915 (2004); Yang, et al., Journal of Biomedical Materials Research. Part A. 82, 680-688 (2007); Yang, et al., Acta Biomaterialia 5, 2467-2474 (2009)). The membranes are expected to be less brittle than Seprafilm as the PA/PLGA films are quite flexible, whereas Seprafilm is not. It is also expected that the membranes will degrade faster than is usually observed for PA as PEG is very hydrophilic and will allow more water into the polymer matrix than would PA alone. The increased surface area of the membrane fibers should also lead to a faster degradation rate than a PA disk.

The admixture of SA and or SA-based diacids is expected to negate any lag period in the drug release curves. This is a desirable characteristic of the devices, as the anticoagulant effect of the SA is most needed directly after implantation to prevent the formation of the fibrinous bands that are precursors to fibrous adhesions.

The cytotoxicity studies are expected to show little to no toxicity from the devices as has been observed with other PA devices.

If the homogeneous incorporation of microspheres into Intercoat significantly slows the release of SA from the device, the microspheres may be applied to the outer surface of the Intercoat sample rather than distributed within it.

If proper adhesion of the two layers becomes an issue with procedures described above, a PA/PEG admixture could be spray-coated directly onto the Seprafilm.

4.2. The Admixture of an Antioxidant into the SA-Based PAE and Determination of the Release Profile of the Antioxidant and its Effect on Polymer Degradation.

4.2.1. Admixing Vitamin E into the PolyAspirin

Both vitamin E and melatonin have demonstrated the ability to reduce adhesions in animal models. As there have been no studies comparing the efficacy of the two against each other, it is proposed that vitamin E be the first choice for the antioxidant used as it is generally regarded as safe (GRAS) by the FDA. It also acts synergistically with SA to reduce clotting which could be very helpful in vivo by preventing fibrin deposition that can lead to adhesions (Celestini, A. et al. Haematologica 87, 420-426 (2002).

Vitamin E will be admixed into the PA structures described above. In vitro studies will be conducted, as described earlier, to observe the release of vitamin E and its effect on the degradation profile of the PA. HPLC will be used to measure the amounts of drugs released. The HPLC method will entail passing the samples through a C18 column with a mobile phase of 75:25 PBS(pH 2.5):acetonitrile at 1 ml/min with the detector set to measure at both 303 and at the maximum absorbance wavelength of Vitamin E. Peak areas will be compared to a calibration chart made from measuring the peaks of standard solutions.

Previous studies testing the effect of vitamin E on adhesion formation have been performed by dosing animals with approximately 20 mg vitamin E/kg immediately after induction of surgical lesions (de la Portilla, F. et al. Diseases of the Colon & Rectum 42, 2157-2161 (2004); Corrales, et al., Acta Cirúrgica Brasileira 23, 36-41 (2008)). The weight percent of admixed vitamin E will be chosen so as to release 20 mg/kg within 24 hours and/or to ensure no more than 25 mg/kg/day is released.

If the vitamin E significantly changes the degradation rate of the PA, a different PA will be synthesized for this admixture to achieve a polymer that releases SA at the same rate as the previously developed devices.

4.2.2. Anticipated Results

It is anticipated that the hydrophobic vitamin E may decrease the degradation rate of the polymers, although this is unlikely, as previous admixtures have not significantly changed PA degradation rates. The above HPLC method has been used for separation of SA but the mobile phase is mostly aqueous. Accordingly, a gradient method from 100% PBS to 100% acetonitrile at 1 ml/min is proposed may be an alternative method.

4.3. The Determination of the Effects of Common Sterilization Techniques on the Devices and Comparison of the Efficacy of the Combination Devices Against their Equivalent Non-PolyAspirin Device In Vivo.

4.3.1. Radiation Stability Tests

Optimized devices will be sent to Johnson & Johnson's Sterile Process Technology plant where they will be exposed to 25 or 50 kGy of electron beam or gamma radiation. The molecular weights, $^1$HNMR and IR spectra, thermal properties, degradation profiles, and cytotoxicity assays of the irradiated samples will be compared to traveler samples.

The Seprafilm sample will also need to be observed for any change in the ability of the two layers to adhere to each other.

4.3.2. In vivo Studies in Rats

The different samples will be implanted into rats. The rats will be broken into seven groups: 1) No barrier or drugs; 2) Intercoat; 3) Seprafilm; 4) Intercoat+PA; 5) Seprafilm+PA; 6) Intercoat+PA+Vitamin E; and 7) Seprafilm+PA+Vitamin E.

Figure 5:
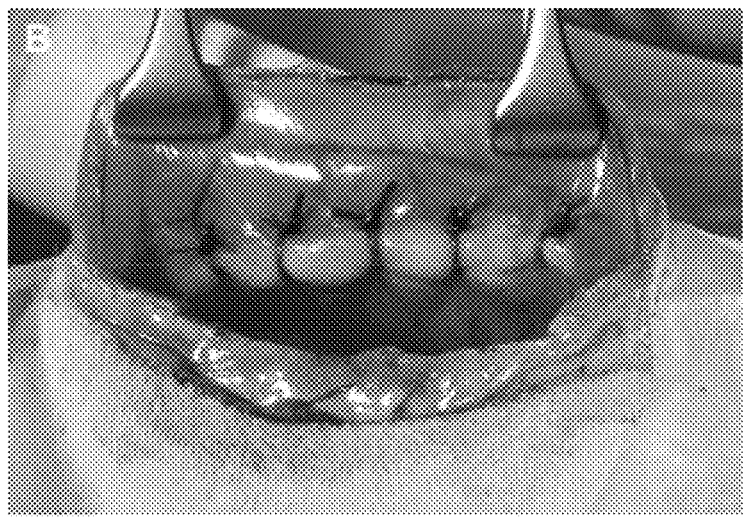
FIG. 5. Experimental lesion formed by electrocautery with sutures (Rajab, et al., Journal of Surgical Research 161, 246-249 (2010)).

The surgery will consist of a ventral incision being made. The parietal peritoneum will be electrocauterized and have five stitches placed at the traumatized area (FIG. 5). The designated barrier for that rat will be placed into the peritoneum and the incision will be sutured closed. The rats will be sacrificed 14 days after surgery. An investigator who is blinded to the animal group will measure the fraction of the lesion area covered in adhesions. The healing of the incision line will be closely monitored during the 2 weeks to observe any differences in healing rate between different groups. The mean and standard deviation of the fraction of lesion area covered by adhesions will be determined for each group. Significance of differences between different groups will be determined by one-way ANOVA with $p \leq 0.05$.

4.4.3. Anticipated Results

Previous radiation stability tests on adipic-PA indicated that it is stable after exposure to typical sterilization doses of electron beam and gamma radiation. The effect of radiation on the other materials in these devices could affect the PA characteristics, especially the degradation profile.

Devices with vitamin E may reduce adhesion more than the PA devices without vitamin E, which will in turn reduce more adhesions than the original devices. The untreated control is expected to have severe, extensive adhesions. The synergistic effect that SA and vitamin E may have on clotting could prevent closure of the incision wound. A trial animal will be tested with a vitamin E device to test for this before the rest of the group is operated on to test this possibility. If the device does seriously impede wound healing, one of two options will be chosen: reduce the amount of SA and vitamin E in the device or replace the vitamin E with melatonin.

Section 5. Summary

Described herein are methods to improve two adhesion barrier devices by incorporating biodegradable polymers into the devices to allow for targeted, controlled release of drugs, specifically salicylic acid and vitamin E. The adhesion barriers currently available on the market are not efficacious enough to warrant their ubiquitous use. The devices described herein may lead to a better cost-benefit ratio than current barriers, thereby leading to more ubiquitous use in patients, resulting in fewer adhesion related complications.

Example 2

Bioactive-Based Polyanhydrides for Controlled Drug Release in Surgical Wounds

As described herein are experiments directed towards the production of devices for wound healing applications where the device is composed, in whole or in part, of a salicylic acid (SA)-based poly(anhydride-ester) (SAPAE). SAPAEs have been formulated by various methods that would allow them to be applied to a wound site in various formulations, such as, e.g., a polymer powder/microspheres in a liquid excipient (e.g., mineral oil), electrospun mats, and polymers that are above their glass transition temperature ($T_g$) at room temperature such that they can be easily applied to a surface.

The presence of these formulations at a wound site would result in polymer degradation and subsequent release of SA. This local release of SA over an extended period of time can help to mitigate local pain, inflammation, and other wound healing complications such as fibrous adhesions. The physical presence of the polymer device at the wound site is another way in which these devices can prevent fibrous adhesions.

There are many devices on the market that are designed to decrease adhesion formation, most of these devices are solid films, gels, or liquids that act solely as physical barriers to prevent adhesion formation between the two surfaces they are separating. These devices do no prevent adhesion formation at non-adjacent sites. They also do not mitigate pain or inflammation. None of the current devices combine physical barriers with controlled release of drug. In contrast, the wound healing devices described herein are unique in that they allow for a completely biodegradable device that can be implanted at a wound site, such as a surgical incision, to mitigate pain, inflammation, adhesion formation and other problems during wound healing, while also providing a physical barrier that can further help to prevent fibrous adhesion formation.

Bioactive-Based Polyanhydrides

Bioactive-based polyanhydrides, specifically salicylic acid-based poly(anhydride-esters), have been previously generated (Schmeltzer, et al., Biomacromolecules, 6 (1) 359-367 (2005); Prudencio, et al., Macromolecules, 38, 6895-6901 (2005); Carbone, et al., Macromol Rapid Comm, 30, 1021-1026 (2009)). Salicylic acid, a bioactive metabolite of aspirin, is a nonsteroidal anti-inflammatory drug. It has analgesic and anti-inflammatory properties as well as mild antimicrobial activity. The localized, controlled release of salicylic acid at the surgery site can help to alleviate post-operative pain and swelling, as well as mitigate the inflammatory response that can lead to post-operative complications such as fibrous adhesions.

Drug Loading and Control of Release

In these polymers, salicylic acid is chemically incorporated within the backbone of the polymer and connected via biocompatible linker molecules. When these polymers are placed into an aqueous environment, the anhydride and ester bonds are hydrolytically cleaved to release the drug (Scheme 3). This chemical incorporation of the drug molecules prevents the burst release of drug typically seen with polymeric drug delivery devices. It also allows very high drug loading (>70%).

Scheme 3. Degradation of the salicylic acid-based polyanhydride to release the drug and biocompatible linker molecule. The linker molecule is shown above as "R"; however, the linker molecule is also referred herein as "L". While salicylic acid is shown in this scheme other biologically active agents, as described herein, may also be used in other embodiments.

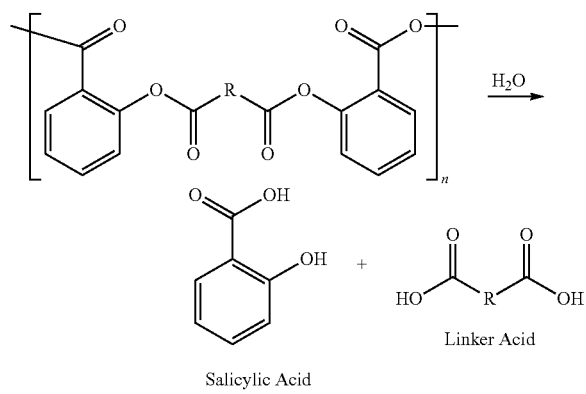

Salicylic Acid | Linker Acid

Figure 6:
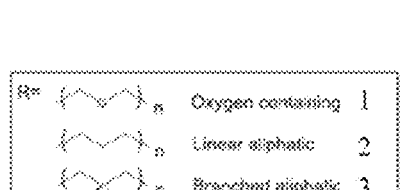
FIG. 6. Graph of SA release with various linkers.
Figure 6:
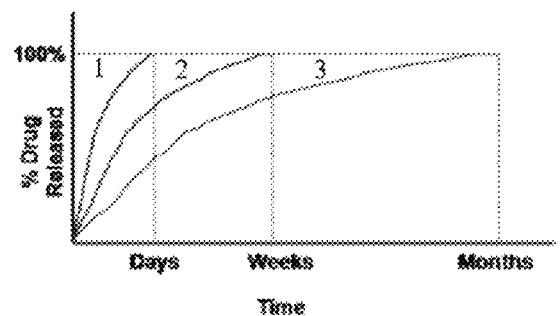

The rate of drug release can be controlled by changing the linker molecules used. Oxygen-containing linkers (such as diglycolic acid) result in polymers that degrade in a matter of days, linear aliphatic linkers (such as adipic acid) result in polymers that degrade over weeks, and branched aliphatic linkers (such as diethylmalonic acid) result in polymers that degrade over months (FIG. 6). Copolymers can be prepared containing more than one linker such that the release rate can be finely-tuned to achieve a wide range of desired release rates/durations.

Incorporation of Other Drug Molecules

Polymers containing other NSAIDs, antioxidants, antibiotics, and analgesics have also been developed. In addition to chemically incorporating drugs into the polymer, it is also possible to physically admix additional drug into the polymer matrix (similar to most polymeric drug delivery applications) to achieve a synergistic effect from the concurrent delivery of multiple drugs at the implantation site (Johnson, et al., J Biomed Mater Res, Part A, 91(3):671-8 (2009)).

Formulations

Figure 7A:
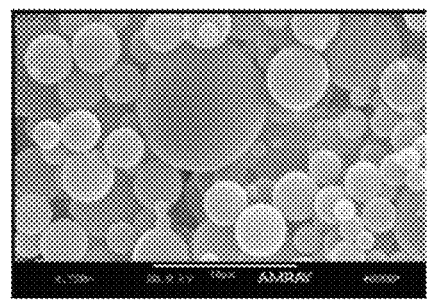
FIGS. 7A-C. Possible formulation geometries.
Figure 7B:
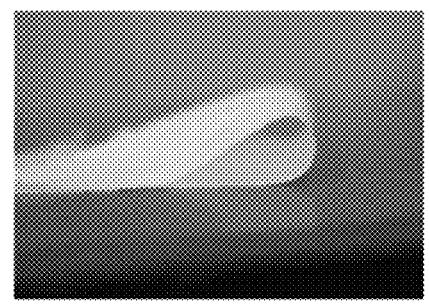
Figure 7C:
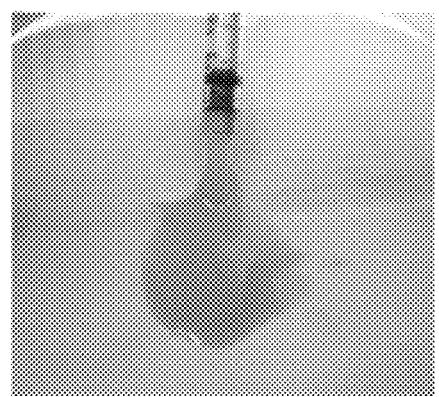

These polymers may be formulated for a wide range of applications. For example, the polymers have been formulated into gels and microspheres/powders (FIG. 7A) (Yeagy, et al., J. Microencapsulation, 23 (6) 643-653 (2006). The microspheres/powders can be dispersed within an excipient (e.g., liquid) to result in a cream, ointment, or spray depending on the need, while still maintaining controlled release of drug (FIG. 7C). Additionally, these polymers may be formulated into flexible mats (e.g., electron spun polymer mats) or films (e.g., electrospun films) (FIG. 7B) (Griffin, et al., J Biomed Mater Res A, 97A (3) 230-242 (2011)). For example, SAPAEs have been blended with poly(lactide-co-glycolide) and PEG and formulated into microspheres and electrospun films.

Stability

Storage stability studies indicate that if maintained at 5° C. in a moisture-free environment, the polymers should be stable for >12 months (deRonde, et al., Polymer Degradation and Stability, 95, 1778-1782 (2010)). It has been demonstrated that the polymers are readily sterilized by both electron beam and gamma irradiation (up to 50 kGy) without adverse effects on the polymer properties and drug release rates (Rosario-Melendez, et al., Polymer Degradation and Stability, 96, 1625-1630 (2011)).

In Vivo Results

These bioactive-based polymers have been implanted into both animals (Erdmann, Biomaterials 21 (24) 2507-2512 (2000); Harten, et al., J Biomed Mater Res A 72A (4) 354-362 (2005)) and humans without evidence of irritation or inflammation.

In summary, it is possible to produce polyanhydride systems that can finely control the release of drugs with modified release rates and in vivo retention times. These polymers may be used for the localized release of NSAIDs, which can provide the desired analgesia and anti-inflammatory effects, or other biologically active agents. Furthermore, these polymers are fully biodegradable and do not result in irritation at the treatment site. They can be formulated in multiple ways that would enable easy application at the surgical site before suturing.

Copolymers: SAPAE Monomers and PEG Oligomers

Described below is the synthesis of copolymers comprised of SAPAE monomers and PEG oligomers, which have the desired properties that would allow them to be applied to a wound (Scheme 4). While an SA-based PAE is discussed below, other bioactive-based polyanhydrides (e.g., other nonsteroidal anti-inflammatory drugs, anti-oxidants, antimicrobials, etc.) that would aid in the wound healing process may also be used. Additionally, the SAPAEs may also be blended with other polymers to create a film or gel that could be used for wound healing purposes.

Scheme 4.

A.

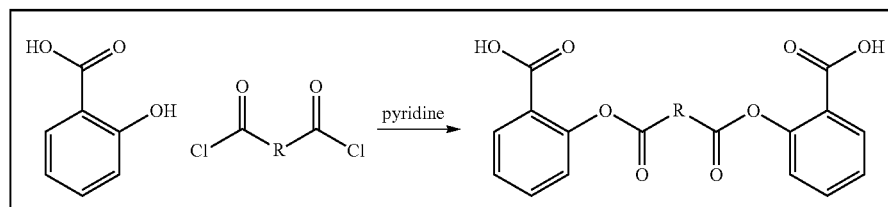

-continued

B.

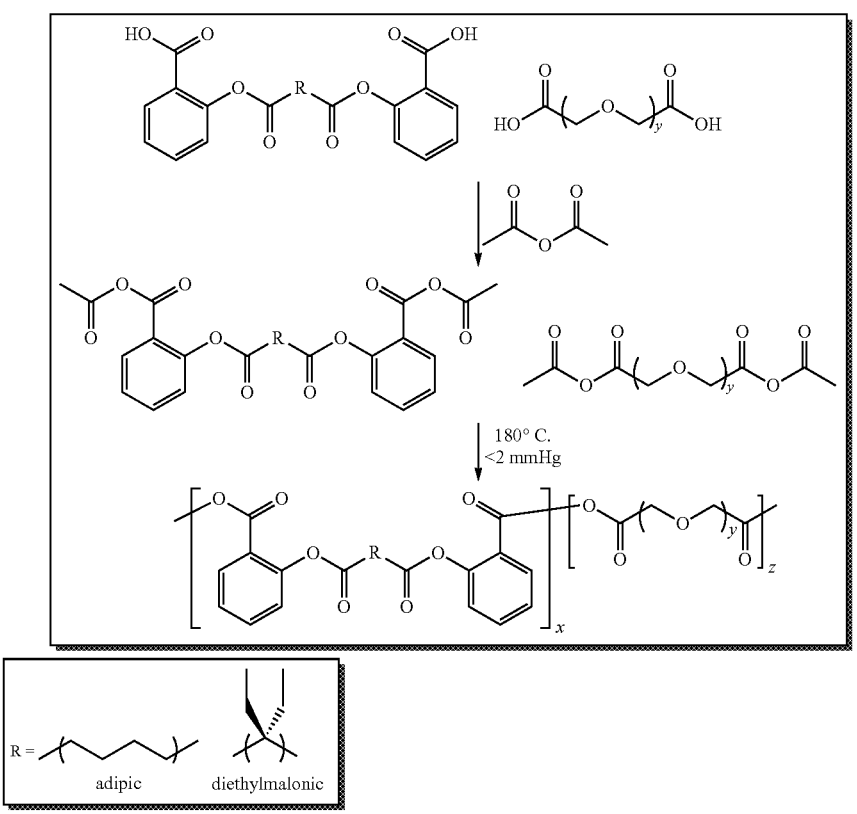

Synthesis of the salicylic acid-based diacid. B. Synthesis of the salicylic acid and poly(ethylene glycol) copolymer from the salicylic acid-based diacid and poly(ethylene glycol) bis(carboxymethyl) ether (commercially available). while the linker molecule, "R", (also described herein as "L" is shown in this schedme as adipic or diethylmalonic, other linker molecules as described herein may also be used. Similarly, salicylic acid as shown; however, other biologically active agents, as described herein, may also be used in other embodiments.

These copolymers, which are comprised of SAPAE monomers and PEG oligomers, are copolymerized at various ratios. For example, ratios of adipic linked diacid:PEG have been generated at ratios of 4:1, 3:1, 2:1, 1:1, and 1:2. Mechanical properties of the copolymers were evaluated. Copolymers with ratios of 2:1, 1:1, and 1:2 had mechanical properties considered beneficial for wound healing applications, including for the prevention of fibrous adhesion. Diethylmalonic diacid:PEG copolymers with ratios of 4:1 and 3:1 have also been generated. These copolymers have been characterized by nuclear magnetic resonance spectroscopy, thermal analysis, and gel permeation chromatography. They have also been evaluated for their drug release profiles in phosphate buffered saline. These polymers are synthesized by met condensation polymerization, similar to other SAPAEs (Schmeltzer, et al., Biomacromolecules, 6 (1) 359-367 (2005); Prudencio, et al., Macromolecules, 38, 6895-6901 (2005); Carbone, et al., Macromol Rapid Comm, 30, 1021-1026 (2009)). Briefly, the diacid and carboxylated PEG oligomers are combined by desired weight ratio and acetylated with acetic anhydride, excess solvent is removed by evaporation, then the remaining monomers are heated at 180° C. under vacuum with constant stirring to achieve the copolymer.

Generally, the higher the amount of salicylic acid based monomers, the higher the glass transition temperature ($T_g$). Typical glass transition temperatures for four ratios of adipic linked diacid:PEG are shown below in Table 3. These low $T_g$s allow them to be easily manipulated at room temperature.

TABLE 3

| Adipic linked Diacid:PEG Ratio | Glass Transition Temperature ($T_g$) |
|---|---|
| 3:1 | 10° C. |
| 2:1 | −5° C. |
| 1:1 | −25° C. |
| 1:2 | −38° C. |

The polymers with the diethylmalonic linker had higher $T_g$s (23° C. for 3:1) than similar adipic polymers (10° C. for 3:1).

The number average molecular weights of the polymers tends to be 5-10 kDa but it is highly variable.

In vitro drug release studies show that the greater the PEG percentage of the polymer, the faster it degrades. 50 mg samples of the 1:2 adipic degrade in ~4 days, while the 1:1 and 2:1 take over a week.

Formulations

Figure 8:
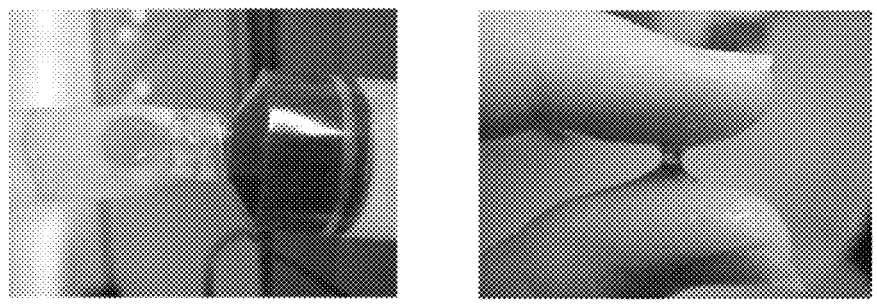
FIG. 8. PEG copolymer gel, which behaved like viscous liquids.

The copolymer is a viscous polymer that acts like a gel (FIG. 8). These copolymers can have $T_g$ values below room temperature such that the polymer can be easily applied to a wound site, such as via a syringe or be extruded out of a tube (FIG. 8). This aspect of the copolymers allows them to be easily applied to various surfaces where they adhere well.

The copolymers, medical devices and compositions as described herein can be implanted at a wound site, resulting in localized analgesia and the mitigation of inflammation and fibrous adhesion formation near the wound. This placement would result in improved wound healing, as well as easing patient discomfort after surgery with fewer side effects than systemic analgesia. Current fibrous adhesion barrier devices have poor efficacy as they only act as a physical barrier between adjacent surfaces. The present copolymers, medical devices and compositions as described herein would act as a physical barrier against adhesion formation while also releasing SA that may help prevent adhesion formation in distant regions, as oral acetylsalicylic acid was found to prevent adhesion formation (Muzii L et al., Human reproduction, 13 (6): 1486-1489, 1998). SA would also provide the additional benefits of local analgesia and mitigation of inflammation.

The invention also includes the subject matter of Example 3, which is described in the following consecutively numbered pages.

Example 3

Figure 9A:
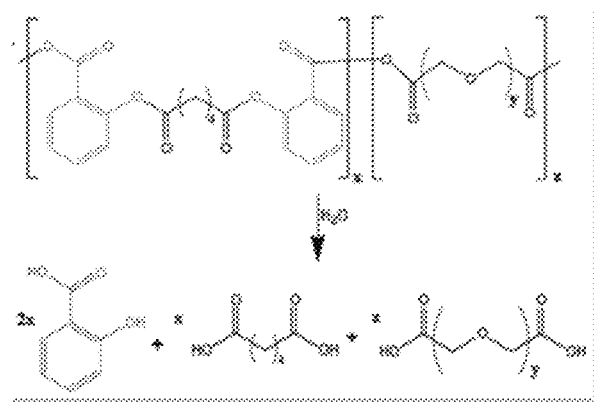
FIGS. 9A-D.

Salicylic Acid-Based Poly(Anhydride-Esters) for the Prevention of Fibrous Adhesions Fibrous adhesions are bands of fibrous tissue that develop due to increased inflammation after surgery or other trauma. Depending on where they form, adhesions can lead to serious complications such as chronic pain, infertility, and intestinal obstruction. Current methods to prevent adhesion formation focus on placing physical barriers at likely adhesion sites; however, they do not prevent adhesion formation at distal sites nor do they significantly decrease the incidence of adhesion related complications. A salicylic acid (SA)- and poly(ethylene glycol)-based poly(anhydride-ester) copolymer (SAPAE) has been synthesized that degrades to release SA, an anti-inflammatory drug, in a localized, controlled manner (FIG. 9A). This SAPAE can act as both a physical barrier to adhesion formation as well as a pharmaceutical treatment to better prevent adhesion formation.

Materials and Methods

Acetylated 1,6-bis(o-carboxyphenoxy)hexanoate (Prudencio, Macromolecules, 2005, 38, 6895-6901) and poly(ethylene glycol) bis(carboxymethyl ether) were melt polymerized in a 2:1 weight ratio to form the SAPAE as a random copolymer. In vitro release studies were performed on 50 mg samples of polymer in phosphate buffered saline (pH 7.4) in an incubator shaker (37° C., 60 rpm). Degradation media was collected at various time points and analyzed for SA concentration. To determine the cytotoxicity of the copolymer, L929 cells were cultured in media with 0.1 mg/mL copolymer and 1% DMSO (with a DMSO control). Cell viability was determined by MTS at 24, 48, and 72 hours. Primary human macrophages were incubated with the copolymer (0.1 mg/mL, 1% DMSO) and 100 ng/mL lipopolysaccharide (LPS), a DMSO/LPS positive control, and a DMSO (no LPS) negative control to monitor TNF-α secretion (determined by ELISA assay) as a measure of inflammation. Macrophage viability was also determined by MTS.

Results and Discussion

Figure 9B:
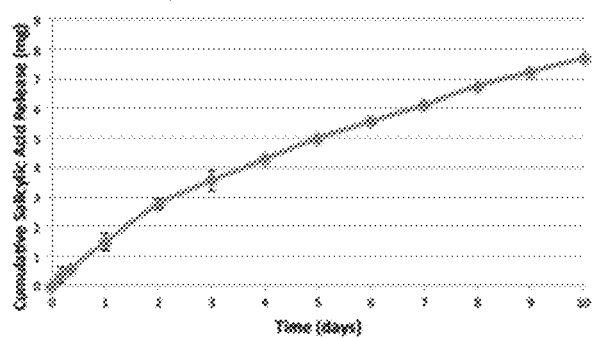
Figure 9C:
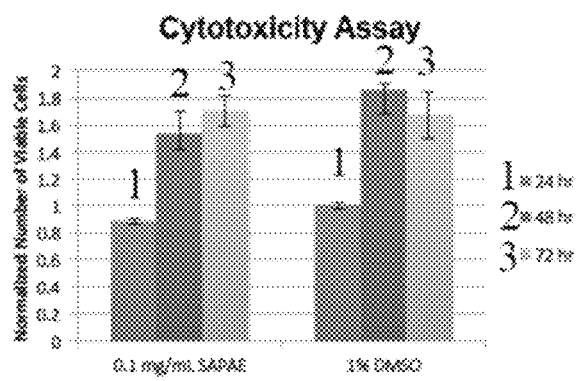
Figure 9D:
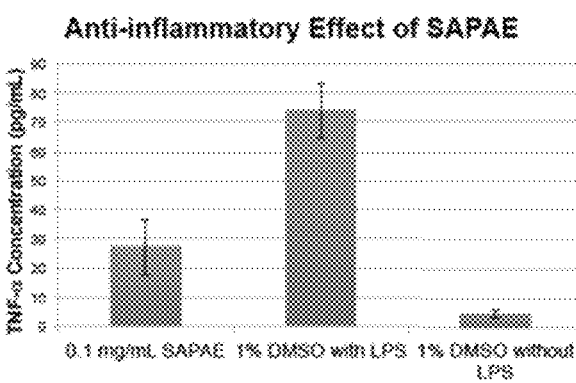

The synthesized polymer has a low glass transition temperature (−5° C.) that allows extrusion from a syringe at room temperature for easy application in a surgical setting. The in vitro drug release profile was observed to be close to zero-order indicating a stable SA release rate over the first 10 days (FIG. 9B)—an important finding, as the first 7-10 days after surgery are critical to adhesion formation. At the end of 10 days, polymer still remained. Cell studies with both fibroblasts and macrophages determined that the polymer is not cytotoxic at 0.1 mg/mL (FIG. 9C). The SAPAE at this concentration significantly (p<0.001) decreases TNF-α secretion in LPS activated macrophages (FIG. 9D) indicating that the polymers are capable of reducing inflammation that could lead to fibrous adhesions.

Conclusions

The aforementioned SAPAE degrades to release SA in a controlled manner throughout the critical adhesion formation period. It was also found to be non-cytotoxic at levels at concentrations that have a significant anti-inflammatory effect in vitro. In vivo efficacy studies of this SAPAE at reducing the extent and severity of adhesion formation in a rat peritoneal adhesion model will be performed.

Example 4

Flowable Salicylic Acid-Based Poly(Anhydride-Esters) for Injectable Barrier Applications Introduction Fibrous adhesions are bands of fibrous tissue that join two surfaces in the body that are not normally connected. They generally form after injury to an area that results in increased inflammation. Surgery, trauma, infections, radiation, and ischemia can all lead to adhesion formation, with surgery being the most common cause. Adhesions are a serious problem that can lead to many complications, including chronic pain, infertility, and intestinal obstruction. Fibrous adhesions have an enormous impact on the healthcare system. It has been estimated that 95% of abdominal and pelvic surgeries, including gynecologic, result in adhesions. Adhesion related problems account for 6% of hospital readmissions and 1% of all hospitalizations in the United States. Over 400,000 abdominal adhesiolysis procedures, a surgery to dissect fibrous adhesions, are performed annually. While adhesiolysis can help alleviate some pain and complications associated with adhesions, the effect is often temporary as the adhesions tend to grow back after the procedure.

Adhesion-related complications often lead to additional surgeries, which is particularly alarming when one takes into account that the presence of adhesions makes such secondary surgeries even more difficult and dangerous, increasing surgery time, hospital stay, complications, blood loss, morbidity, and mortality. While there has been some effort to develop devices to reduce adhesion formation, no device has been proven to significantly reduce the incidence of adhesion-related complications (Al-Jaroudi et al., Adhesion Prevention in Gynecologic Surgery. Obstetrical and Gynecological Survey. 2004; 59(5):360-7).

The physiological pathway that leads to abdominal adhesion formation has been well studied. After surgery, fibrinogen from blood in the peritoneal cavity form a fibrin matrix. This matrix forms into transient fibrinous bands that degrade by fibrinolysis or become a scaffold for fibroblasts to create permanent fibrous adhesions. The occurrence of fibrinolysis is dependent upon the levels of different cytokines and enzymes, with the first 7-10 days after surgery being the most critical for adhesion formation.

Both physical and pharmaceutical methods have been investigated to prevent adhesion formation (Tingstedt et al., Eur Surg Res. 2007; 39:259-68; Ward et al., Journal of Surgical Research. 2011; 165(1):91-111; Alpay et al., Seminars in reproductive medicine. 2008; 26(4):313-21). Various solids, gels, and fluids have been explored as physical barriers, the main purpose of which is to separate surfaces where adhesions could potentially form. The FDA has approved only 5 barrier devices for human use. However, FDA approved devices are not efficacious enough at reducing adhesion related complications to warrant their ubiquitous use (Wiseman et al., Seminal Reproductive Medicine. 2008; 26:356-68; diZerga et al., Reproductive biomedicine online. 2008; 17(3):303-6; Wilson M S. Colorectal disease: the official journal of the Association of Coloproctology of Great Britain and Ireland. 2007; 9 Suppl 2:60-5. Epub Oct. 10, 2007; Wilson et al., Colorectal disease: the official journal of the Association of Coloproctology of Great Britain and Ireland. 2002; 4(5):355-60).

Drugs tested for adhesion prevention include primarily those that affect the clotting cascade, the inflammatory process, cell proliferation, extracellular matrix production, or oxidative stress. Systemic administration of such drugs at therapeutic levels can cause undesired side effects and delay healing after surgery. Some attempts have been investigated to inject drugs into the peritoneal cavity; however, most of these studies have shown low efficacy in laboratory testing primarily because the mesothelial membrane lining the peritoneal cavity quickly absorbs drugs and subsequently distributes them throughout the body.

Salicylic acid-based poly(anhydride-esters) (SAPAEs) that hydrolytically degrade to release salicylic acid (SA) and biocompatible linker molecules have been developed (Erdmann et al., Biomaterials. 2000; 21:1941-6). SA, a non-steroidal anti-inflammatory drug (NSAID), has been found to inhibit cyclooxygenase-2 (COX-2) activity which is expressed in adhesion fibroblasts but not in normal peritoneal fibroblasts (Saed et al., Fertility and sterility. 2003; 79(6):1404-8). SA is a desirable agent for adhesion prevention as it not only has anti-inflammatory properties, but also acts as an analgesic, potentially reducing post-surgical pain. SAPAEs exhibit high drug loading capacities (up to 75%) and are able to be manipulated into various geometries depending on the application needs (Erdmann L, et al., Biomaterials. 2000; 21:1941-6; Schmeltzer et al., Polymer Bulletin. 2003; 49:441-8; Prudencio et al., Macromolecules. 2005; 38:6895-901; Schmeltzer et al., Journal of Biomaterials Science: Polymer Edition. 2008; 19(10):1295-306; Carbone A L, et al., Macromolecular Rapid Communications. 2009; 30(12):1021). As described herein, an SAPAE adhesion prevention material will allow for sustained release of salicylic acid at the site of implantation while also maintaining a temporary physical presence to block adhesion formation.

The research described herein describes the development and characterization of SAPAE:poly(ethylene glycol) (PEG) copolymers with desirable mechanical and drug release properties for an adhesion prevention device. The copolymers exhibited mechanical properties similar to or better than current injectable barrier devices on the market. In vitro drug release showed PEG content controls SA release rates and cell studies confirmed cytocompatibility and anti-inflammatory activity.

Materials and Methods

Materials

All chemicals and reagents, including poly(ethylene glycol) (PEG) 20,000 Da, were purchased from Sigma-Aldrich (Milwaukee, Wis.) and used as received.

$^1$H NMR and FTIR Spectroscopies $^1$H spectra were recorded on a Varian 500 MHz spectrometer using deuterated dimethyl sulfoxide (DMSO-d6) as the solvent and internal reference. FTIR spectra were obtained using a Thermo Nicolet/Avatar 360 spectrometer. Samples were dissolved in dichloromethane and solvent-cast on NaCl plates. Each spectrum was an average of 32 scans.

Molecular Weight

Gel permeation chromatography (GPC) was used to determine polymer number-averaged molecular weight ($M_a$) and polydispersity index (PDI) using a Perkin-Elmer liquid chromatography system consisting of a Series 200 refractive index detector, a Series 200 LC pump, and an ISS 200 autosampler. Sample automation and data processing were performed using a Dell OptiPlex GX110 computer running Perkin-Elmer TurboChrom 4 software with a Perkin-Elmer Nelson 900 Series Interface and 600 Series Link. Polymer samples dissolved in dichloromethane (DCM, 10 mg/mL) were filtered through 0.45 μm poly(tetrafluoroethylene) syringe filters. Samples were resolved on a Jordi divinylbenzene mixed-bed GPC column (7.8×300 mm, Alltech Associates, Deerfield, Ill.), with a DCM mobile phase and a flow rate of 1.0 mL/min. Molecular weights were calibrated relative to broad polystyrene standards (Polymer Source Inc., Dorval, Canada).

Thermal Properties

Differential scanning calorimetry (DSC) measurements were carried out on a TA Instrument Q200 to determine glass transition ($T_g$) and melting ($T_m$) temperatures. Measurements on samples (4-8 mg) heated under nitrogen atmosphere to 200° C. at a heating rate of 10° C./min and cooled to −50° C. at a rate of 10° C./min with a two-cycle minimum were performed. TA Instruments Universal Analysis 2000 software, version 4.5A, was used to analyze the data. $T_g$s were calculated as half Cp extrapolated.

Polymer Synthesis

SA-based diacid was synthesized according to previously described methods (FIG. 10) (Prudencio et al., Macromolecules. 2005; 38(16):6895-901.). Briefly, SA (2 equivalents (eq)) was dissolved in tetrahydrofuran (THF) and pyridine (4 eq). Adipoyl chloride (1 eq) was dissolved in THF and added drop-wise forming a white suspension. The reaction mixture was stirred overnight, quenched over water and acidified to pH 2 using concentrated hydrochloric acid. The precipitate was filtered, washed with water (3×250 mL), and dried in vacuo to yield diacid.

For the SAPAE homopolymer used in this study (referred to hereafter as SAA, FIG. 10), diacid was activated in an excess of acetic anhydride at room temperature, concentrated, and polymerized via melt-condensation polymerization at 180° C. for 5 h at 100 rpm in vacuo to yield a tan foam. $M_n$=9,000 Da, PDI=1.2. $T_g$=45° C.

For the SAPAE copolymers (referred to hereafter as SAA:PEG, FIG. 10), diacid and poly(ethylene glycol) bis(carboxymethyl) ether ($M_n$ 600, Sigma-Aldrich) were combined in weight ratios of 1:2, 1:1, and 2:1 and activated in an excess of acetic anhydride at room temperature, concentrated, and polymerized via melt-condensation polymerization at 180° C. for 3 h at 100 rpm in vacuo to yield a brown viscous liquid. Yield: 2.00 g (67%), brown viscous liquid. $^1$H NMR (500 MHz, DMSO-d$_6$, δ) for SAA:PAE copolymer: 8.21 (br, ArH), 7.93 (br, ArH), 7.77 (br, ArH), 7.39 (br, ArH), 4.41 (s, CH$_2$), 4.02 (s, CH$_2$), 3.46 (s, CH$_2$), 2.51 (br, CH$_2$), 1.65 (br, CH$_2$), peak integration varied with SAA:PEG ratio. IR (solvent-cast DCM): 1775 cm$^{-1}$ (C=O, anhydride), 1745 cm$^{-1}$ (C=O, ester).

Solvent-Casting SAA/PEG Blended Films

SAA (250 mg) and PEG 20,000 (250 mg) were dissolved in 1 mL dichloromethane and cast into a Teflon drying dish (3 cm diameter). The dish was left to evaporate overnight in a hood before being placed into a vacuum desiccator for 24 hr at room temperature to remove any remaining solvent.

Rheology

A Rheometrics SR-2000 parallel plate rheometer with the temperature set to 25 or 37° C. (TA Instruments, New Castle, Del.) was used for rheological measurements. The top plate was lowered to 0.5 mm. Oscillatory shear studies were performed ramping the frequency from 0.1 to 10 rad/s at 2% shear strain. The SAA:PEG copolymers shear viscosity was evaluated by ramping shear rates from 0.1 to 1 rad/s for the 2:1 ratio, 0.1 to 100 rad/s for the 1:1 ratio, and 1 to 500 rad/s for the 1:2 ratio. Samples were analyzed in triplicate.

Storage Stability

SAA:PEG copolymers (~0.5 g) were placed in 50 mL centrifuge tubes at −20° C., 4° C., or 25° C. Tubes were flushed with dry nitrogen before storage. Copolymer samples (1:2 ratio) were studied both with and without desiccant (Drierite, W A Hammond Drierite Co. Ltd., Xenia, Ohio). A Kimwipe (Kimberly-Clark, Irving, Tex.) taped to the tube cap suspended the desiccant away from the polymer. All other ratios were tested without desiccant only. $M_n$ and $T_g$ were analyzed for all samples each week for 3 weeks. Samples were studied in singlet due to the amount of time required for sample analysis.

In Vitro Drug Release

Polymers (50±1 mg) were placed in aluminum pans (6.3 mm diameter) to contain polymer spreading. Polymer-filled pans were placed in 20 mL Wheaton glass scintillation vials containing 10 mL phosphate buffered saline (PBS) at pH 7.4. Samples were incubated at 37° C. with agitation at 60 rpm in a controlled environment incubator shaker (New Brunswick Scientific Co., Excella E25, Edison, N.J.). All media was collected and replaced with fresh PBS (10 mL) at pre-designated time points for 14 days. Spent media was analyzed by UV spectrophotometry using a Perkin Elmer Lambda XLS spectrophotometer (Waltham, Mass.) to specifically monitor SA release. Measurements were obtained at $\lambda=303$ nm, the maximum absorbance of SA that does not overlap with other polymer degradation products. Data were calculated against a calibration curve of absorbance values from standard solutions of known SA concentrations in PBS. Polymer remaining after 14 days was degraded using basic water (pH>12) and SA was quantified to allow normalization of percent release. Samples were studied in triplicate.

In Vitro Cytotoxicity and Proliferation Assay

Polymer cytocompatibility was performed by culturing NCTC clone 929 (strain L) mouse areolar fibroblast cells (ATCC, Manassas, Va.) in media containing the dissolved polymers. These L929 fibroblast cells are a standard cell type for cytocompatibility testing as recommended by ASTM. Cell culture media consisted of Dulbecco's Modified Eagle's Medium (DMEM, Sigma-Aldrich, St. Louis, Mo.), 10% v/v fetal bovine serum (Atlanta Biologicals, Lawrenceville, Ga.), 1% L-glutamate (Sigma) and 1% penicillin/streptomycin. The polymers were dissolved in dimethyl sulfoxide (DMSO) at 100, 50, 10, 5, and 1 mg/mL. These solutions were then diluted with cell culture media to achieve concentrations of 1, 0.5, 0.1, 0.05, and 0.01 mg/mL and 1% DMSO. A control with 1% DMSO in media without polymer was prepared. Three 96-well plates were seeded at an initial concentration of 2,000 cells per well with each experimental group plated in triplicate. For the L929 fibroblasts, cell viability was determined by using a CellTiter 96®AQueous One Solution Cell Proliferation Assay (MTS, Promega, Madison, Wis.) at 24, 48, and 72 hours. After 2 hr incubation with MTS, the absorbance was recorded with a microplate reader at $\lambda=490$ nm. One-way ANOVAs followed by Bonferroni's all-pairs comparison were used to determine significance (significantly different if $p<0.05$).

TNF-α Secretion Assay

Human blood-derived monocytes (Blood Center of New Jersey, East Orange, N.J.) were used to determine the polymer efficacy on decreasing inflammatory cytokine secretion. The cell isolation and purification protocol used was previously described by Kim et al. (Kim et al., Experimental Hematology. 2009; 37(12):1445-53). Briefly, peripheral blood mononuclear cells were collected from blood of healthy donors by density gradient separation using Ficoll-PLUS (GE Healthcare, Piscataway, N.J.). Red blood cells were lysed by incubation in ammonium-potassium-chloride lysing buffer for 5 min, washed with PBS and counted. Monocytes were cultured on 175 cm² flasks (BD, Franklin Lakes, N.J.) at a concentration of $8 \times 10^6$ cells/mL in Roswell Park Memorial Institute (RPMI) 1640 media (GIBCO BRL, Rockville, Md.). RPMI media was supplemented with 10% fetal bovine serum (FBS) (GIBCO BRL), 100 units/mL penicillin (GIBCO BRL), 100 µg/mL streptomycin (GIBCO BRL) and 400 mM L-glutamine (GIBCO BRL). Monocytes were allowed to adhere for 2 h and then washed 3 times with PBS to remove non-adherent cells. Monocytes were cultured for 7 days at 37° C. and 5% $CO_2$ in RPMI supplemented with 5 ng/mL granulocyte-macrophage colony-stimulating factor (GM-CSF) (R&D Systems, Minneapolis, Minn.) to generate macrophages.

After 7 days of culture, macrophages were washed once with PBS and then detached with trypsin-EDTA (GIBCO) for 30 minutes at room temperature. Cells were re-suspended in culture medium (RPMI), counted, re-plated at $8 \times 10^3$ cells/well in a 96 well plate, and allowed to attach overnight. The following day, the media was replaced with the various sample groups: polymer containing media (0.2 mg/mL polymer, 10 ng/mL lipopolysaccharide (LPS), 1% DMSO), a positive control (10 ng/mL LPS, 1% DMSO), and a negative control (no LPS, 1% DMSO). All cell studies were performed in triplicate. LPS (10 ng/mL) induced macrophage TNF-α secretion. After 48 h, media was collected and TNF-α secretion was determined with an enzyme-linked immunosorbent assay kit against human TNF-α (BioLegend, San Diego, Calif.). A CellTiter 96®AQueous One Solution Cell Proliferation Assay (Promega, Madison, Wis.) was used to ensure that differences in TNF-α secretion were not due to differences in cell viability. A one-way ANOVA followed by Bonferroni's all-pairs comparison was used to determine significance (significantly different if $p<0.05$).

Results and Discussion

SAPAE:PEG Blended Films

SAPAE homopolymers are hard and glassy at physiological temperatures, making them unfeasible as adhesion barrier devices on their own. The first method attempted to create an adhesion barrier material used SAA, the most well characterized SAPAE, blended with PEG. PEG was chosen as it has favorable mechanical characteristics, has been used in other barrier devices, and can inhibit protein adsorption to surfaces, thereby decreasing the likelihood of cell adhesion to the barrier as it degrades (Tziampazis et al., Biomaterials. 2000; 21(5):511-20). The polymers were concurrently dissolved and solvent-cast to create a film. The resulting film crumbled when removed from the Teflon dish it had been cast in. Unlike typical solvent cast films of SAA, the film surface was not smooth; the variegated surface of the blended films indicated macroscopic phase separation.

DSC spectra of SAA, PEG, and the SAA/PEG film were determined. If the polymer blend were completely miscible, the thermal transitions for the blend would have intermediary values between the homopolymer values transitions (Brostow et al., Materials Letters. 2008; 62(17-18):3152-5). The thermal transition for the blend appears to be more additive than intermediary as the SAA $T_g$ drop and PEG $T_m$ are still visible despite their overlap. The DSC curves and film topography indicate immiscibility and phase separation.

SAPAE:PEG Copolymers

Figure 10:
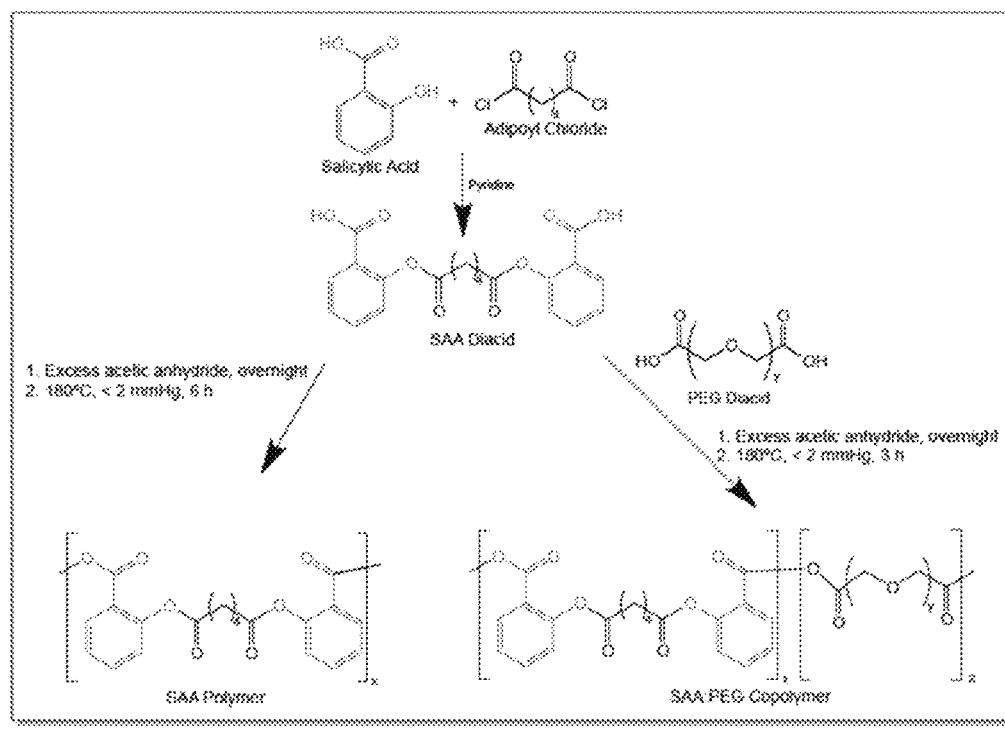
FIG. 10. Synthetic scheme for the SAA diacid, SAA polymer, and SAA:PEG copolymers.

Due to the poor mechanical properties and phase separation, which could result in uneven degradation and drug release, other methods of incorporating PEG with SAA were pursued. Specifically, carboxylic acid-terminated PEG chains (Sigma-Aldrich) were purchased for copolymerization with SAA monomers to allow the copolymers to be formed using standard melt polymerization techniques (FIG. 10).

Copolymer Characterization

Figure 11:
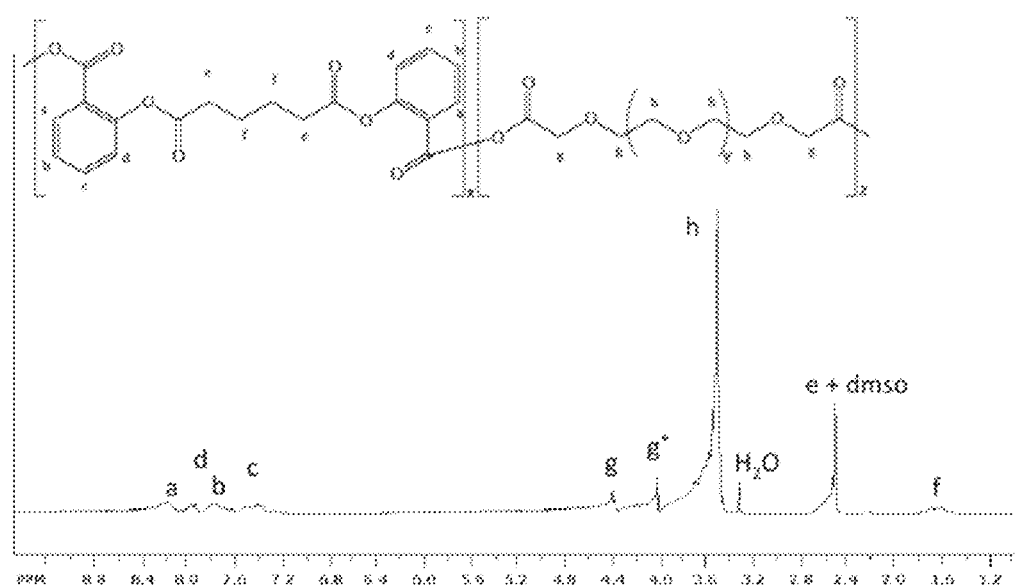
FIG. 11. $^1$H NMR spectra of 2:1 SAA:PEG (g* indicates hydrogen atoms adjacent to a carboxylic acid end group, as opposed to g which indicates hydrogen atoms adjacent to an anhydride group).

The resulting copolymers formed brown viscous liquids at room temperature (FIG. 8). These liquids were very sticky, a good quality for an adhesion barrier as this property will help the material adhere to the administered site and remain in place throughout the healing process. $^1$H NMR (FIG. 11) and FTIR spectroscopies were used to confirm the products. $^1$H NMR peak integrations confirmed that theoretical and experimental SAA:PEG ratios were similar. FTIR confirmed the presence of anhydride and ester bonds in the various polymers. Typical $M_n$, PDI, and $T_g$ values for the copolymer ratios studied are summarized in Table 4. A significant decrease in the copolymer $T_g$ as compared to the homopolymer (45° C.) was observed.

TABLE 4

Typical $M_n$, PDI, and $T_g$ for SAA:PEG Polymers.

| SAA:PEG Ratio | $M_n$ (Da) | PDI | $T_g$ (° C.) |
|---|---|---|---|
| 2:1 | 23,700 | 44.6 | −5 |
| 1:1 | 16,500 | 22.2 | −25 |
| 1:2 | 39,200 | 31.7 | −35 |
| 1:0 (SAA homopolymer) | 9,000 | 1.2 | 45 |

Rheology

With $T_g$s below 0° C., the polymers behaved as viscous liquids at room temperature, as opposed to the glassy SADEM homopolymers. To assess the copolymer mechanical properties, rheological studies were performed. Initial oscillatory measurements demonstrated a phase angle of approximately 90°. This data indicates that the polymers primarily undergo viscous deformation with negligible elastic deformation. The results of subsequent linear shear viscosity ramping measurements are given in Table 5. Shear viscosities decreased by an order-of-magnitude as PEG content increased. Increasing the sample temperatures from 25° C. to 37° C. resulted in a decrease in shear viscosity by about half an order-of-magnitude. These patterns suggest an ability to tailor copolymer rheological properties by changing PEG content.

TABLE 5

Shear Viscosities of SAA:PEG Copolymers

| SAA:PEG Ratio | Shear Viscosity at 25° C. (mPa · s) | Shear Thinning Observed (25° C., rad/s) | Shear Viscosity at 37° C. (mPa · s) | Shear Thinning Observed (37° C., rad/s) |
|---|---|---|---|---|
| 2:1 | $6.5 \times 10^7 \pm 1.8 \times 10^7$ | N/A | $8.5 \times 10^6 \pm 3.7 \times 10^6$ | N/A |
| 1:1 | $7.3 \times 10^6 \pm 0.8 \times 10^6$ | 2 | $1.6 \times 10^6 \pm 0.4 \times 10^5$ | 10 |
| 1:2 | $2.2 \times 10^5 \pm 0.1 \times 10^5$ | 100 | $6.9 \times 10^4 \pm 0.1 \times 10^4$ | 200 |

These shear viscosity values compare well with Intercoat® (Ethicon, Somerville, N.J.), an injectable adhesion barrier currently on the market. Intercoat® is a carboxymethylcellulose and PEG blend with a viscosity of about $2.1 \times 10^5$ mPa·s (diZerega et al., Journal of Biomedical Materials Research Part B: Applied Biomaterials. 2007; 81B(1): 239-50), similar to the 1:2 SAA:PEG copolymer described here. Additionally, evidence suggests that as the viscosity of a barrier increases, so does the efficacy. This result indicates that the SAA:PEG copolymers may have mechanical properties suitable for the prevention of adhesions. However, a balance must be made between the ability of a material to remain in place in vivo and the ease of surgical application. While both the 1:1 and 1:2 copolymers can be extruded from a syringe, the 2:1 copolymer can only be extruded with extreme effort. The ease of application is an important consideration for surgical use and suggests that the optimal SAA:PEG ratio is below 2:1 for injectable applications.

Storage Stability

Figure 12:
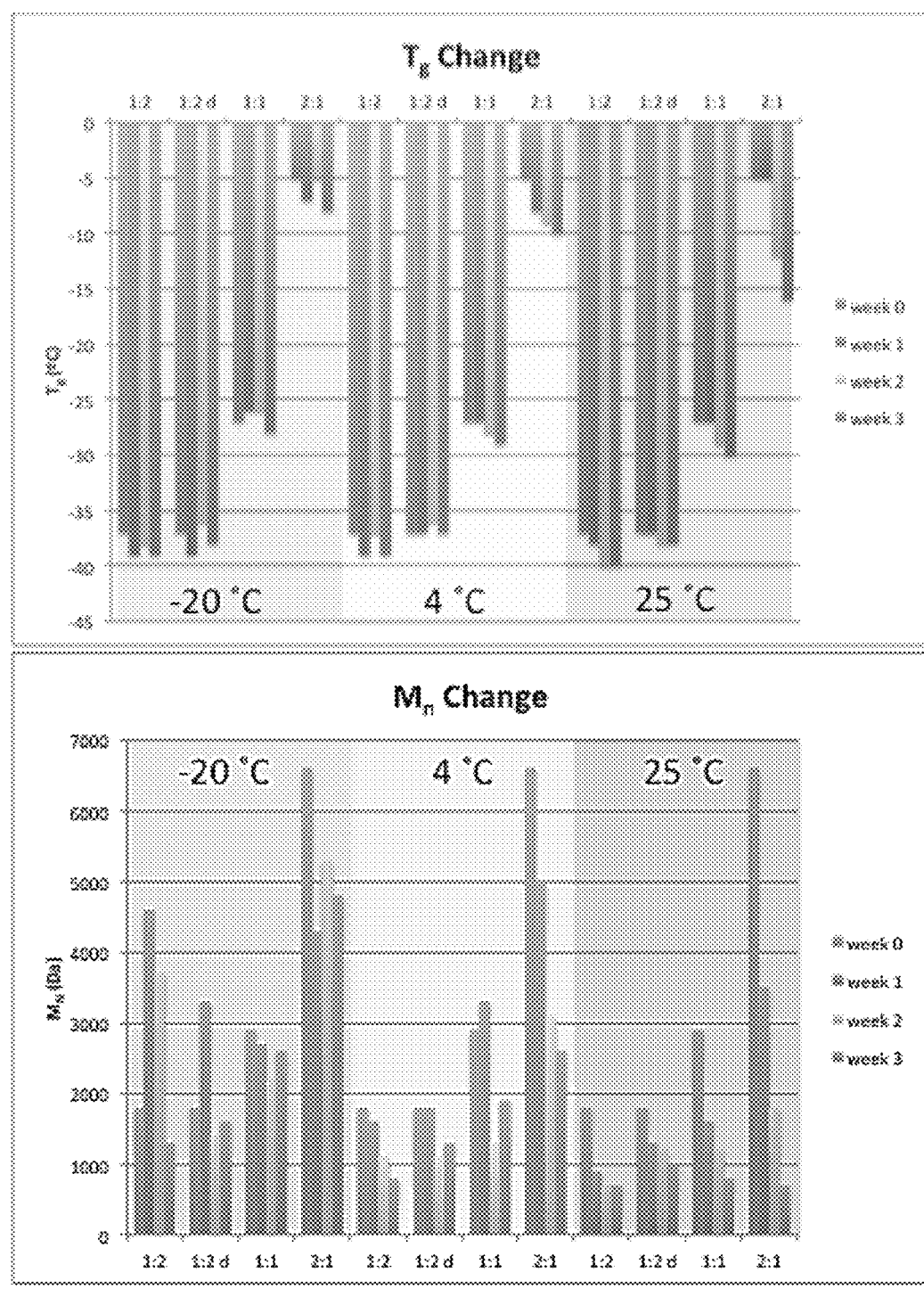
FIG. 12. SAA:PEG copolymer $M_n$ and $T_g$ changes over 3 weeks of storage at different temperatures. Specifically, copolymers with ratios of 1:2 (without desiccant), 1:2d (with desiccant), 1:1 and 2:1 were analyzed at −20° C., 4° C. and 25° C. From left to right, each bar represents the following time point within each grouping (e.g., grouping 1:2): week 0, week 1, week 2 and week 3.

Copolymer storage stability is an issue as their degradation over time affects both physicochemical properties and drug release rates. Copolymers were stored in the freezer, refrigerator, and at ambient temperatures. The molecular weight and glass transition temperatures were monitored weekly for 3 weeks to assess the rate of degradation of samples under the various conditions (FIG. 12). As only one data set was taken, variability is observed, resulting in increases in $M_n$ and $T_g$ at some time points. GPC column issues resulting in fluctuating baselines could also have affected $M_n$ measurements. However, there is a general trend observed between groups. Colder environments slowed the rate of polymer degradation. This fact can be seen in the dramatic differences in 0 and 3 week $M_n$ and $T_g$ values for polymers at 25° C. as compared to the slight differences between 0 and 3 weeks for samples maintained at −20° C. As PEG is hygroscopic, it is expected to increase polymer degradation rates, thus, the copolymer with the greatest amount of PEG (1:2 copolymer) was stored both with and without desiccant to reduce degradation rates. The desiccant effect is most obvious on the molecular weight, with only slight differences observed in the $T_g$. Due to these results, all copolymers were subsequently stored in the freezer in a secondary container with desiccant.

In Vitro Drug Release

Figure 13:
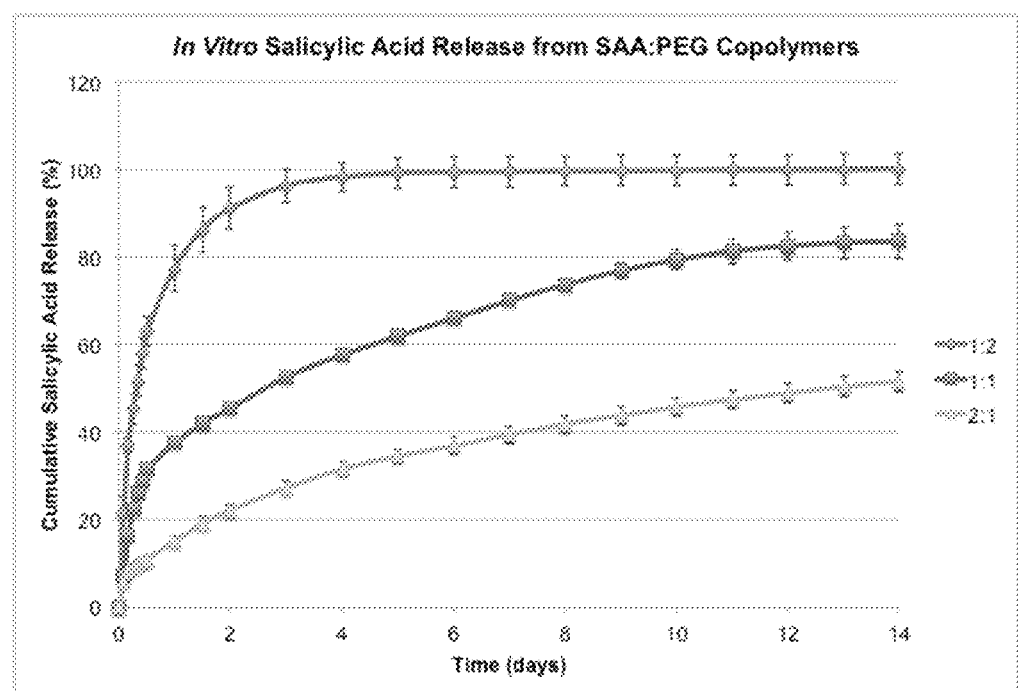
FIG. 13. In vitro SA release from SAA:PEG copolymers.

SAPAEs are hydrolytically degradable and the incorporation of hydrophilic PEG moieties was expected to significantly effect drug release rates. FIG. 13 shows the SA release profiles from the SAA:PEG copolymers. The 1:2 copolymer completely degraded in less than a week, with 77% of incorporated SA released within the first 24 hours. The 1:1 and 2:1 copolymers exhibit lesser release within the first day (37% and 15%, respectively). The initial release correlated with the PEG content where increasing PEG led to greater SA release. In comparison, the SAA homopolymer exhibits a 2-day lag period (Ouimet et al., Journal of Bioactive and Compatible Polymers. 2012; 27(6):540-9). For the 1:1 and 2:1 copolymers, after the initial release, the release rate stabilized to give a more linear profile. Average release after day 1 was 3.5% from the 1:1 samples and 2.8% from the 2:1 samples. On day 14, basic water was used to completely degrade remaining polymer to determine total SA content. SA content from remaining polymer was used to normalize cumulative release data. After 14 days, the 1:1 and 2:1 copolymers released 85% and 52% SA, respectively.

It has been reported that the critical period for adhesion prevention is the first 7-10 days after injury (Moran, Colorectal disease: the official journal of the Association of Coloproctology of Great Britain and Ireland. 2007; 9 Suppl 2:39-44; van der Wal J B, et al., Colorectal disease: the official journal of the Association of Coloproctology of Great Britain and Ireland. 2007; 9 Suppl 2:9-13). While the 1:2 copolymer does not provide drug release or physical barrier properties over this time period, many factors should be considered. For example, the rate of degradation in vitro and in vivo may vary dramatically. Additionally, the amount of polymer used and how it is placed in the body will have an effect on polymer duration in vivo. The increased shear stress in vivo would also most likely result in increased degradation rates. Alternatively, if the initial inflammatory response is correctly modulated (inflammatory cytokine concentrations in the peritoneal cavity peak within the first 24 hours after abdominal surgery) (Sammour T, World Journal of Surgery. 2010; 34(4):704-20), drug release and physical presence may not be as important at later times and the polymer may not need to remain in the body for 10 days.

Cytocompatability

Figure 14A:
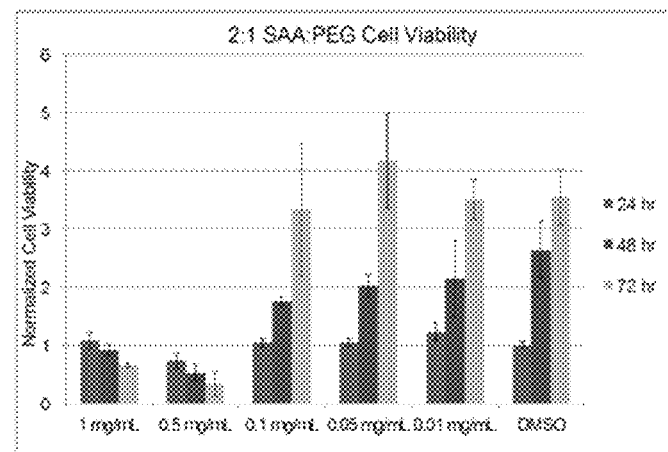
FIG. 14A-C. In vitro cell viability over 72 hours for cells exposed to SAA:PEG copolymers with ratios of 1:2 (FIG. 14A), 1:1 (FIG. 14B), and 2:1 (FIG. 14C) (* indicates significant decrease from DMSO control, p<0.05). Cell viability was normalized to the DMSO control at 24 hours. Cell viability is shown, from left to right, within each concentration group at 24 hours, 48 hours and 72 hours.
Figure 14B:
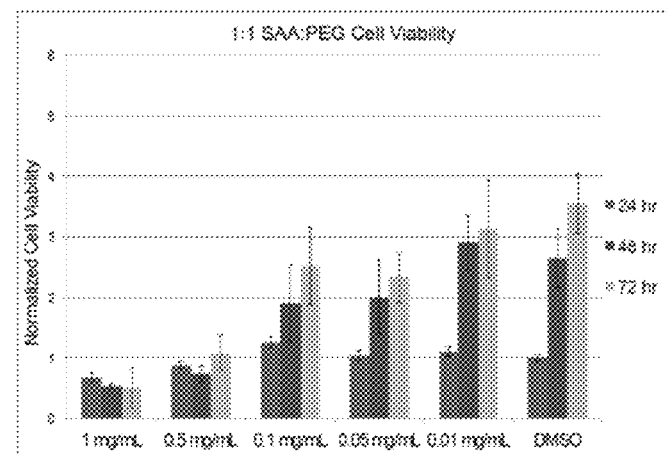
Figure 14C:
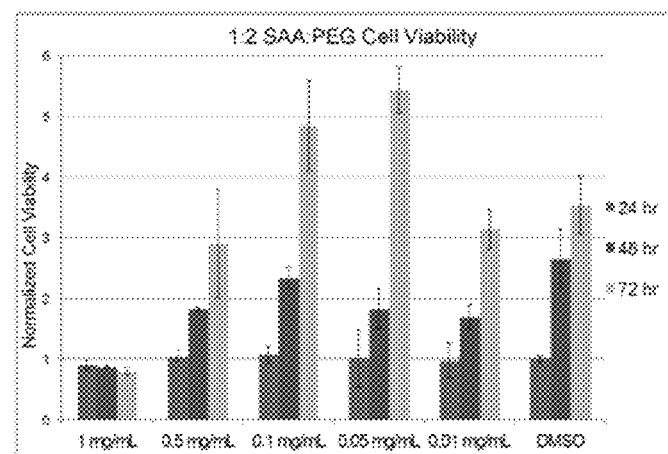

Copolymer (0.01 to 1 mg/mL) cytocompatibility was evaluated over 3 days (FIG. 14A-C). All polymers were cytotoxic when dissolved at 1 mg/mL, compared to the 1% DMSO control. The polymers with higher drug loading (1:1 and 2:1) were also toxic at 0.5 mg/mL. Below these levels, no significant toxicity over the three days was observed. It should be noted, however, that in these studies, the polymers were dissolved in solution, which increases polymer degradation rate compared to expected in vivo degradation.

These levels of cytotoxicity are an important consideration for in vivo use. Rapid polymer degradation could lead to locally toxic effects if too much polymer is used or if the polymer is placed in an area of the body that could not absorb the polymer degradation products quickly. This rapid degradation should not pose a problem in the peritoneal cavity, where most problematic fibrous adhesions occur, as the peritoneal cavity absorbs fluids rapidly.

Anti-Inflammatory Activity

Figure 15:
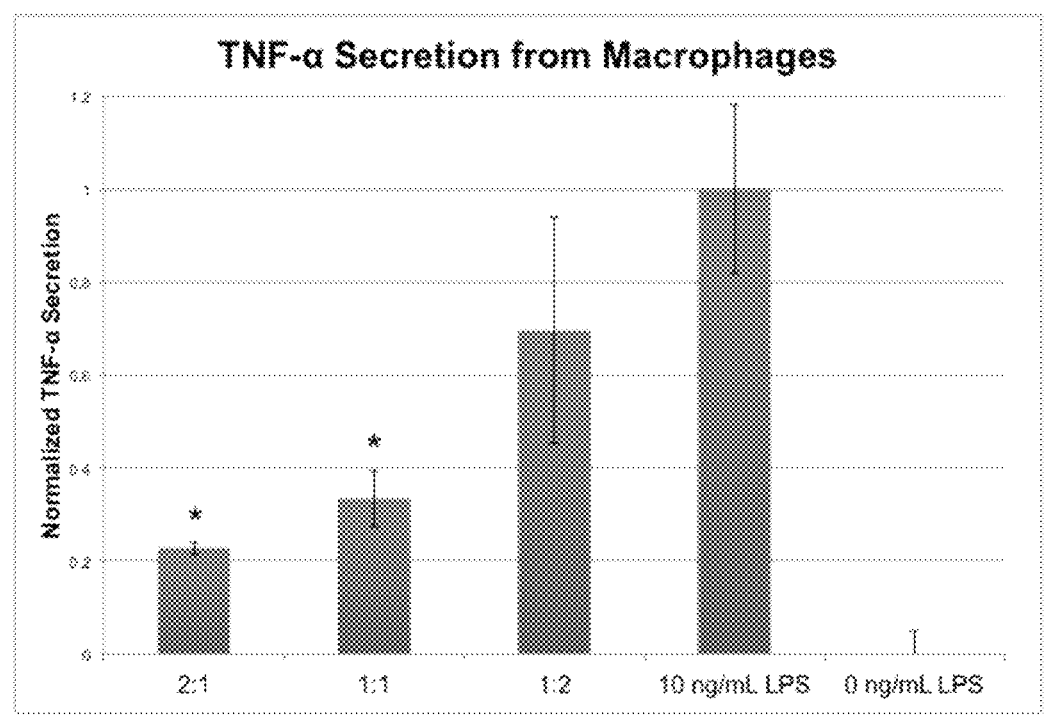
FIG. 15. TFN-α expression by macrophages exposed to LPS and SAA:PEG copolymers (* indicates significant difference from 10 ng/mL LPS control, p<0.05). TNF-α secretion was normalized to the LPS positive control (set to 1) and the LPS free control (set to 0).

Many inflammatory cytokines, such as TNF-α, can lead to adhesion cell phenotype differentiation. Macrophages were exposed to 10 ng/mL LPS to elicit an immune response resulting in TNF-α secretion. ELISA was used to monitor the copolymer effect on macrophage TNF-α production. The copolymers exhibited TNF-α knockdown in a dose-dependent manner correlating with the amount of SA loading in the polymer (FIG. 15). At 0.2 mg/mL, 2:1 and 1:1 copolymers significantly decreased TNF-α expression while the 1:2 copolymer reduced expression but not statistically significantly. Cytotoxicity assays were performed to confirm that TNF-α knockdown was not due to cell death (data not shown).

CONCLUSION

Fibrous adhesions are a prevalent medical issue. Currently employed physical barrier devices and pharmaceutical regimens are not efficacious at preventing adhesion related complications. The SAA:PEG copolymers described herein combine these two approaches. The polymers could be used as an injectable barrier substance to physically prevent adhesion formation between tissue surfaces. They could also provide controlled, sustained SA release which may be able to prevent fibroblast differentiation into the adhesion phenotype. Studies to assess adhesion prevention efficacy in vivo may be performed subsequently (e.g., in vivo murine studies) by the skilled artisan using known techniques.

The invention described herein also comprises compositions, devices, methods of use and methods of treatment which are disclosed herein, e.g., in Examples 1-4.

All documents cited herein are incorporated by reference. While certain embodiments of invention are described, and many details have been set forth for purposes of illustration, certain of the details can be varied without departing from the basic principles of the invention.

The use of the terms "a" and "an" and "the" and similar terms in the context of describing embodiments of invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. In addition to the order detailed herein, the methods described herein can be performed in any suitable order unless otherwise indicated herein or otherwise clearly contradicted by context. The use of any and all examples, or exemplary language (e.g., "such as") provided herein, is intended merely to better illuminate embodiments of invention and does not necessarily impose a limitation on the scope of the invention unless otherwise specifically recited in the claims. No language in the specification should be construed as indicating that any non-claimed element is essential to the practice of the invention.

What is claimed is:

1. A therapeutic method for treating a wound, preventing fibrous adhesions at a wound site and/or providing localized analgesia at a wound site in an animal comprising administering to an animal in need of such therapy an effective amount of a copolymer having a backbone, wherein the backbone comprises a) one or more polyanhydride units that comprise a group that will yield a biologically active agent upon hydrolysis of the backbone; and b) one or more units of formula (II):

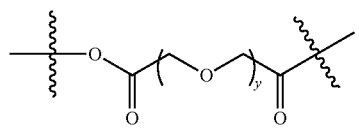

wherein y is 5 to 15.

2. The method of claim 1, wherein the polyanhydride comprises one or more units of formula (I) in the backbone:

$$—C(=O)R^1\text{-}A\text{-}L\text{-}A\text{-}R^1C(=O)—O— \quad (I)$$

wherein each $R^1$ is a group that will provide a biologically active agent upon hydrolysis of the polymer;

each A is independently an ester or an amide linkage; and each L is independently a linker molecule.

3. The method of claim 2, wherein A is independently an ester linkage.

4. The method of claim 2, wherein L is a divalent, branched or unbranched, saturated or unsaturated, hydrocarbon chain, having from 1 to 25 carbon atoms, wherein one or more of the carbon atoms is optionally replaced by (—O—), (—NR—) or phenylene, and wherein the chain is optionally substituted on carbon with one or more substituents selected from the group consisting of $(C_1\text{-}C_6)$alkoxy, $(C_3\text{-}C_6)$cycloalkyl, $(C_1\text{-}C_6)$alkanoyl, $(C_1\text{-}C_6)$alkanoyloxy, $(C_1\text{-}C_6)$alkoxycarbonyl, $(C_1\text{-}C_6)$alkylthio, azido, cyano, nitro, halo, hydroxy, oxo, carboxy, aryl, aryloxy, heteroaryl, and heteroaryloxy, wherein each R is independently selected from H or $(C_1\text{-}C_6)$alkyl.

5. The method of claim 2, wherein L is —$CH_2CH_2CH_2CH_2$— or —$CH_2C(Et)_2CH_2$—.

6. The method of claim 1, wherein the biologically active agent is an antimicrobial, anti-inflammatory, antioxidant, analgesic, anticoagulant or fibrinolytic.

7. The method of claim 6, wherein the biologically active agent is an anti-inflammatory agent.

8. The method of claim 7, wherein the anti-inflammatory agent is salicylic acid.

9. The method of claim 1, wherein the ratio of the a) one or more units that comprise a group that will yield a biologically active agent upon hydrolysis of the backbone to the b) one or more units of formula (II), ranges from between about 5:1 to about 1:5.

10. The method of claim 9, wherein the ratio ranges from 2:1 to 1:2.

11. The method of claim 10, wherein the ratio is 1:1 or 2:1.

12. The method of claim 1, wherein the copolymer comprises one or more units of formula (III):

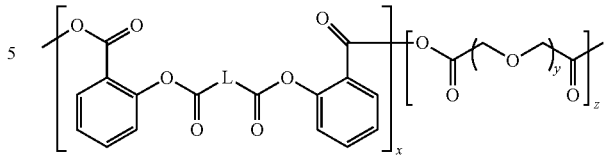

wherein each L is independently a linker molecule;

x is 5 or more;

y is 5 to 15; and z is 5 or more.

13. The method of claim 1, wherein the copolymer has an average molecular weight of about 10,000 daltons to about 30,000 daltons.

14. The method of claim 1, wherein the copolymer further comprises a second biologically active agent dispersed in the matrix of the copolymer.

15. The method of claim 1, wherein a pharmaceutical composition comprising the copolymer and a pharmaceutically acceptable carrier is administered to the animal in need of such therapy.

16. A therapeutic method for preventing fibrous adhesions at a wound site in an animal comprising administering to an animal in need of such therapy an effective amount of a copolymer having a backbone, wherein the backbone comprises a) one or more polyanhydride units that comprise a group that will yield a biologically active agent upon hydrolysis of the backbone; and b) one or more units of formula (II):

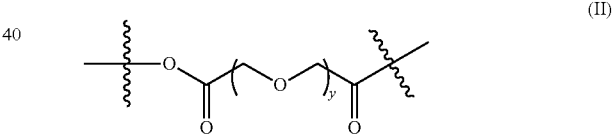

wherein y is 5 to 15.

17. A therapeutic method for preventing fibrous adhesions at a wound site in an animal comprising administering to an animal in need of such therapy an effective amount of a copolymer comprising one or more units of formula (IIIa):

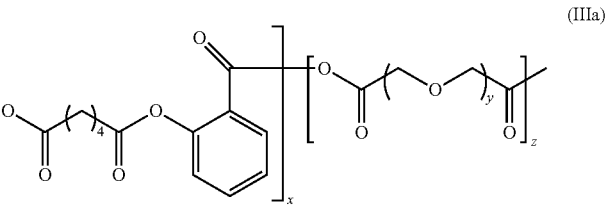

wherein x is 5 or more;

y is 5 to 15; and z is 5 or more.

* * * * *